US009630060B2

(12) United States Patent
Volkerink et al.

(10) Patent No.: US 9,630,060 B2
(45) Date of Patent: Apr. 25, 2017

(54) EXERCISE EQUIPMENT WITH IMPROVED USER INTERACTION

(71) Applicant: Flextronics AP, LLC, San Jose, CA (US)

(72) Inventors: Hendrik J. Volkerink, Palo Alto, CA (US); David Gonsiorowski, Granite Bay, CA (US); Yossef Schvetz, Sesto San Giovanni (IT); Serdar Ozsumer, Milan (IT)

(73) Assignee: Flextronics AP, LLC, San Jose, CA (US)

( * ) Notice: Subject to any disclaimer, the term of this patent is extended or adjusted under 35 U.S.C. 154(b) by 3 days.

(21) Appl. No.: 14/631,567

(22) Filed: Feb. 25, 2015

(65) Prior Publication Data

US 2015/0238819 A1 Aug. 27, 2015

Related U.S. Application Data

(60) Provisional application No. 61/945,654, filed on Feb. 27, 2014.

(51) Int. Cl.
*A63B 24/00* (2006.01)
*A63B 21/00* (2006.01)
(Continued)

(52) U.S. Cl.
CPC .......... *A63B 24/0087* (2013.01); *A61B 5/486* (2013.01); *A63B 21/0059* (2015.10); *A63B 21/00076* (2013.01); *A63B 22/0242* (2013.01); *A63B 71/0619* (2013.01); *A61B 5/747* (2013.01); *A63B 69/16* (2013.01);
(Continued)

(58) Field of Classification Search
CPC . A63B 24/00; A63B 24/0062; A63B 24/0087; A63B 21/00076; A63B 21/0059; A63B 2071/009; A63B 2071/0636; A63B 2071/0644; A63B 2071/0677; A63B 2071/068; A63B 2071/0683; A63B 22/0242; A63B 2022/0278; A63B 2220/12; A63B 2220/40; A63B 2220/72; A63B 2220/74; A63B 2220/75; A63B 2220/806; A63B 2230/01; A63B 2230/06;
(Continued)

(56) References Cited

U.S. PATENT DOCUMENTS 6,244,987 B1 * 6/2001 Ohsuga ................. A63B 24/00 434/247
7,227,526 B2 * 6/2007 Hildreth ................ G06T 19/006 345/156

(Continued)

*Primary Examiner* — Glenn Richman
(74) *Attorney, Agent, or Firm* — Sheridan Ross P.C.

(57) ABSTRACT

Methods and systems are presented for accepting inputs into a treadmill or other exercise equipment to control functions of the treadmill or exercise equipment. An exercise control system can receive gestures and other inputs. The exercise control system can also obtain information about the user of the exercise control system and information about the environment in which the exercise equipment is operating. Based on the input and the other information, the exercise control system can modify or improve the performance or execution of user interface and functions of the exercise equipment. The changes make the user interfaces and/or functions user-friendly and intuitive.

20 Claims, 38 Drawing Sheets

(51) Int. Cl.
  *A63B 71/06* (2006.01)
  *A63B 22/02* (2006.01)
  *A63B 21/005* (2006.01)
  *A61B 5/00* (2006.01)
  *A63B 71/00* (2006.01)
  *A63B 69/16* (2006.01)

(52) U.S. Cl.
  CPC . *A63B 2022/0278* (2013.01); *A63B 2071/009* (2013.01); *A63B 2071/063* (2013.01); *A63B 2071/068* (2013.01); *A63B 2071/0636* (2013.01); *A63B 2071/0644* (2013.01); *A63B 2071/0658* (2013.01); *A63B 2071/0677* (2013.01); *A63B 2071/0683* (2013.01); *A63B 2220/12* (2013.01); *A63B 2220/40* (2013.01); *A63B 2220/72* (2013.01); *A63B 2220/74* (2013.01); *A63B 2220/75* (2013.01); *A63B 2220/806* (2013.01); *A63B 2225/20* (2013.01); *A63B 2225/50* (2013.01); *A63B 2230/01* (2013.01); *A63B 2230/06* (2013.01); *A63B 2230/30* (2013.01); *A63B 2230/50* (2013.01); *A63B 2230/75* (2013.01)

(58) Field of Classification Search
  CPC ............ A63B 2230/30; A63B 2230/50; A63B 2230/75; G06F 3/017
  See application file for complete search history.

(56) References Cited

U.S. PATENT DOCUMENTS

| | | | |
|---|---|---|---|
| 7,777,899 B1* | 8/2010 | Hildreth | G01B 11/03 356/614 |
| 8,421,642 B1* | 4/2013 | McIntosh | G06F 3/017 340/539.1 |
| 2001/0001303 A1* | 5/2001 | Ohsuga | A63B 24/00 482/5 |

* cited by examiner

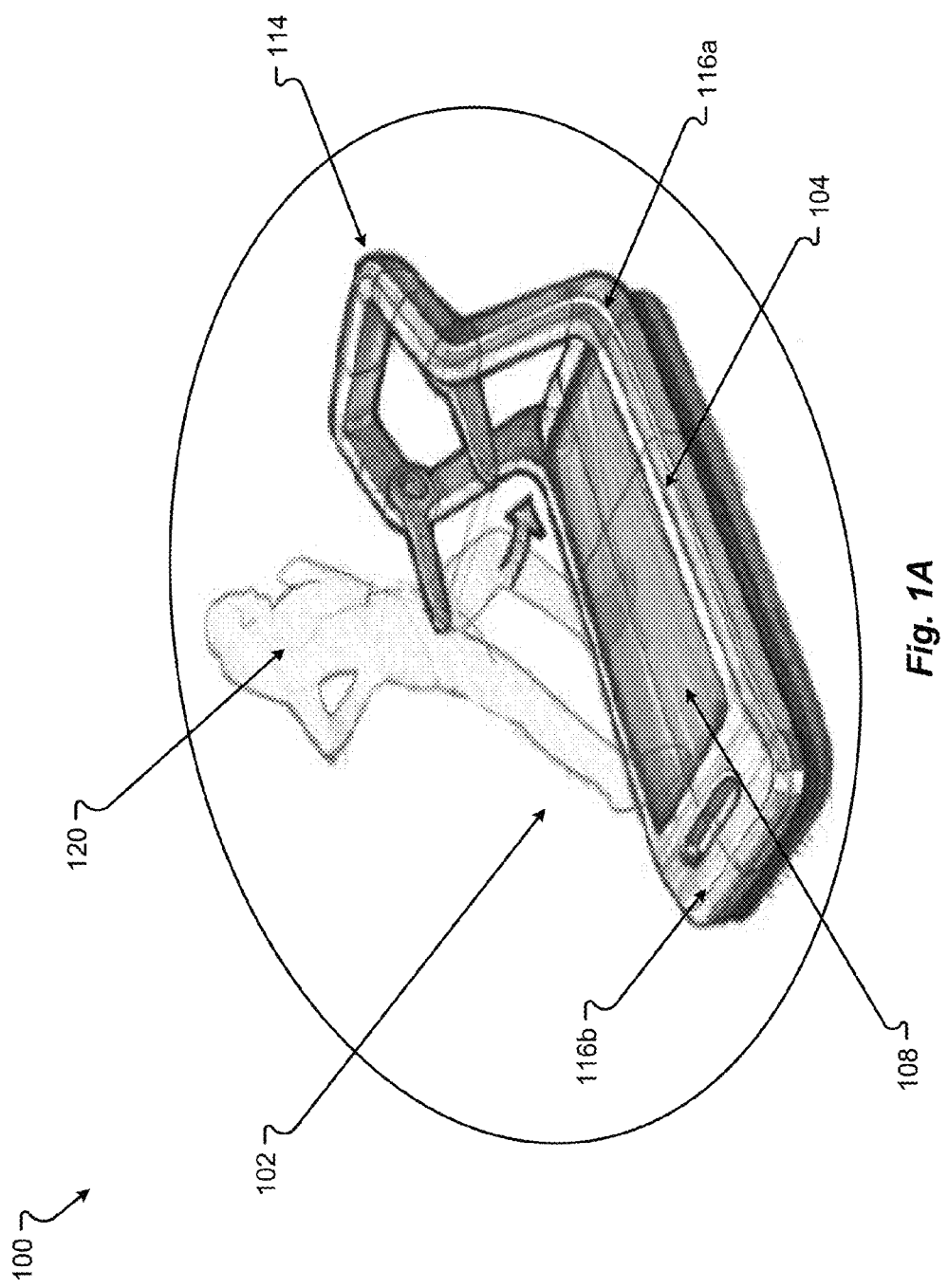

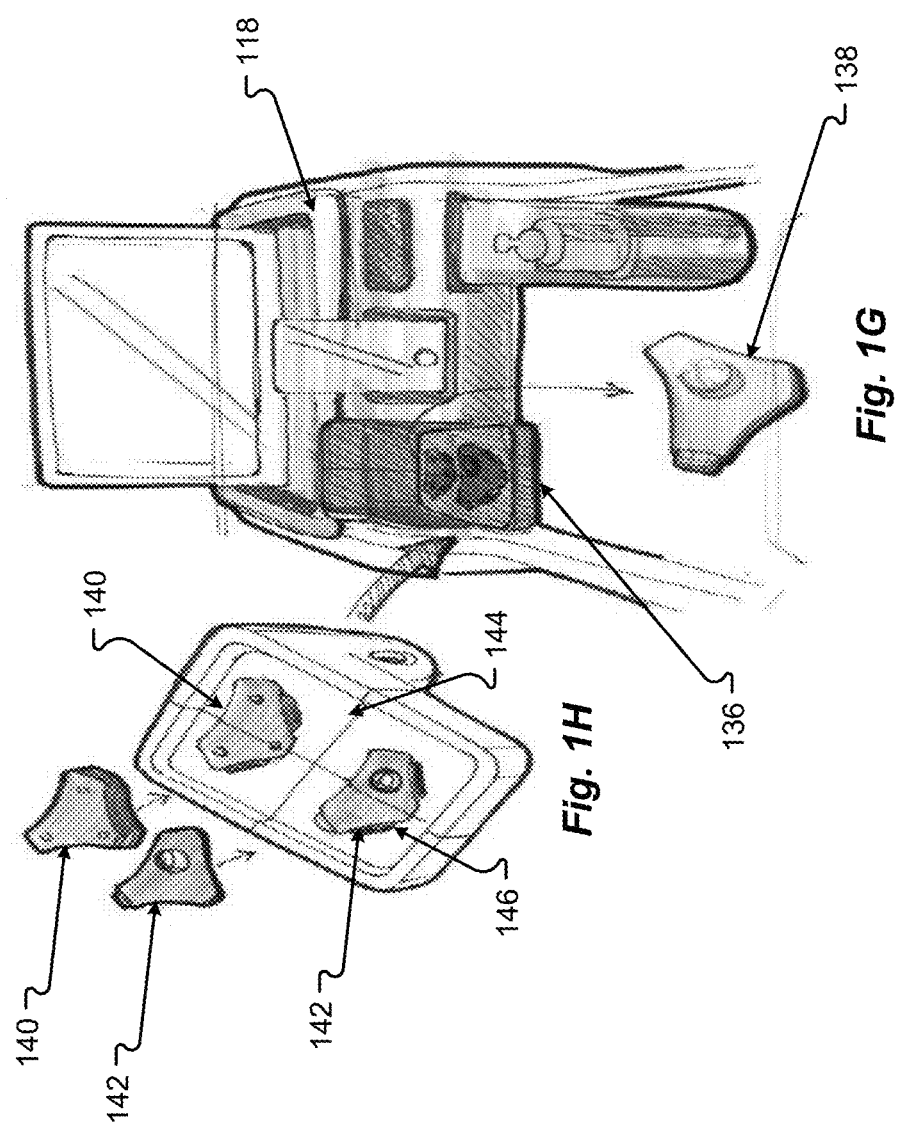

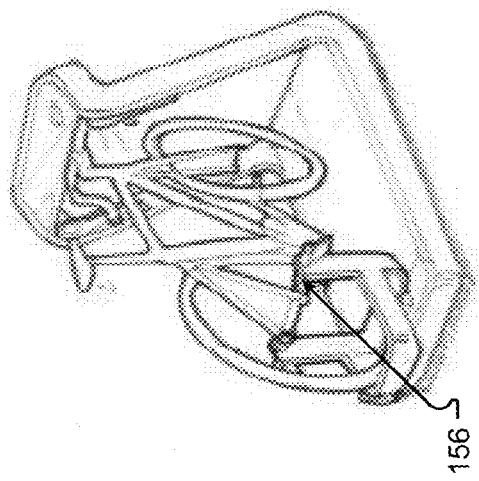
*Fig. 1M*
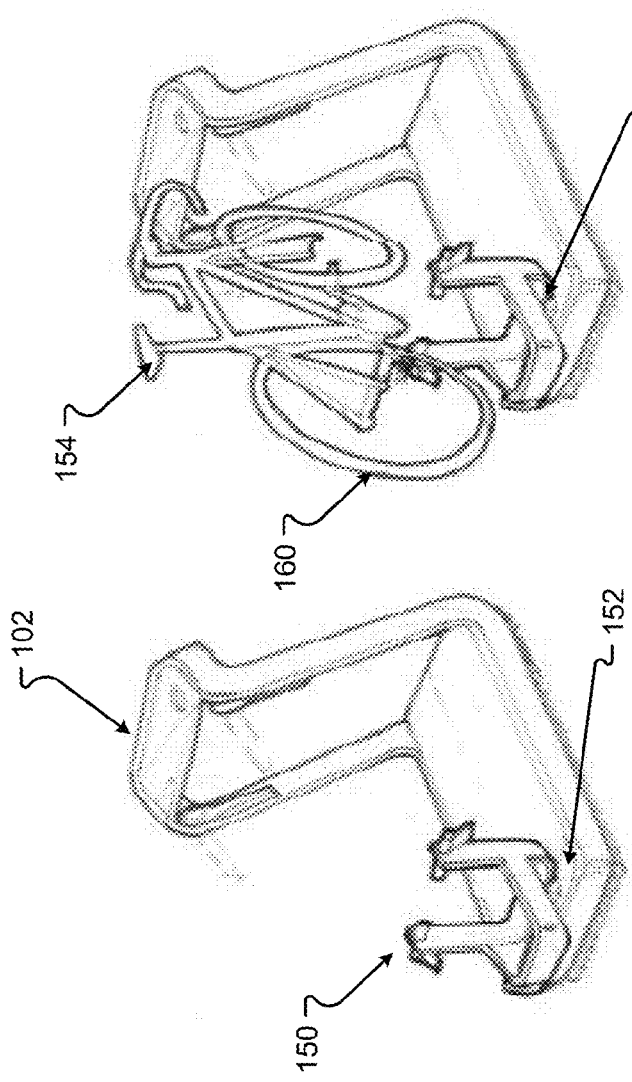
*Fig. 1L*
*Fig. 1K*

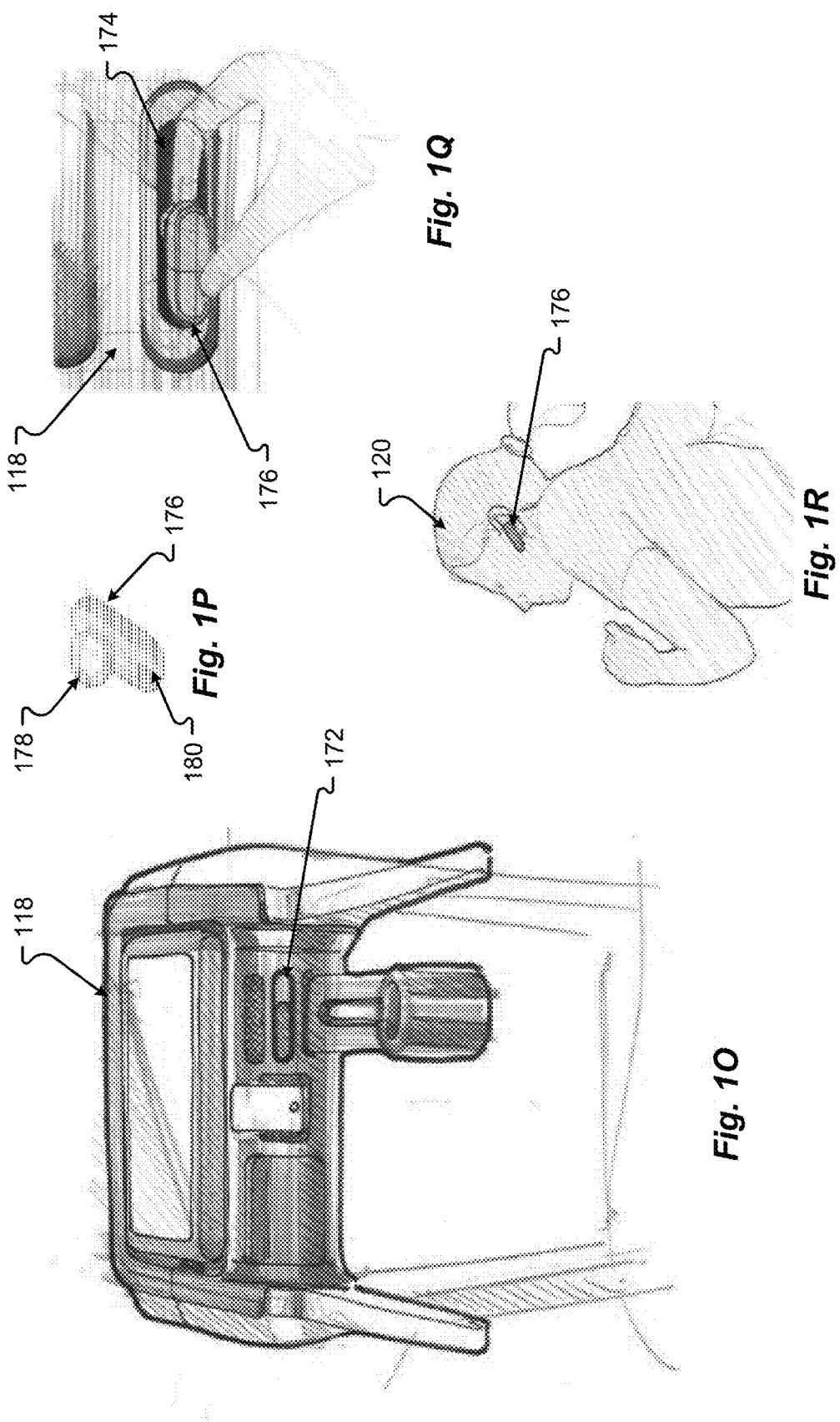

Tap

Long Press

Drag

Flick

Pinch

Spread

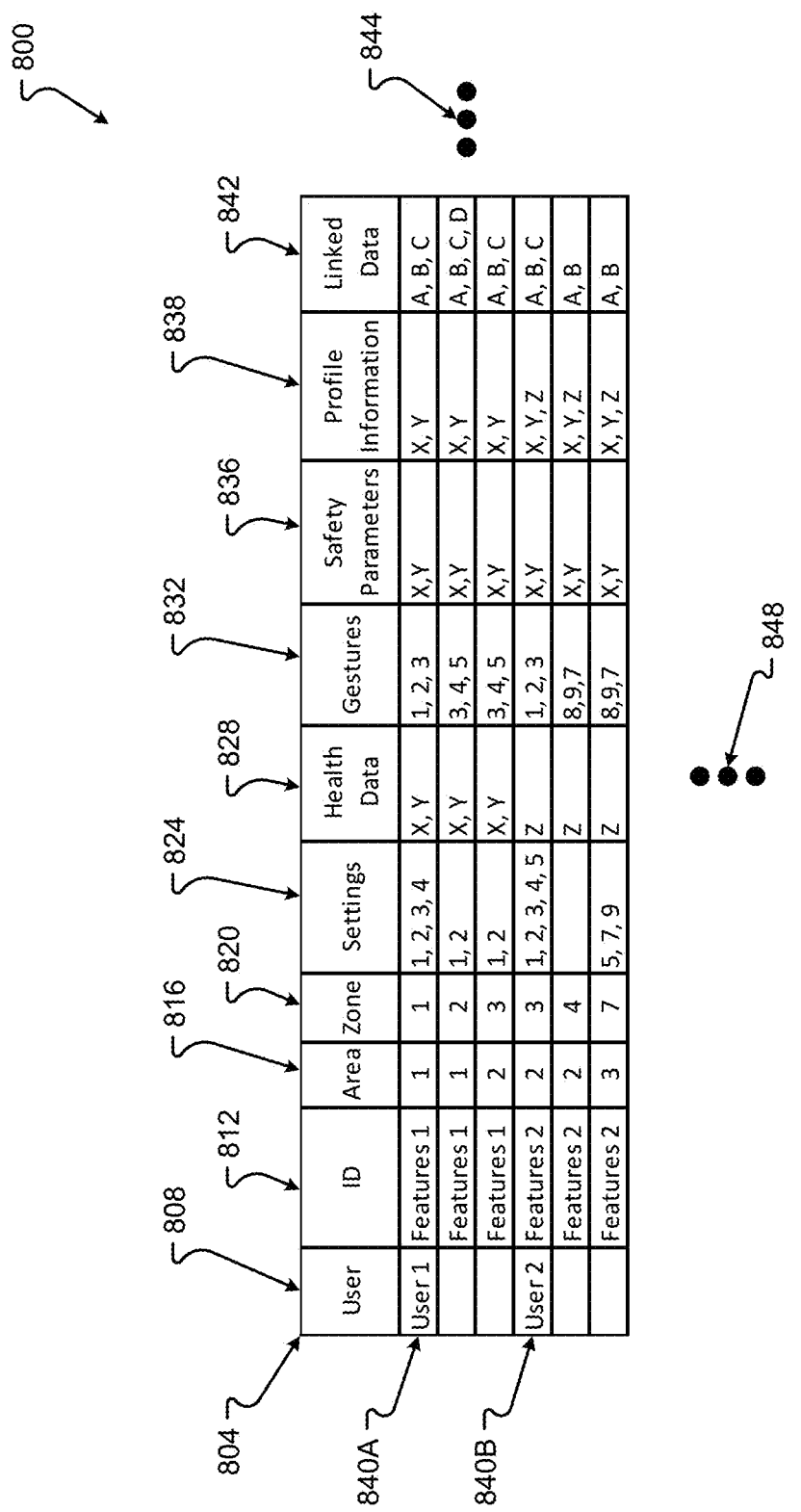

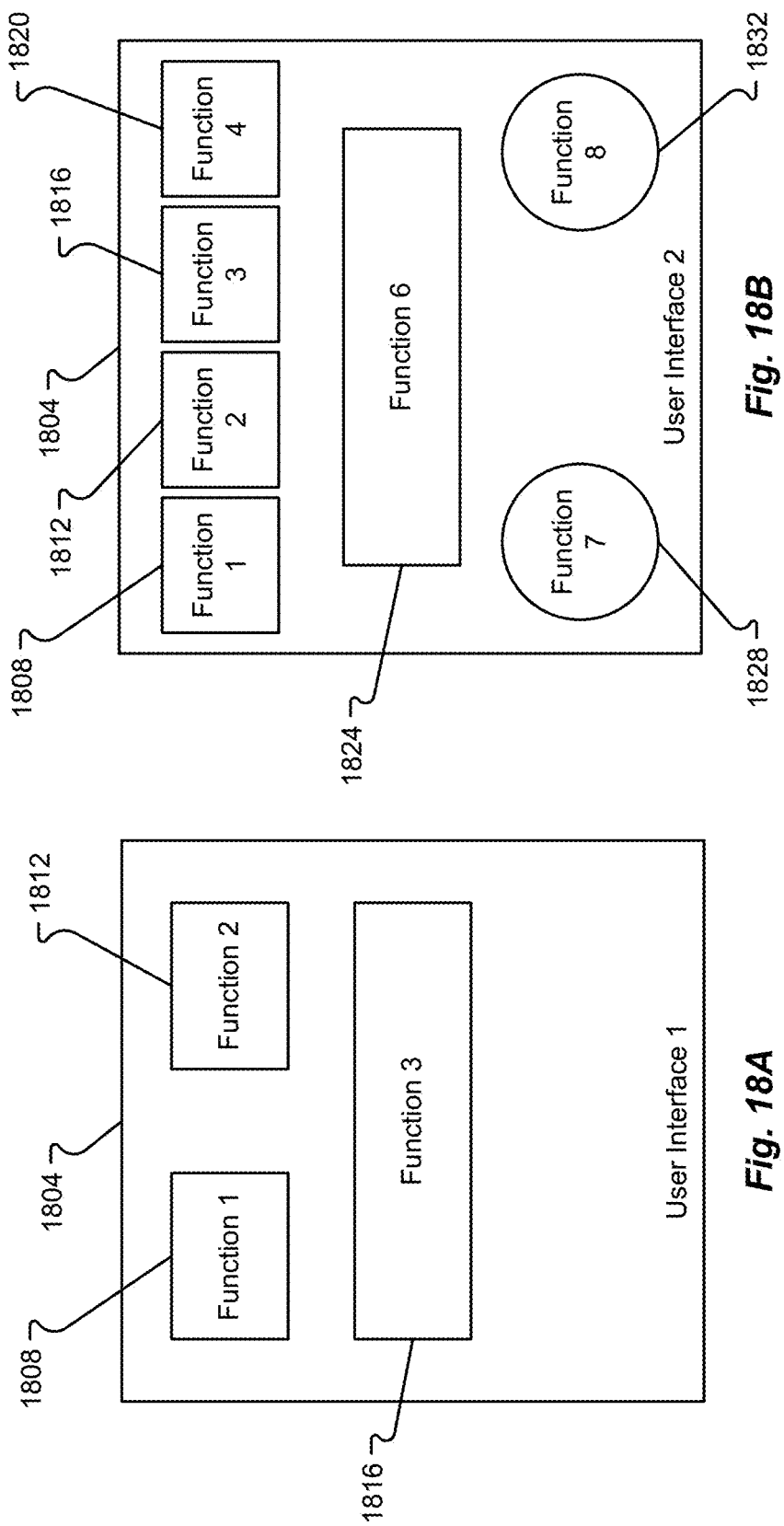

EXERCISE EQUIPMENT WITH IMPROVED USER INTERACTION

CROSS REFERENCE TO RELATED APPLICATIONS

The present application claims the benefits of and priority, under 35 U.S.C. §119, to U.S. Provisional Application Ser. No. 61/945,654, filed on Feb. 27, 2014, entitled "Treadmill;" the entire disclosure of the application listed above is hereby incorporated by reference, in its entirety, for all that it teaches and for all purposes.

BACKGROUND

Exercise has become very important to many people for maintaining their health and vitality. To maintain an exercise routine, many athletes turn to exercise machines, for example, a treadmill. A treadmill and/or other exercise machines are generally a mechanical piece of equipment that allows an athlete to conduct a physical activity while staying in the same place. For example, a treadmill can allow a user to walk or run while staying in the same place.

Most exercise machines have rudimentary interfaces, inputs, and outputs that allow a user to change the functionality of the machine. With a treadmill, for example, the user may control the speed of the belt that the user is running on or the inclination or angle at which the user is running. Further, treadmills today commonly have an interface that allows the user to select different types of exercise routines that will maximize the effectiveness of the exercise being conducted on the machine. The machine may also include several sensors for measuring the person's heart rate or other parameter and then process that information to give feedback to the user.

Unfortunately, these interfaces still remain somewhat rudimentary. Further, these interfaces also are harder to upgrade since they are static or fixed with the machine. Most exercise equipment leave the user with wanting more functionality from the interface portion of the exercise equipment.

SUMMARY

The embodiments presented herein provide for a treadmill or other piece of exercise equipment that includes an interface or connection to one or more devices of the user. While this connection(s) may be used for playing music or other media onto the already included interface of the exercise equipment, the present embodiments leverage the functionality of the various devices owned by users to provide a more rich experience while exercising and allow those devices to control the machine without the need of a static interface provided with the machine. An interface module can connect to the machine either as a separate item or as a built-in structure. The interface module can include a device interface that allows the user to both provide inputs into the machine but also to view outputs as the interface module can position the screen of a device in the view of the user.

Embodiment include a method for interacting with exercise equipment by a user, comprising: an exercise control system, including a processor, receiving a gesture from the user in three-dimensional space; the exercise control system identifying the received gesture; the exercise control system sending a verification of the received gesture to the user; the exercise control system determining if a confirmation is received in response to the verification; and if the confirmation is received, the exercise control system controlling a function associated with the received gesture.

An aspect of the above method, further comprising: if the confirmation is not received, the exercise control system determining if the received gesture should be completed; and if the received gesture should be completed, the exercise control system controlling the function associated with the received gesture.

An aspect of the above method, further comprising: if the received gesture should not be completed, the exercise control system determining if the verification should be resent; if the verification should be resent, the exercise control system again sending the verification; and if the verification should not be resent, receiving another gesture.

An aspect of the above method, wherein the verification is an audible message presented to the user.

An aspect of the above method, wherein the confirmation is a second gesture.

An aspect of the above method, wherein the confirmation is an audible confirmation.

An aspect of the above method, wherein the verification is a user interface message presented on a screen.

An aspect of the above method, wherein the confirmation is a selection of a user interface device on the screen.

An aspect of the above method, wherein the verification is a preview of the function associated with the received gesture.

An aspect of the above method, further comprising: the exercise control system receiving a denial of the verification; and based on the denial, the exercise control system not completing the function associated with the received gesture.

Embodiments include an exercise equipment comprising: a processor operable to execute two or more modules, the two or more modules comprising: a gesture recognition module operable to: receive a gesture from a user in a view of a camera; identify the received gesture; a verification module operable to: send a verification of the received gesture to the user; determine if a confirmation is received in response to the verification; and a function control module operable to, if the confirmation is received, control a function associated with the received gesture.

An aspect of the above exercise equipment, wherein the verification module further operable to, if the confirmation is not received, determine if the received gesture should be completed.

An aspect of the above exercise equipment, wherein the verification module further operable to: if the received gesture should not be completed, determine if the verification should be resent; if the verification should be resent, resend the verification.

An aspect of the above exercise equipment, wherein the verification is one of an audible message presented to the user, a user interface message presented on a screen, or a preview of the function associated with the received gesture.

An aspect of the above exercise equipment, wherein the confirmation is one of a second gesture, a selection of a user interface device on a screen, or an audible confirmation.

Embodiments include a non-transitory computer readable medium stored on a storage medium and having instructions that when executed by a processor cause the processor to perform a method, the instructions comprising: instructions to receive a gesture from a user in three-dimensional space associated with a view of a camera associated with a treadmill; instructions to identify the received gesture; instructions to send a verification of the received gesture to the user; instructions to determine if a confirmation is received in response to the verification; and if the confirmation is received, instructions to control a function associated with the received gesture.

An aspect of the above computer readable medium, further comprising, if the confirmation is not received, instructions to determine if the received gesture should be completed.

An aspect of the above computer readable medium, further comprising: if the received gesture should not be completed, instructions to determine if the verification should be resent; if the verification should be resent, instructions to resend the verification.

An aspect of the above computer readable medium, wherein the verification is one of an audible message presented to the user, a user interface message presented on a screen, or a preview of the function associated with the received gesture.

An aspect of the above computer readable medium, wherein the confirmation is one of a second gesture, a selection of a user interface device on a screen, or an audible confirmation.

The present disclosure can provide a number of advantages depending on the particular aspect, embodiment, and/or configuration. The embodiments presented herein provide the user with an easily configured and understood system for controlling the functions of the exercise equipment. The interfaces can also be changed based on the identity and characteristics of the user both automatically and manually, which again makes the system more user-friendly. These and other advantages will be apparent from the disclosure.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refer to any process or operation done without material human input when the process or operation is performed. However, a process or operation can be automatic, even though performance of the process or operation uses material or immaterial human input, if the input is received before the performance of the process or operation. Human input is deemed to be material if such input influences how the process or operation will be performed. Human input that consents to the performance of the process or operation is not deemed to be "material."

The term "bus" and variations thereof, as used herein, can refer to a subsystem that transfers information and/or data between various components. A bus generally refers to the collection communication hardware interface, interconnects, bus architecture, standard, and/or protocol defining the communication scheme for a communication system and/or communication network. A bus may also refer to a part of a communication hardware that interfaces the communication hardware with the interconnects that connect to other components of the corresponding communication network. The bus may be for a wired network, such as a physical bus, or wireless network, such as part of an antenna or hardware that couples the communication hardware with the antenna. A bus architecture supports a defined format in which information and/or data is arranged when sent and received through a communication network. A protocol may define the format and rules of communication of a bus architecture.

The terms "communication device," "smartphone," "device," "tablet," "mobile device," and variations thereof, as used herein, can be used interchangeably and may include any type of device capable of communicating with one or more of another device and/or across a communications network, via a communications protocol, and the like. Exemplary communication devices may include but are not limited to smartphones, handheld computers, laptops, netbooks, notebook computers, subnotebooks, tablet computers, scanners, portable gaming devices, phones, pagers, global positioning satellite (GPS) modules, portable music players, and other Internet-enabled and/or network-connected devices.

A "communication modality" can refer to any protocol- or standard defined or specific communication session or interaction, such as Voice-Over-Internet-Protocol ("VoIP"), cellular communications (e.g., IS-95, 1G, 2G, 3G, 3.5G, 4G, 4G/IMT-Advanced standards, 3GPP, WIMAX™, GSM, CDMA, CDMA2000, EDGE, 1xEVDO, iDEN, GPRS, HSPDA, TDMA, UMA, UMTS, ITU-R, and 5G), Bluetooth™, text or instant messaging (e.g., AIM, Blauk, eBuddy, Gadu-Gadu, IBM Lotus Sametime, ICQ, iMessage, IMVU, Lync, MXit, Paltalk, Skype, Tencent QQ, Windows Live Messenger™ or Microsoft Network (MSN) Messenger™, Wireclub, Xfire, and Yahoo! Messenger™), email, Twitter (e.g., tweeting), Digital Service Protocol (DSP), and the like.

The term "communication system" or "communication network" and variations thereof, as used herein, can refer to a collection of communication components capable of one or more of transmission, relay, interconnect, control, or otherwise manipulate information or data from at least one transmitter to at least one receiver. As such, the communication may include a range of systems supporting point-to-point or broadcasting of the information or data. A communication system may refer to the collection individual communication hardware as well as the interconnects associated with and connecting the individual communication hardware. Communication hardware may refer to dedicated communication hardware or may refer a processor coupled with a communication means (i.e., an antenna) and running software capable of using the communication means to send and/or receive a signal within the communication system. Interconnect refers some type of wired or wireless communication link that connects various components, such as communication hardware, within a communication system. A communication network may refer to a specific setup of a communication system with the collection of individual communication hardware and interconnects having some definable network topography. A communication network may include wired and/or wireless network having a pre-set to an ad hoc network structure.

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, read only memory (ROM), a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The terms display or console and variations thereof, as used herein, may be used interchangeably and can be any panel and/or area of exercise equipment disposed adjacent to an operator, user, and/or exerciser. Displays may include, but are not limited to, one or more control panel(s), instrument housing(s), indicator(s), gauge(s), meter(s), light(s), audio equipment, computer(s), screen(s), display(s), heads-up display HUD unit(s), and graphical user interface(s).

The term "module" as used herein refers to any known or later developed hardware, software, firmware, artificial intelligence, fuzzy logic, or combination of hardware and software that is capable of performing the functionality associated with that element.

The term "desktop" refers to a metaphor used to portray systems. A desktop is generally considered a "surface" that may include pictures, called icons, widgets, folders, etc. that can activate and/or show applications, windows, cabinets, files, folders, documents, and other graphical items. The icons are generally selectable to initiate a task through user interface interaction to allow a user to execute applications and/or conduct other operations.

The term "display" refers to a portion of a physical screen used to display the output of a computer to a user.

The term "displayed image" refers to an image produced on the display. A typical displayed image is a window or desktop. The displayed image may occupy all or a portion of the display.

The term "display orientation" refers to the way in which a rectangular display is oriented for viewing. The two most common types of display orientations are portrait and landscape. In landscape mode, the display is oriented such that the width of the display is greater than the height of the display (such as a 4:3 ratio, which is 4 units wide and 3 units tall, or a 16:9 ratio, which is 16 units wide and 9 units tall). Stated differently, the longer dimension of the display is oriented substantially horizontal in landscape mode while the shorter dimension of the display is oriented substantially vertical. In the portrait mode, by contrast, the display is oriented such that the width of the display is less than the height of the display. Stated differently, the shorter dimension of the display is oriented substantially horizontal in the portrait mode while the longer dimension of the display is oriented substantially vertical. A multi-screen display can have one composite display that encompasses all the screens. The composite display can have different display characteristics based on the various orientations of the device.

The term "electronic address" can refer to any contactable address, including a telephone number, instant message handle, e-mail address, Uniform Resource Locator ("URL"), Global Universal Identifier ("GUID"), Universal Resource Identifier ("URI"), Address of Record ("AOR"), electronic alias in a database, etc., combinations thereof.

The term "gesture" refers to a user action that expresses an intended idea, action, meaning, result, and/or outcome. The user action can include manipulating a device (e.g., opening or closing a device, changing a device orientation, moving a trackball or wheel, etc.), movement of a body part in relation to the device, movement of an implement or tool in relation to the device, audio inputs, etc. A gesture may be made on a device (such as on the screen) or with the device to interact with the device.

The term "gesture capture" refers to a sense or otherwise a detection of an instance and/or type of user gesture. The gesture capture can be received by sensors in three-dimensional space (i.e., the area of the environment that is in view of a sensor, for example, a camera). Further, the gesture capture can occur in one or more areas of a screen, for example, on a touch-sensitive display or a gesture capture region. A gesture region can be on the display, where it may be referred to as a touch sensitive display, or off the display, where it may be referred to as a gesture capture area.

The terms "infotainment" and "infotainment system" may be used interchangeably and can refer to the hardware/software products, data, content, information, and/or systems, which can be built into or added to exercise equipment to enhance user experience. Infotainment may provide media and/or multimedia content. An example is information-based media content or programming that also includes entertainment content.

The term "screen," "touch screen," "touchscreen," or "touch-sensitive display" refers to a physical structure that enables the user to interact with the computer by touching areas on the screen and provides information to a user through a display. The touch screen may sense user contact in a number of different ways, such as by a change in an electrical parameter (e.g., resistance or capacitance), acoustic wave variations, infrared radiation proximity detection, light variation detection, and the like. In a resistive touch screen, for example, normally separated conductive and resistive metallic layers in the screen pass an electrical current. When a user touches the screen, the two layers make contact in the contacted location, whereby a change in electrical field is noted and the coordinates of the contacted location calculated. In a capacitive touch screen, a capacitive layer stores electrical charge, which is discharged to the user upon contact with the touch screen, causing a decrease in the charge of the capacitive layer. The decrease is measured, and the contacted location coordinates determined. In a surface acoustic wave touch screen, an acoustic wave is transmitted through the screen, and the acoustic wave is disturbed by user contact. A receiving transducer detects the user contact instance and determines the contacted location coordinates.

The term "window" refers to a, typically rectangular, displayed image on at least part of a display that contains or provides content different from the rest of the screen. The window may obscure the desktop. The dimensions and orientation of the window may be configurable either by another module or by a user. When the window is expanded, the window can occupy substantially all of the display space on a screen or screens.

The terms "determine," "calculate," and "compute," and variations thereof, as used herein, are used interchangeably and include any type of methodology, process, mathematical operation, or technique.

It shall be understood that the term "means," as used herein, shall be given its broadest possible interpretation in accordance with 35 U.S.C., Section 72, Paragraph 6 or other applicable law. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "profile," as used herein, can refer to any data structure, data store, and/or database that includes one or more items of information associated with a exercise, a exercise system, a device (e.g., a mobile device, laptop, mobile phone, etc.), or a person.

The term "in communication with," as used herein, refers to any coupling, connection, or interaction using electrical signals to exchange information or data, using any system, hardware, software, protocol, or format, regardless of whether the exchange occurs wirelessly or over a wired connection.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

BRIEF DESCRIPTION OF THE DRAWINGS

FIG. 8A is a diagram of an embodiment of a data structure for storing information about a user of exercise equipment;

FIG. 18A is a graphical representation of an embodiment of a user interface for the exercise control system;

FIG. 18B is a graphical representation of another embodiment of a user interface for the exercise control system;

Figure 1B:
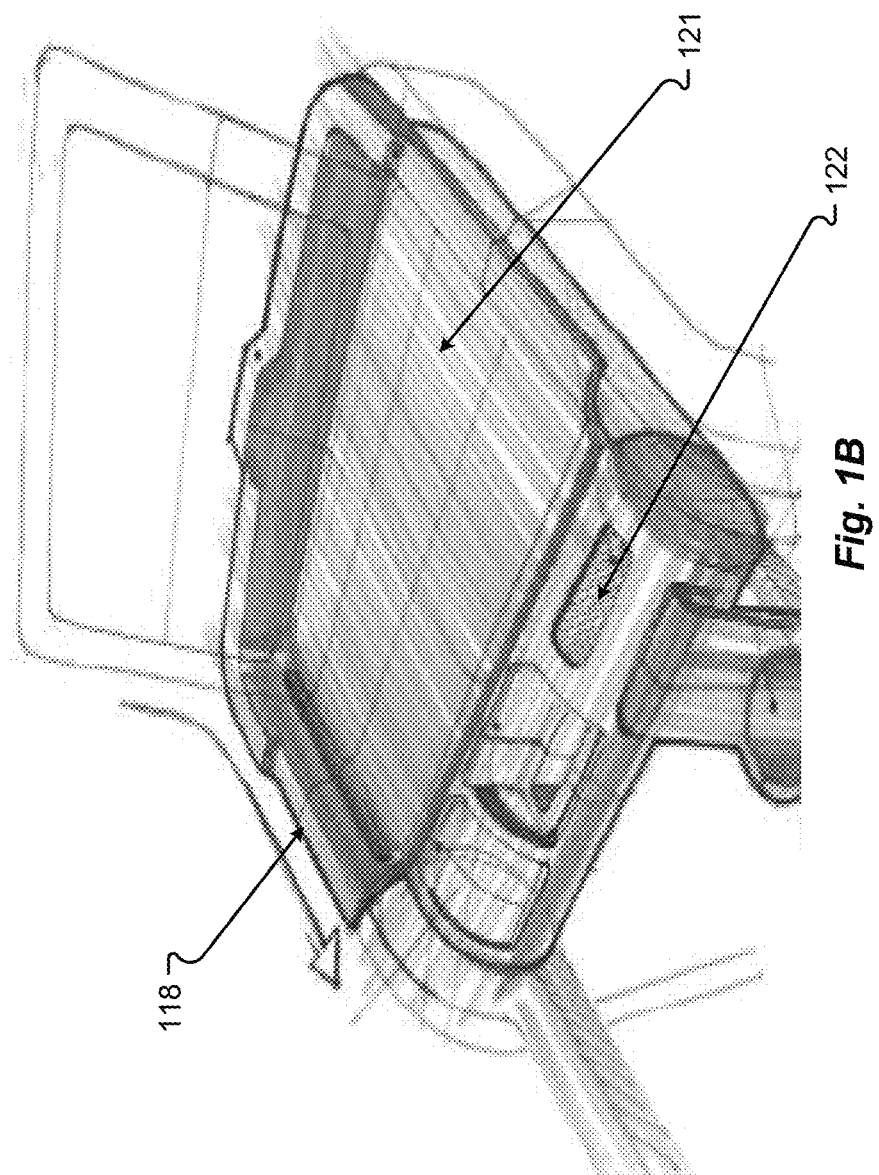
FIG. 1A through 1W depicts embodiments of an exercise operating environment and associated exercise equipment.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference letter or label.

DETAILED DESCRIPTION

Presented herein are embodiments of systems, devices, processes, data structures, user interfaces, etc. The embodiments may relate to a piece of exercise equipment, for example, a treadmill, and/or an exercise environment. The exercise environment can include systems associated with exercise equipment and devices or other systems in communication with the exercise equipment. Furthermore, the systems can relate to communications systems and/or devices and may be capable of communicating with other devices and/or to an individual or group of individuals. Further, the systems can receive user input in unique ways. The overall design and functionality of the systems provide for an enhanced user experience while making exercise more enjoyable and more efficient. As described herein, the exercise equipment systems may be electrical, mechanical, electro-mechanical, software-based, and/or combinations thereof.

An exercise environment 100 that may contain exercise equipment is shown in FIG. 1A. The exercise equipment 102 is shown as a treadmill but can be any type of exercise equipment, e.g., exercise bike, stair climber, rowing machine, etc. The treadmill 102 may include a platform 104 that the user runs on. This platform has a belt 108 that extends between two rollers, generally positioned inside the treadmill at areas 116a and 116b. The belt is tensioned by the two rollers and has a frictionless or other type of material on the back of the belt that rides along the platform 104. The backing of the belt 108 allows the user to run along the platform or on top of the belt surface without causing the belt 108 to stick or adhere temporarily to the platform 104. The interaction of the belt 108 and the platform 104 allows the user to run in place.

The treadmill generally has a motor connected to one or more of the rollers. The motor, not shown, can control the speed of the belt 108 and can cause the belt to rotate around the rollers and platform 104. The treadmill 102 may also include a platform or railing 118 that can hold the user interface portion of the treadmill 102. Here, a user 120 is shown running along the treadmill 102. While the embodiments described herein will be described with the treadmill 102, the interfaces and other embodiments are not limited to use with just this type of exercise equipment. The interfaces may be used with other types of exercise equipment, as will be understood by one skilled in the art.

Figure 1D:
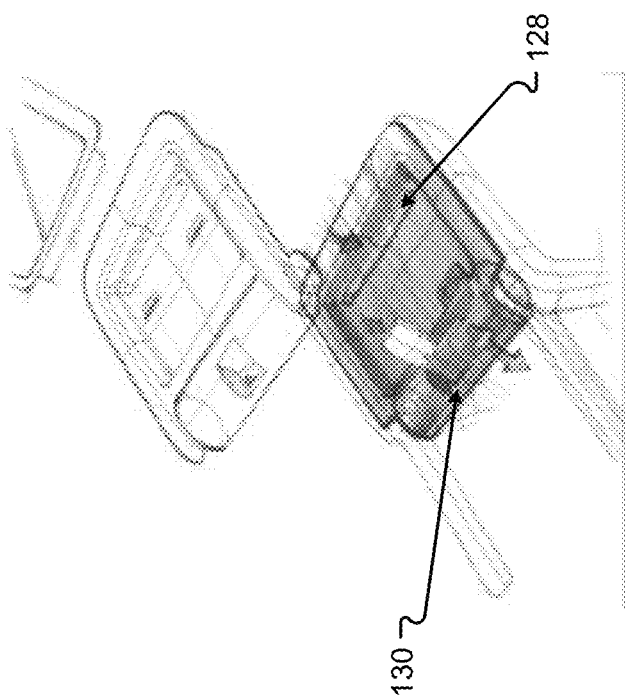
Figure 1C:
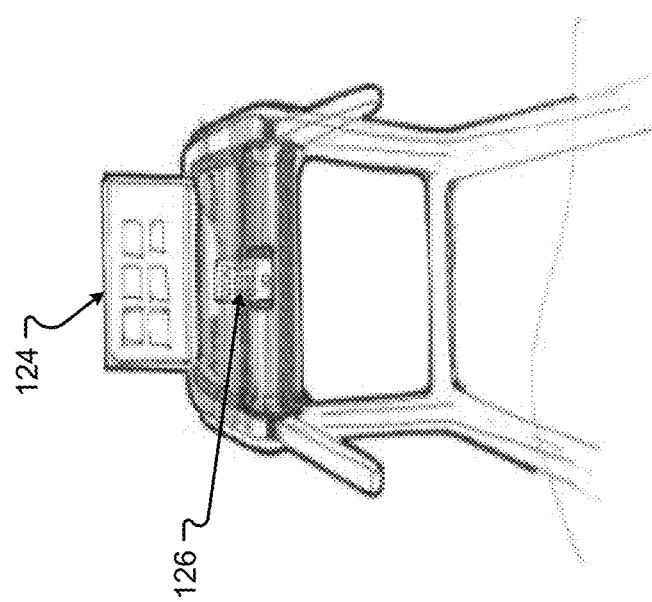
Figure 1F:
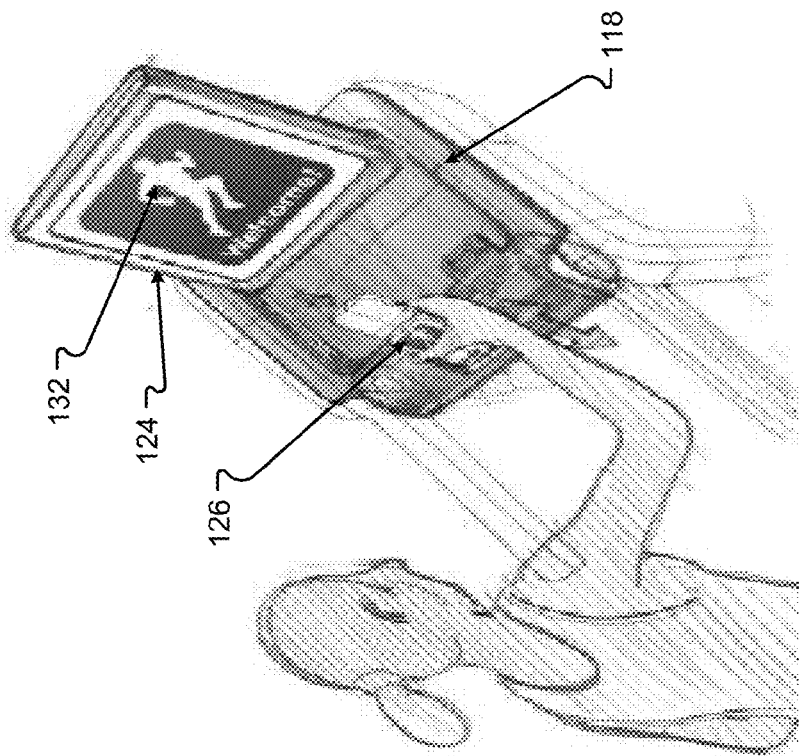
Figure 1E:
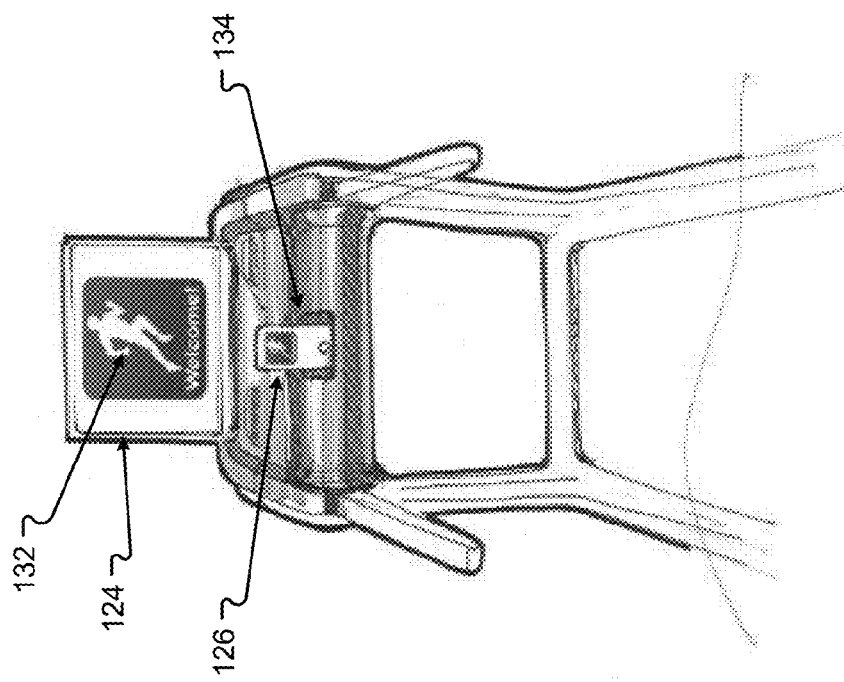
Figure 1J:
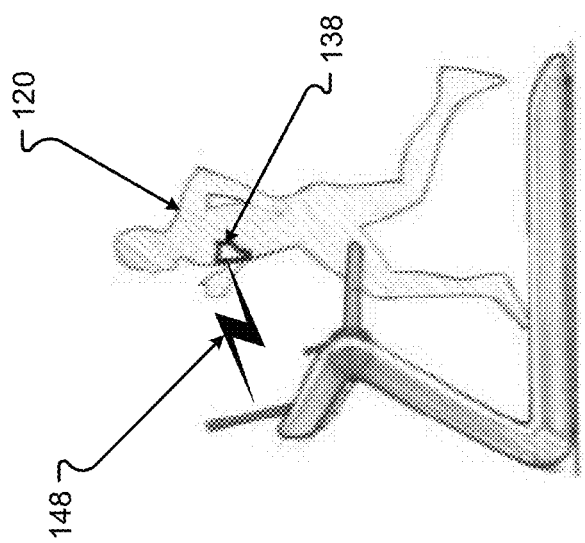
Figure 1I:
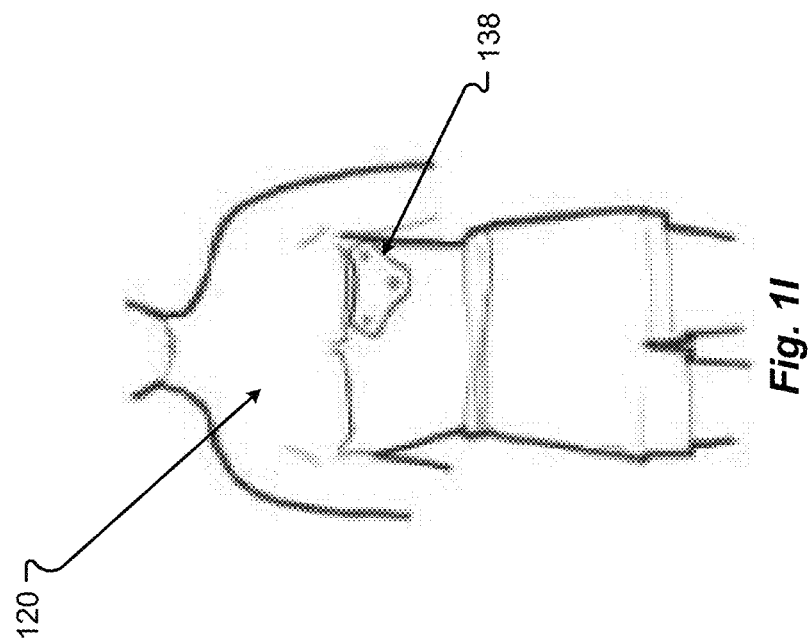
Figure 1N:
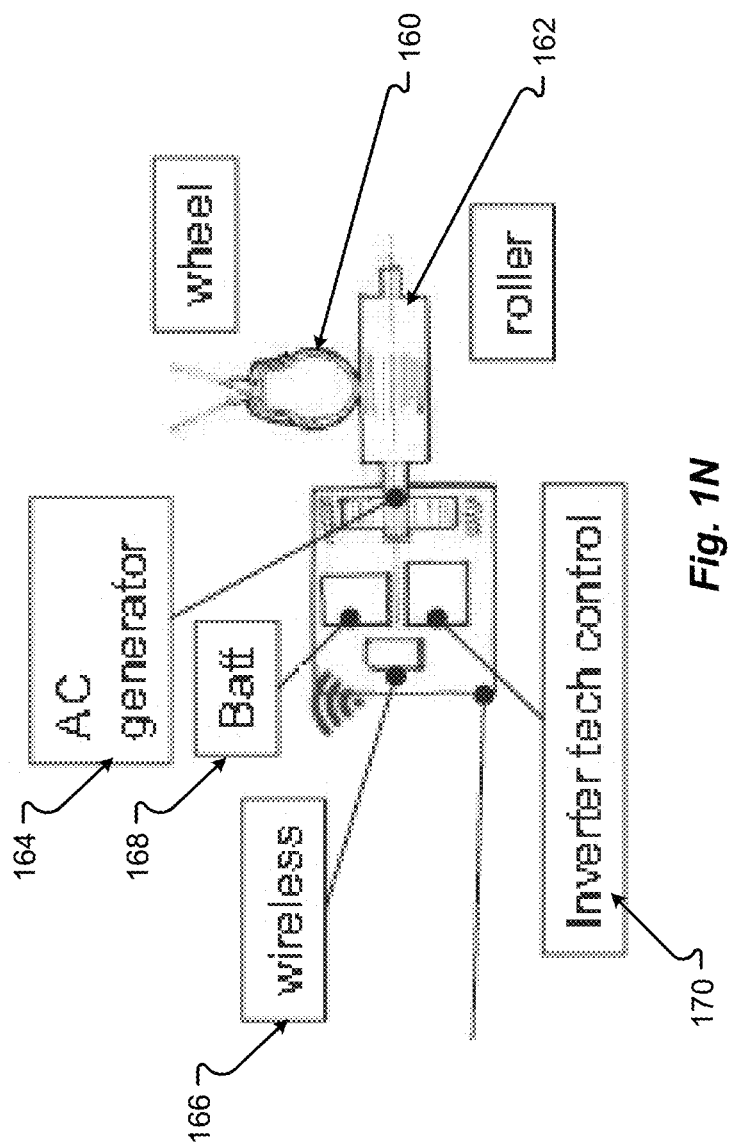
Figure 1S:
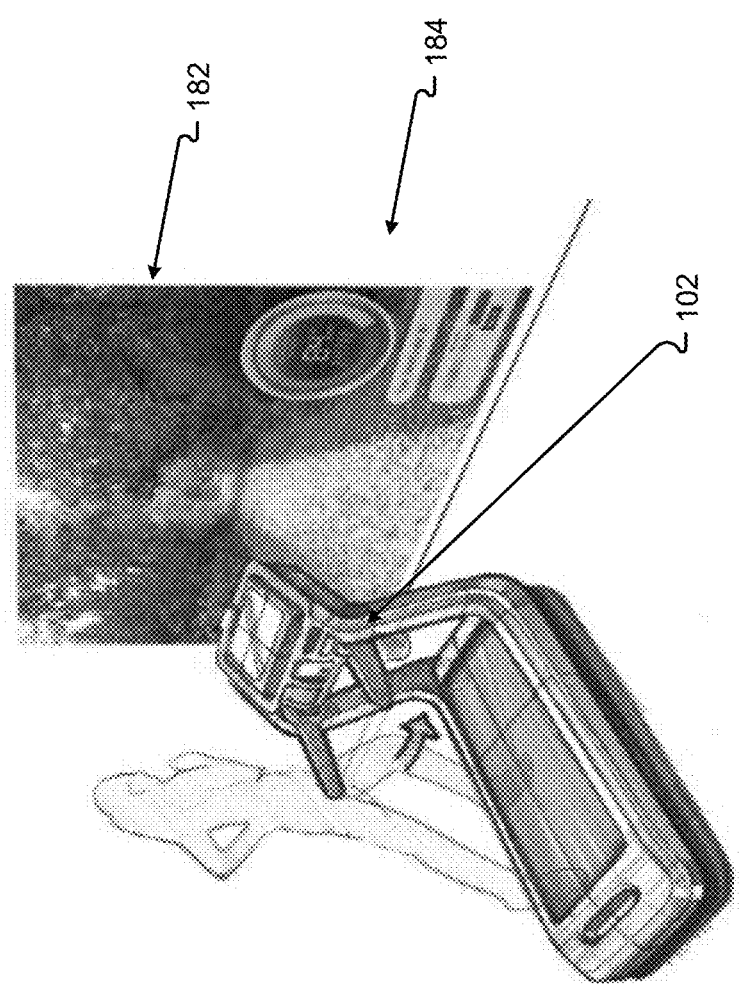
Figure 1U:
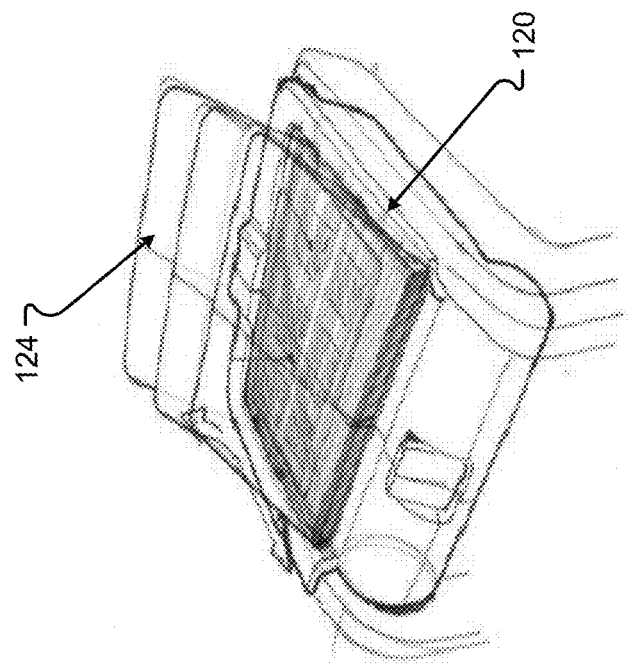
Figure 1T:
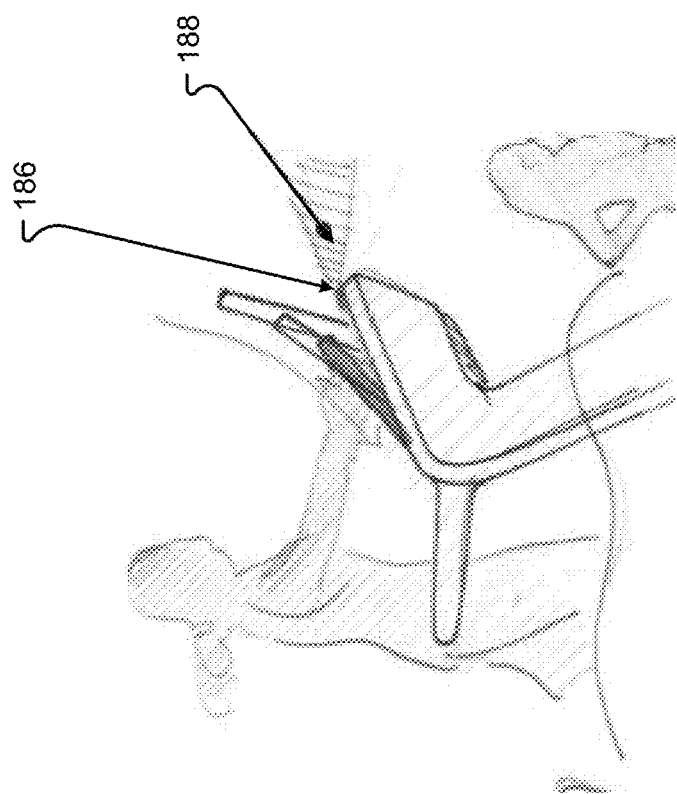
Figure 1V:
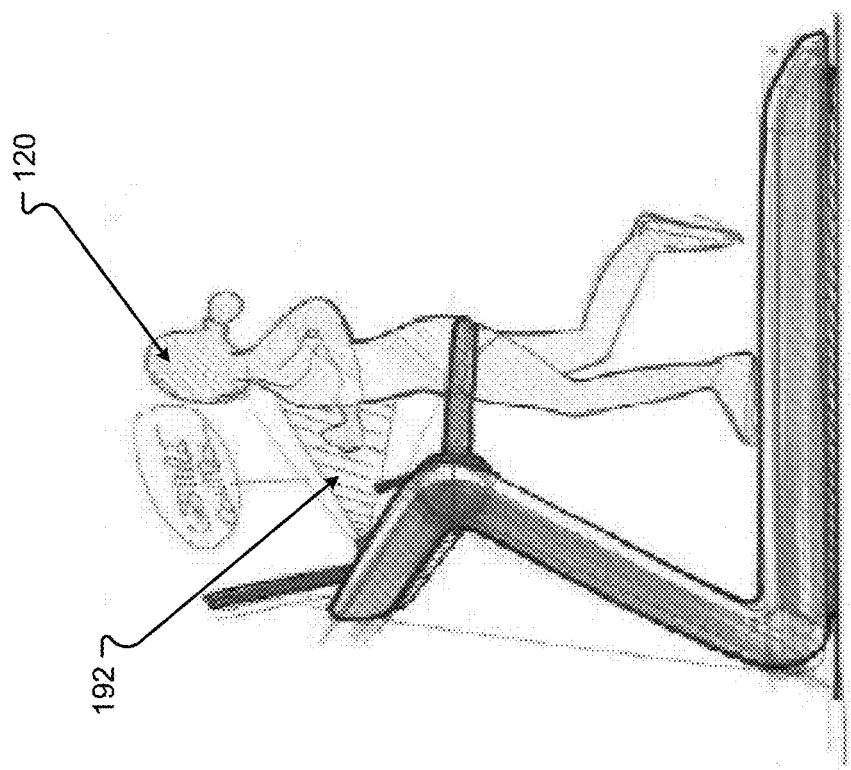
Figure 1W:
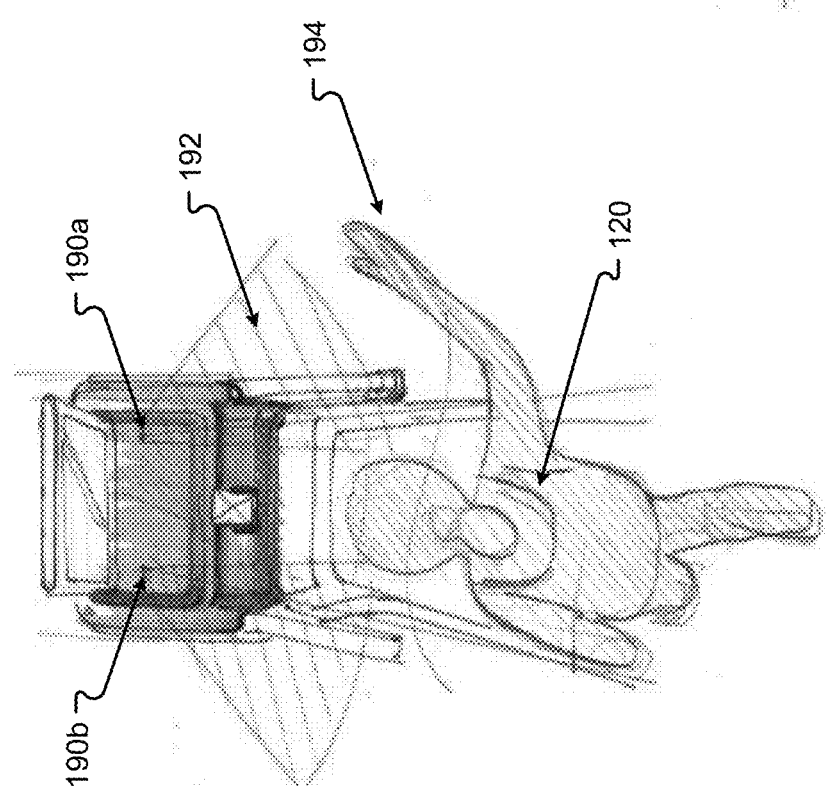

Different configurations and/or embodiments of the treadmill may be as shown in FIGS. 1B through 1W. An embodiment of an interface module 118 may be as shown in FIGS. 1B, 1C, and 1D. The interface module 118 may have a configuration that allows the interface module 118 to be temporarily connected or permanently affixed to the treadmill 102. For example, the interface module 118 may be able to physically connect to the railing 114 of the treadmill 102. In some situations, the interface module 118 may be removable or replaceable and thus not be permanently adhered or affixed to the railing 114.

The interface module 118 may include a tray 121 that includes an indention within the interface module 118 to hold different items, such as books or other types of items belonging to the athlete using the treadmill 102. Further, the treadmill may include one or more interface connections or ports 128 and 130 that can hold and electrically connect a device or devices 124, 126 to the interface module 118. These ports 128 and 130 may physically hold the device 124, 126, such that the devices 124, 126 have their user interface facing the user while the athlete is exercising on the treadmill 102. Further, these ports 128 and 130 may also have a configuration to electrically connect the devices 124, 126 to the motor controls or other equipment of the treadmill 102. Thus, the interface module 118 can have electrical connections between the treadmill 102 and any devices 124, 126 that are inserted or are integrated with the interface module 118.

An interface module 118 may also include one or more types of input/output devices. For example, the interface module 118 can include a microphone and speaker 122 integrated within the interface module 118 to allow the user to provide voice commands or to provide audio output to the user. The audio output may be generated from the devices 124, 126 and provided to the user through these larger, more robust speakers. An interface module 118 may also have other types of systems, devices, input/output electrical connections, cavities, or other configurations. These other configurations may be as explained in the pages that follow hereinafter.

A docking station for a mobile device 126 and/or tablet 125 may be as shown in FIGS. 1E and 1F. The docking station may be a port 134 containing a physical configuration for holding a device 124, 126. The port 134 may be formed within a part of the interface module 118. The port 134 may include some sort of configuration to physically hold the device plus any electrical connections to allow the device 124, 126 to communicate with the treadmill 102 or other systems. The interface module 118 may also include a port for holding a tablet 124. The configuration of the ports may allow the user to view a user interface 132 from either the tablet 124 or the mobile device 126. The device 126 and tablet 124 may be removable from the ports, but, when connected, may allow the device 124 and tablet 126 to communicate with the treadmill 102 or other devices, control those devices, provide input and output, and conduct other various tasks.

An embodiment of a system 136 for holding, charging, and communicating with a wearable device 138 (also referred to as a "wearable") may be as shown in FIGS. 1G through 1J. A container 144 may allow a wearable 138 to be placed within the container 144 in a configured slot 146. The configured slot 146 may include electrical connections to charge the wearable 138 while being placed within the system 136. The wearable 138 may also include one or more attachable electrode sensors 140. These attachable electrode sensors 140 may be adhered or mechanically affixed to the rechargeable transmitter 142 to form the wearable 138. Thus, the two different units or components (140 and 142) form the wearable 138, which may be placed on a user 120 to provide sensory telemetry to the mobile devices 124, 126.

The system 136 may be integrated within the interface module 118. The integration allows the user 120 to keep the wearable 138 in the same spot as the exercise equipment without needing to move it or store it in another location. Further, the wearable device 138, with the attachable electrode sensors 140, allows the user to maintain a more hygienic wearable device 138 without the need of persistent washing of the wearable 138. The wearable 138, thus, can be a device that need not be waterproof or at least only water resistant, such that the wearable device 138 can be made more inexpensively.

FIGS. 1I and 1J show the wearable 138 in use. Herein, the attachable electrode sensors 140 may be attached to the wearable transmitter 142. This wearable 138 may then be affixed or held next to the skin of a user 120. As shown in FIG. 1I, the wearable 138 may be positioned to provide information about the heart rate of a user 120. The wearable 138 may be adhered to or positioned and held near the chest or over the heart of the user 120. When exercising, as shown in FIG. 1J, the wearable 138 may sense and/or record health telemetry and transmit that information wirelessly over a wireless link 148 to the devices 124, 126. Thus, the wearable 138 may provide the telemetry information to the devices 124, 126 to provide feedback to the user 120 about their exercise routine.

The treadmill 102 may also provide for the use of a road bike or other type of bike for exercise, as shown in FIGS. 1K through 1N. In such situations, a mechanical coupling 150 may be permanently or temporarily adhered to a back portion 152 of the treadmill. This coupling 150 can be affixed at a point 158 on the back portion 152 of the platform 104. One or more mechanical connections 156 may physically attach or couple to the bike 154. This coupling 156 may allow the bike to spin its back wheel but maintain it vertically on the treadmill 102. As such, the user can pedal the bike along the treadmill track that is normally used for running but not configured to allow the user to ride the bicycle 154.

As shown in FIG. 1N, the coupling 150 can include various systems, modules, or components, such as a roller 162 that comes in contact with the wheel 160 of the bike 154. The roller 162 can change the resistance applied to the back wheel 160 to provide different exercise intensities to the user. The roller 162 may be mechanically coupled and/or electrically connected to an alternating current (AC) generator 164, a wireless transmitter 166, a battery 168, and an inverter control 150. These various systems 162-150 may receive or send signals between the coupling 150 and the devices 124, 126 to control the resistance, speed, or other variables used for the coupling 150. Further, these different systems 162-150 may control the roller speed or resistance based on input received through the wireless transmitter 166.

The treadmill 102 and interface module 118 may include an input/output device which may include an earpiece, with a microphone, as shown in FIGS. 1O through 1R. A slot or port 172 may physically hold and recharge a wireless device 176. The wireless device 176 may include an earpiece 176, with a speaker 178 and a microphone 180. As such, the user may receive audio inputs into the earpiece 176, when wearing that earpiece 176, as shown in FIG. 1R. Further, the user 120 may provide speech or vocal commands into the microphone 180, which may be used with speech recognition software to allow the user to provide commands to the devices 126, 124. When not in use, the device 176 may be placed within the port 174 as shown in FIG. 1Q. There may be an electrical contact between the device 176 and the interface module 118 that allows the device 176 to be recharged while in the port 174.

Figure 15:
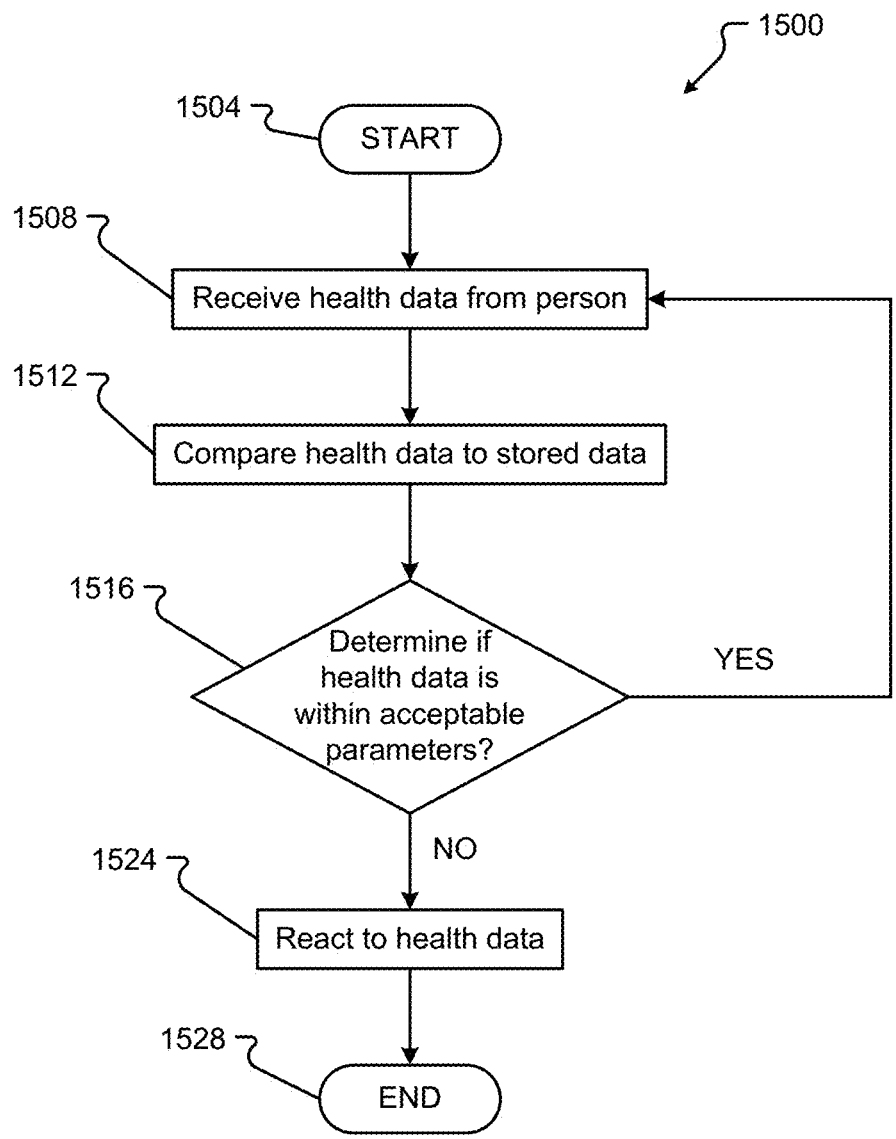
FIG. 15 is a flow or process diagram of a method for reacting to health data associated with a user.

A projection feature may be as shown in FIGS. 1S through 1U. The user may be able to switch the display from one of the devices 126, 124 to an outward projector 186. The projector 186 may project a visual display 182 onto a surface 184, as shown in FIG. 15. The projection 188 may come from a lens and/or projection device 186 that is mounted on the interface module 118.

The user may be able to change the configuration of the interface module 118 to lay the device 124 within the tray 121 such that the user has a better viewing angle of the display 182 projected on the surface 184. The projection 188 allows the user to view better the telemetry data and/or to provide a view of a running path that allows the user to have a more interactive experience on the treadmill, as shown in FIG. 1S.

A series of embedded cameras may allow for the user to provide gestures into the devices 124, 126, as shown in FIGS. 1V and 1W The interface module 118 may include one or more cameras 190A, 190B, etc. These cameras 190 may have a viewing field 192 that allows the user 120 to make three-dimensional gestures, with their hands, within the viewing field 192. The gesture 194 may be within three-dimensional space but may have a certain hand configuration or movement that allows the user to provide gestures to control the devices 126, 124 or the systems of the treadmill 102. These gestures may be recognized using a video technology that can determine both the type of gesture with the hand and any movement of the arm or other features of the user.

Figure 2:
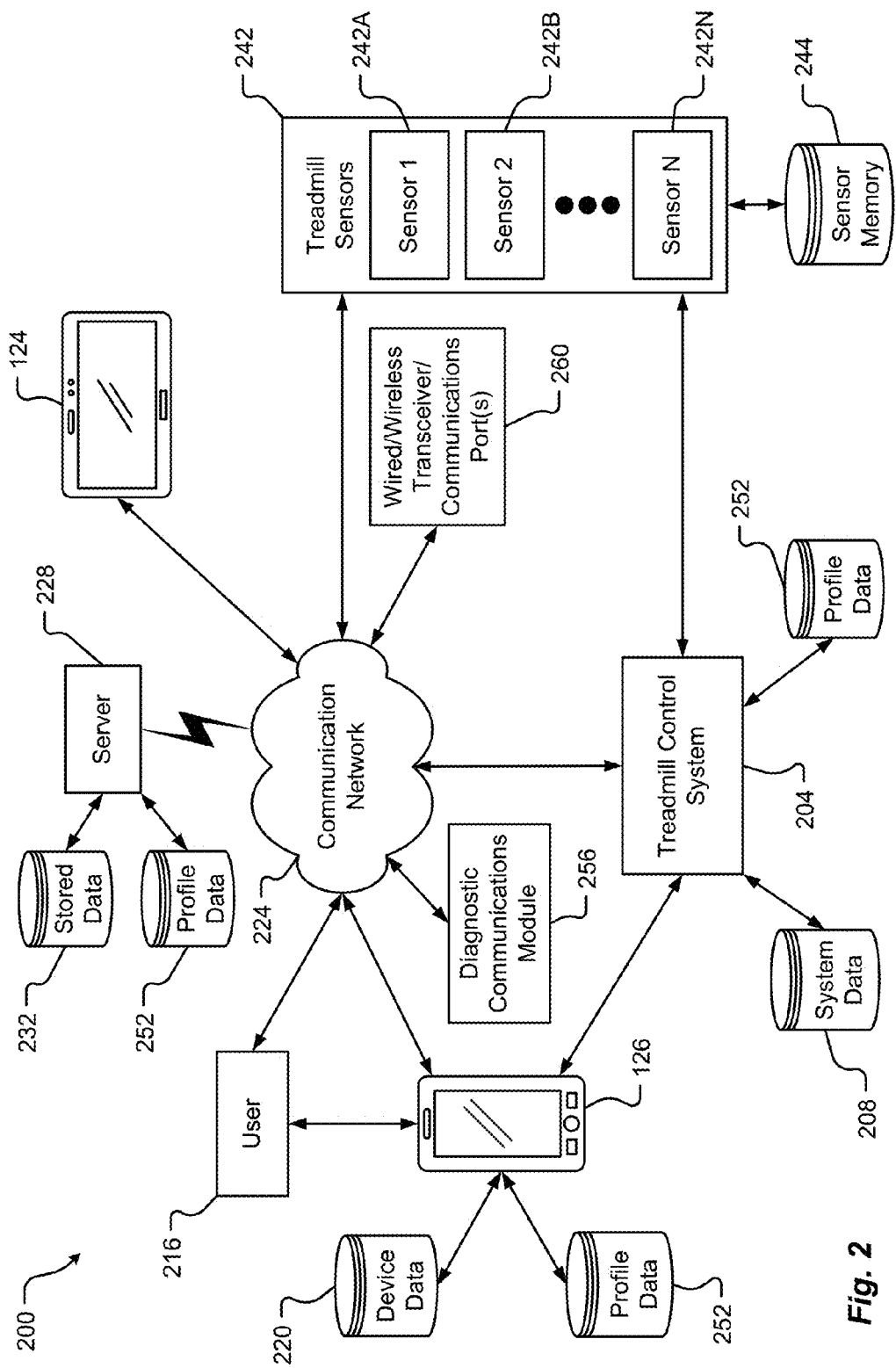
FIG. 2 is a block diagram of an embodiment of an exercise system.

An embodiment of exercise system 200 is shown in FIG. 2. The exercise system 200 may comprise hardware and/or software that conduct various operations for or with the treadmill 102. The operations can include, but are not limited to, providing information to the user 216, receiving input from the user 216, and controlling the functions or operation of the treadmill 102, etc. The exercise system 200 can include an exercise control system 204. The exercise control system 204 can be any type of computing system operable to conduct the operations as described herein. An example of an exercise control system 204 may be as described in conjunction with FIG. 3.

The exercise control system 204 may interact with a memory or storage system 208 that stores system data. System data 208 may be any type of data needed for the exercise control system 204 to control effectively the treadmill 102. The system data 208 can represent any type of database or other storage system. Thus, the system data 208 can be a flat file data system, an object-oriented data system, or some other data system that may interface with the exercise control system 204.

The exercise control system 204 may communicate with a device or user interface for device 124, 126. The user interface 126, 124 may be operable to receive user input either through touch input, on one or more user interface buttons, via voice command, via one or more image sensors, or through a graphical user interface that may include a gesture capture region, as described in conjunction with the other figures provided herein. Further, the symbol 126, 124 can represent a device that is located or associated with the treadmill 102. The device 126, 124 can be a mobile device, including, but not limited to, a mobile telephone, a tablet computer, a mobile computer, or other type of computing system or device that is either permanently located in or temporarily associated with, but not necessarily connected to, the treadmill 102. Thus, the exercise control system 204 can interface with the device 126, 124 and leverage the device's computing capability to provide one or more of the features or functions as described herein.

The device or user interface 126, 124 can receive input or provide information to a user 120. The user 120 may thus interact with the exercise control system 204 through the interface or device 126, 124. Further, the device 126, 124 may include or have access to device data 220 and/or profile data 252. The device data 220 can be any type of data that is used in conjunction with the device 126, 124 including, but not limited to, multimedia data, preferences data, device identification information, or other types of data. The profile data 252 can be any type of data associated with at least one user 120 including, but in no way limited to, bioinformatics, medical information, exercise history, personal information (e.g., home physical address, business physical address, contact addresses, likes, dislikes, hobbies, size, weight, occupation, business contacts—including physical and/or electronic addresses, personal contacts—including physical and/or electronic addresses, family members, and personal information related thereto, etc.), other user characteristics, advertising information, user settings and feature preferences, associated exercise preferences, communication preferences, historical information (e.g., including historical, current, and/or future exercise routines or competitions), Internet browsing history, or other types of data. In any event, the data may be stored as device data 220 and/or profile data 252 in a storage system similar to that described in conjunction with FIGS. 8A through 8D.

As an example, the profile data 252 may include one or more user profiles. User profiles may be generated based on data gathered from one or more of exercise preferences (e.g., equipment settings, user interface settings and/or configurations, and the like), recorded settings, geographic location information (e.g., provided by a satellite positioning system (e.g., GPS), Wi-Fi hotspot, etc.), mobile device information (such as mobile device electronic addresses, Internet browsing history and content, application store selections, user settings and enabled and disabled features, and the like), private information (such as user information from a social network, user presence information, user business account, and the like), secure data, biometric information, audio information from on board microphones, video information from on board cameras, Internet browsing history and browsed content using an on board computer and/or the local area network enabled by the treadmill 102, geographic location information, and the like.

The profile data 252 may include one or more user accounts. User accounts may include access and permissions to one or more settings and/or feature preferences associated with the treadmill 102, communications, infotainment, content, etc. In one example, a user account may allow access to certain settings for a particular user, while another user account may deny access to the settings for another user, and vice versa. The access controlled by the user account may be based on at least one of a user account priority, role, permission, age, family status, a group priority (e.g., the user account priority of one or more users, etc.), a group age (e.g., the average age of users in the group, a minimum age of the users in the group, a maximum age of the users in the group, and/or combinations thereof, etc.).

For example, a user 120 may be allowed to purchase applications (e.g., software, etc.) for the treadmill 102 and/or a device associated with the treadmill 102 based on information associated with the user account. This user account information may include a preferred payment method, permissions, and/or other account information. As provided herein, the user account information may be part of the user profile and/or other data stored in the profile data 252.

The exercise control system 204 may also communicate with or through a communication network 224. The communication network 224 can represent any type of wireless and/or wired communication system that may be included within the treadmill 102 or operable to communicate outside the treadmill 102. Thus, the communication network 224 can include a local area communication capability and a wide area communication capability. For example, the communication network 224 can include a Bluetooth® wireless system, an 802.7x (e.g., 802.7G/802.7N/802.7AC, or the like, wireless system), a bus, an Ethernet network within the treadmill 102, or other types of communication networks that may function with or be associated with the treadmill 102. Further, the communication network 224 can also include wide area communication capabilities, including one or more of, but not limited to, a cellular communication capability, satellite telephone communication capability, a wireless wide area network communication capability, or other types of communication capabilities that allow for the exercise control system 204 to communicate outside the treadmill 102.

The exercise control system 204 may communicate through the communication network 224 to a server 228 that may be located in a facility that is not within physical proximity to the treadmill 102. Thus, the server 228 may represent a cloud computing system or cloud storage that allows the exercise control system 204 to either gain access to further computing capabilities or to storage at a location outside of the treadmill 102. The server 228 can include a computer processor and memory and be similar to any computing system as understood to one skilled in the art.

Further, the server 228 may be associated with stored data 232. The stored data 232 may be stored in any system or by any method, as described in conjunction with system data 208, device data 220, and/or profile data 252. The stored data 232 can include information that may be associated with one or more users 120 or associated with one or more exercises. The stored data 232, being stored in a cloud or in a distant facility, may be exchanged among exercise equipment 102 or may be used by a user 120 in different locations or with different exercise equipment 102. Additionally or alternatively, the server may be associated with profile data 252 as provided herein. It is anticipated that the profile data 252 may be accessed across the communication network 224 by one or more components of the system 200. Similar to the stored data 232, the profile data 252, being stored in a cloud or in a distant facility, may be exchanged among exercise equipment 102 or may be used by a user 120 in different locations or with different exercise equipment 102.

The exercise control system 204 may also communicate with one or more sensors 242, which are either associated with the treadmill 102 or communicate with the treadmill 102. Exercise sensors 242 may include one or more sensors for providing information to the exercise control system 204 that determine or provide information about the exercise environment 100 in which the treadmill 102 is operating. Embodiments of these sensors may be as described in conjunction with FIG. 5. The exercise control system 204 may also perform signal processing of signals received from one or more sensors 242. Such signal processing may include estimation of a measured parameter from a single sensor and/or the estimation, blending, or fusion of a measured state parameter from multiple sensors. Signal processing of such sensor signal measurements may comprise stochastic signal processing, adaptive signal processing, and/or other signal processing techniques known to those skilled in the art.

The various sensors 242 may include one or more sensor memory 244. Embodiments of the sensor memory 244 may be configured to store data collected by the sensors 242. For example, a temperature sensor may collect temperature data associated with a treadmill 102, a user 120, and/or environment, over time. The temperature data may be collected incrementally, in response to a condition, or at specific time periods. In this example, as the temperature data is collected, it may be stored in the sensor memory 244. In some cases, the data may be stored along with an identification of the sensor and a collection time associated with the data. Among other things, this stored data may include multiple data points and may be used to track changes in sensor measurements over time. As can be appreciated, the sensor memory 244 can represent any type of database or other storage system.

The diagnostic communications module 256 may be configured to receive and transmit diagnostic signals and information associated with the treadmill 102. Examples of diagnostics signals and information may include, but is in no way limited to, exercise system warnings, sensor data, exercise component status, service information, user and/or component health, maintenance alerts, recall notifications, predictive analysis, and the like. Embodiments of the diagnostic communications module 256 may handle warning/ error signals in a predetermined manner. The signals, for instance, can be presented to one or more of a third party, user 120, exercise control system 204, and a service provider (e.g., manufacturer, repair facility, etc.).

Optionally, the diagnostic communications module 256 may be utilized by a third party (i.e., a party other than the user 120, etc.) in communicating diagnostic information. For instance, a manufacturer may send a signal to a treadmill 102 to determine a status associated with one or more components associated with the treadmill 102. In response to receiving the signal, the diagnostic communications module 256 may communicate with the exercise control system 204 to initiate a diagnostic status check. Once the diagnostic status check is performed, the information may be sent via the diagnostic communications module 256 to the manufacturer. This example may be especially useful in determining whether a component recall should be issued based on the status check responses returned from a certain number of exercise equipment.

Wired/wireless transceiver/communications ports 260 may be included. The wired/wireless transceiver/communications ports 260 may be included to support communications over wired networks or links, for example with other communication devices, server devices, and/or peripheral devices. Examples of wired/wireless transceiver/communications ports 260 include Ethernet ports, Universal Serial Bus (USB) ports, Institute of Electrical and Electronics Engineers (IEEE) 1594, or other interface ports.

Figure 3:
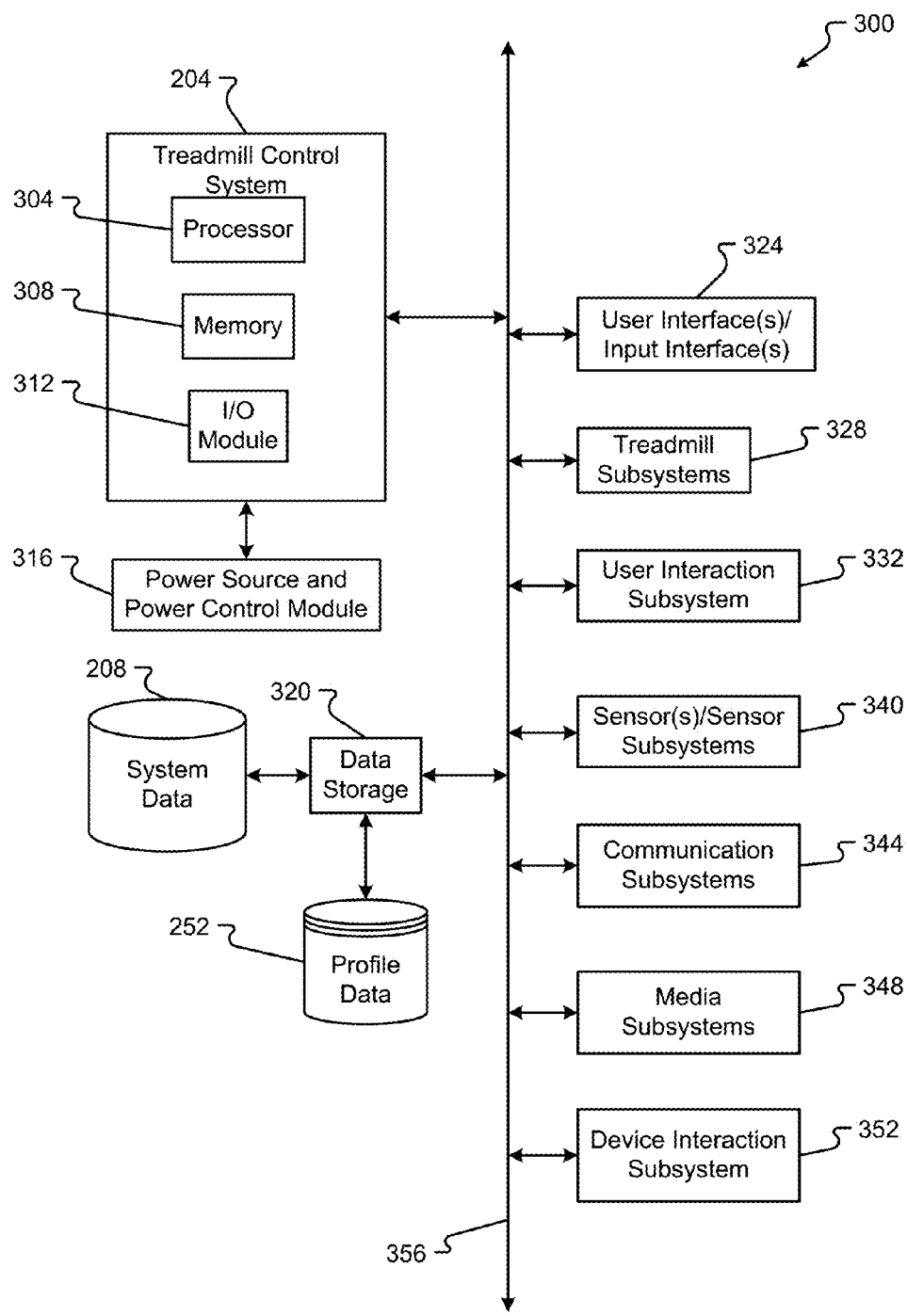
FIG. 3 is a block diagram of an embodiment of an exercise control system environment.

An embodiment of an exercise control system 300 including a treadmill control system 204 may be as shown in FIG. 3. Beyond the treadmill control system 204, the exercise control system 300 can include one or more of, but is not limited to, a power source and/or power control module 316, a data storage module 320, user interface(s)/input interface(s) 324, treadmill subsystems 328, user interaction subsystems 332, sensor(s) and/or sensor subsystems 340, communication subsystems 344, media subsystems 348, and/or device interaction subsystems 352. The subsystems, modules, components, etc. 316-352 may include hardware, software, firmware, computer readable media, displays, input devices, output devices, etc. or combinations thereof. The system, subsystems, modules, components, etc. 204, 316-352 may communicate over a network or bus 356. This communication bus 356 may be bidirectional and perform data communications using any known or future-developed standard or protocol.

The treadmill control system 204 can include a processor 304, memory 308, and/or an input/output (I/O) module 312. Thus, the treadmill control system 204 may be a computer system, which can comprise hardware elements that may be electrically coupled. The hardware elements may include one or more central processing units (CPUs) 304, one or more components of the I/O module 312 including input devices (e.g., a mouse, a keyboard, etc.), and/or one or more output devices (e.g., a display device, a printer, etc.).

The processor 304 may comprise a general purpose programmable processor or controller for executing application programming or instructions. The processor 304 may, optionally, include multiple processor cores, and/or implement multiple virtual processors. Additionally or alternatively, the processor 304 may include multiple physical processors. As a particular example, the processor 304 may comprise a specially configured application specific integrated circuit (ASIC) or other integrated circuit, a digital signal processor, a controller, a hardwired electronic or logic circuit, a programmable logic device or gate array, a special purpose computer, or the like. The processor 304 generally functions to run programming code or instructions implementing various functions of the treadmill control system 204.

Examples of the processors as described herein may include, but are not limited to, at least one of Qualcomm® Snapdragon® 800 and 801, Qualcomm® Snapdragon® 810 and 815 with 4G long-term evolution (LTE) Integration and 64-bit computing, Apple® A5 processor with 64-bit architecture, Apple® M5 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4650K and i5-4550K 22 nm Haswell, Intel® Core® i5-3550K 22 nm Ivy Bridge, the AMD®, FX™ family of processors, AMD®, FX-4300, FX-6300, and FX-8350 32 nm Vishera, AMD®, Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

The input/output module 312 and associated ports may be included to support communications over wired or wireless networks or links, for example with other communication devices, server devices, and/or peripheral devices. Examples of an input/output module 312 include an Ethernet port, a Universal Serial Bus (USB) port, Institute of Electrical and Electronics Engineers (IEEE) 1594, or other interface.

The treadmill control system 204 may also include one or more storage devices 308. By way of example, storage devices 308 may be disk drives, optical storage devices, solid-state storage devices such as a random access memory ("RAM") and/or a read-only memory ("ROM"), which can be programmable, flash-updateable and/or the like. The treadmill control system 204 may additionally include a computer-readable storage media reader; a communications system (e.g., a modem, a network card (wireless or wired), an infra-red communication device, etc.); and working memory 308, which may include RAM and ROM devices as described above. The treadmill control system 204 may also include a processing acceleration unit, which can include a digital signal processor, a special-purpose processor, and/or the like.

The computer-readable storage media reader can further be connected to a computer-readable storage medium, together (and, optionally, in combination with storage device(s)) comprehensively representing remote, local, fixed, and/or removable storage devices plus storage media for temporarily and/or more permanently containing computer-readable information. The communications system may permit data to be exchanged with an external or internal network and/or any other computer or device described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices, and/or other machine readable mediums for storing information.

The treadmill control system 204 may also comprise software elements including an operating system and/or other code. It should be appreciated that alternates to the treadmill control system 204 may have numerous variations from that described herein. For example, customized hardware might also be used and/or particular elements might be implemented in hardware, software (including portable software, such as applets), or both. Further, connection to other computing devices such as network input/output devices may be employed.

The power source and/or power control module 316 can include any type of power source, including, but not limited to, batteries, alternating current sources (from connections to a building power system or power line), solar cell arrays, etc. One or more components or modules may also be included to control the power source or change the characteristics of the provided power signal. Such modules can include one or more of, but is not limited to, power regulators, power filters, alternating current (AC) to direct current (DC) converters, DC to AC converters, receptacles, wiring, other converters, etc. The power source and/or power control module 316 functions to provide the treadmill control system 204 and any other system with power.

The data storage 320 can include any module for storing, retrieving, and/or managing data in one or more data stores and/or databases. The database or data stores may reside on a storage medium local to (and/or resident in) the treadmill control system 204 or in the treadmill 102. Alternatively, some of the data storage capability may be remote from the treadmill control system 204 or exercise, and in communication (e.g., via a network) to the treadmill control system 204. The database or data stores may reside in a storage-area network ("SAN") familiar to those skilled in the art. Similarly, any necessary files for performing the functions attributed to the treadmill control system 204 may be stored locally on the respective treadmill control system 204 and/or remotely, as appropriate. The databases or data stores may be a relational database, and the data storage module 320 may be adapted to store, update, and retrieve data in response to specifically-formatted commands. The data storage module 320 may also perform data management functions for any flat file, object oriented, or other type of database or data store.

A first data store that may be part of the exercise control system 300 is a profile data store 252 for storing data about user profiles and data associated with the users. A system data store 208 can include data used by the treadmill control system 204 and/or one or more of the components 324-352 to facilitate the functionality described herein. The data stores 208 and/or 252 may be as described in conjunction with FIGS. 1 and/or 8A-8D.

The user interface/input interfaces 324 may be as described herein for providing information or data and/or for receiving input or data from a user. Treadmill subsystems 328 can include any of the mechanical, electrical, electro-mechanical, computer, or other systems associated with the function of the treadmill 102. For example, treadmill subsystems 328 can include one or more of, but is not limited to, the roller system, the belt system, the motor control systems, the electrical system, the suspension, the tilt system, the motor control system, the multimedia system, etc. These systems are well known in the art and will not be described further.

Examples of the other systems and subsystems 324-352 may be as described further herein. For example, the user interface(s)/input interface(s) 324 may be as described in FIG. 3; the treadmill subsystems 328 may be as described in FIG. 3; the user interaction subsystem 332 may be as described in conjunction with the user/device interaction subsystem 615 of FIG. 6; and the sensor(s)/sensor subsystem 340 may be as described in FIG. 5.

Figure 4:
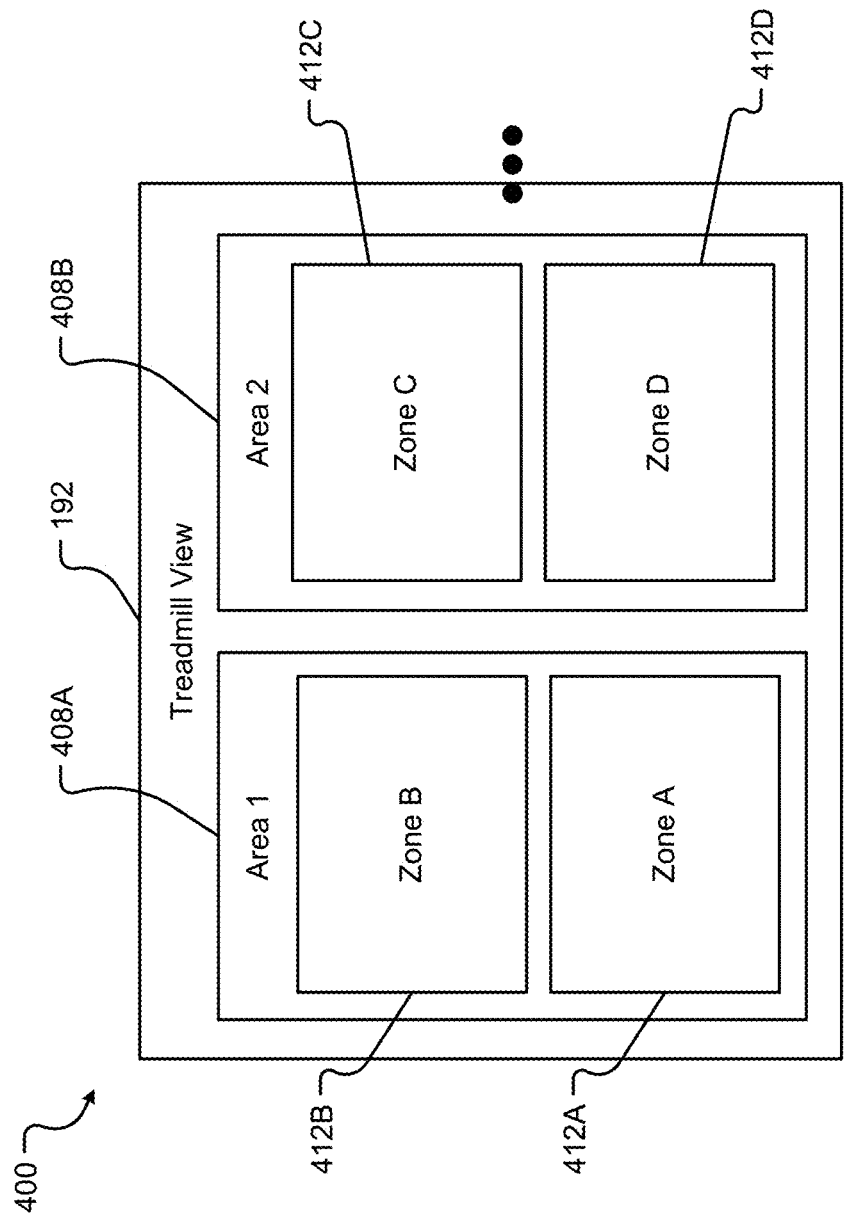
FIG. 4 is a block diagram of an embodiment of a view from sensors of an exercise system separated into areas and/or zones.

FIG. 4 shows a configuration of a view for a treadmill camera 190. In general, a camera 190 may provide functionality based at least partially on one or more areas, zones, and distances, associated with the a view 192 of the camera 190. Non-limiting examples of this functionality are provided herein below.

An arrangement or configuration for the camera view 192 is as shown in FIG. 4. The view arrangement 400 can include one or more areas 408 within the exercise environment. An area can be a larger part of the environment around the treadmill 102. Thus, area one 408A may include the area to the right of the treadmill 102. Area two 408B may include a portion to the left of the treadmill 102. The view 192 may also be divided into other areas. Thus, one area may be associated with the user's right hand and one area associated with a user's left hand. Each area 408 may include one or more camera sensors 190 that are positioned or operate to provide information about that area 408.

Each area 408 may be further separated into one or more zones 412 within the area 408. For example, area 1 408A may be separated into zone A 412A, and zone B 412B. Each zone 412 may be associated with a particular portion of the view 192. For example, zone A 412A may be associated with a lower region of the user. Zone B 412B, may be associated with an upper region of the user. Each zone 412 may include one or more cameras 190 that are positioned or configured to collect information about the environment or ecosystem associated with that zone or person. In other situations, a single camera logically separates the area 408 into zones and treats gestures received in the different zones differently.

A second area 408B may include more than two zones similar to that described in conjunction with area 408A. For example, area 408B may include two zones, 412C and 412D. These zones 412C, 412D may be associated with left hand of the user of a treadmill 102. The number of zones 412 is unlimited within the areas as the areas are also unlimited inside the view 192.

Figure 5:
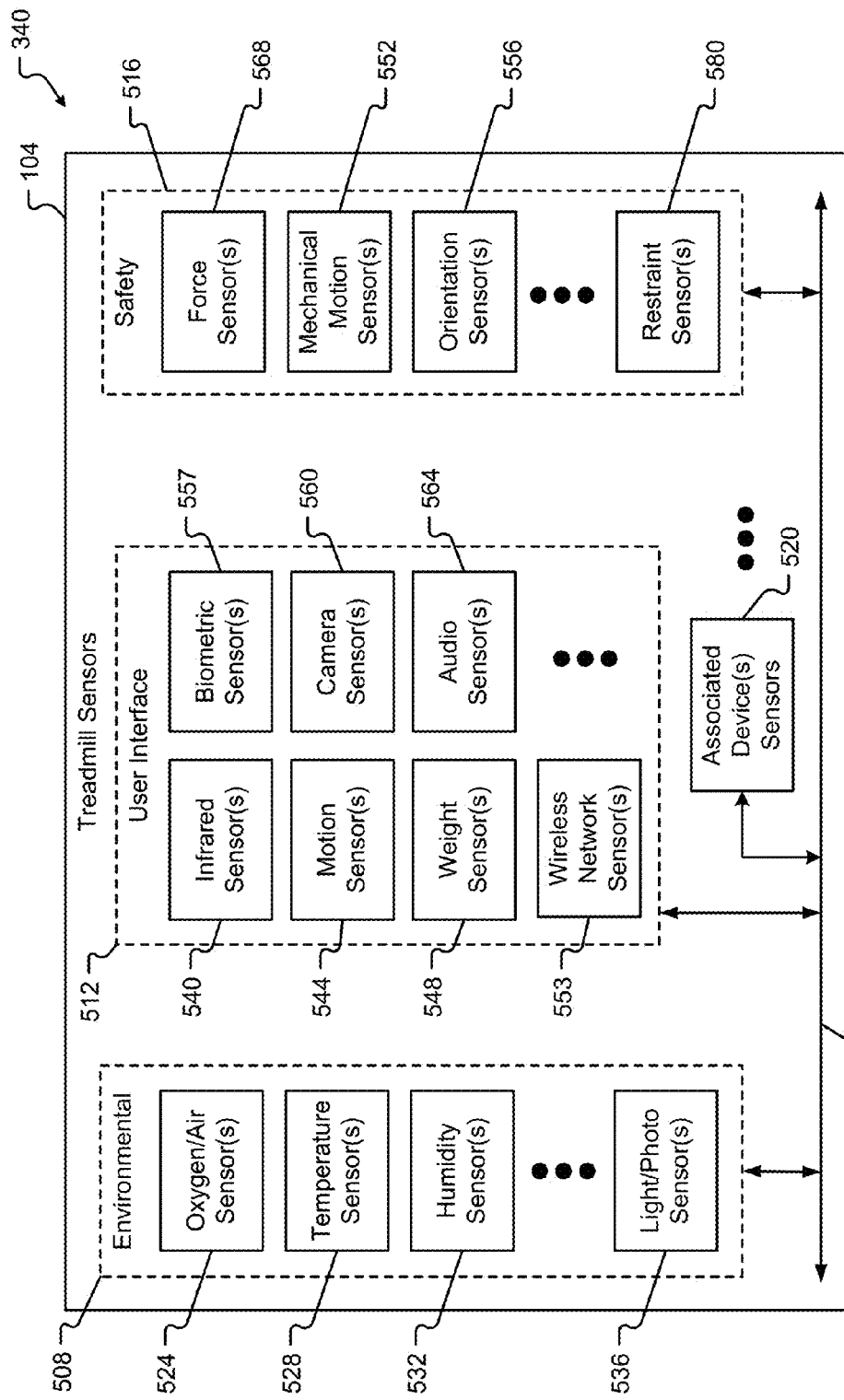
FIG. 5 is a block diagram of an embodiment of sensors for exercise equipment.

FIG. 5 shows block diagrams of various sensors that may be associated with a treadmill 102. Sensors having the same symbol or name may include the same, or substantially the same, functionality as those sensors described elsewhere in the present disclosure. Further, although the various sensors are depicted in conjunction with specific groups (e.g., environmental 508, 508E, user interface 512, safety 516, 516E, etc.) the sensors should not be limited to the groups in which they appear. In other words, the sensors may be associated with other groups or combinations of groups and/or disassociated from one or more of the groups shown. The sensors as disclosed herein may communicate with each other, the devices 126, 124, and/or the treadmill control system 204 via one or more communications channel(s) 356.

FIG. 5 is a block diagram of an embodiment of sensors 340 for a treadmill 102. The sensors 340 may be arranged into one or more groups, based at least partially on the function of the sensors 340. The treadmill sensors may include an environmental group 508, a user interface group 512, and a safety group 516. Additionally or alternatively, there may be sensors associated with various devices (e.g., devices 126, 124, smart phones, tablets, mobile computers, etc.)

The environmental group 508 may comprise sensors configured to collect data relating to the environment of a treadmill 102. Examples of environmental sensors associated with the environmental group 508 may include, but are not limited to, oxygen/air sensors 524, temperature sensors 528, humidity sensors 532, light/photo sensors 536, and more. The oxygen/air sensors 524 may be configured to detect a quality of the air in around the treadmill 102 (e.g., ratios and/or types of gasses comprising the air around the treadmill 102, dangerous gas levels, safe gas levels, etc.). Temperature sensors 528 may be configured to detect temperature readings of one or more objects, users 120, and/or areas 408 of a treadmill 102. Humidity sensors 532 may detect an amount of water vapor present around the treadmill 102. The light/photo sensors 536 can detect an amount of light present around the treadmill 102.

The user interface group 512 may comprise sensors configured to collect data relating to one or more users 120 of a treadmill 102. As can be appreciated, the user interface group 512 may include sensors that are configured to collect data from users 120 in one or more areas 408 and zones 412 of the treadmill 102. For example, each area 408 and/or zone 412 of the treadmill 102 may include one or more of the sensors in the user interface group 512. Examples of user interface sensors associated with the user interface group 512 may include, but are not limited to, infrared (IR) sensors 540, motion sensors 544, weight sensors 548, wireless network sensors 553, biometric sensors 557, camera (or image) sensors 560, audio sensors 564, and more.

Infrared sensors 540 may be used to measure IR light irradiating from at least one surface, user 120, or other object. Among other things, the Infrared sensors 540 may be used to measure temperatures, form images (especially in low light conditions), identify users 120, and even detect motion around the treadmill 102.

The motion sensors 544 may be detect motion around the treadmill 102. Weight sensors 548 may be employed to collect data relating to objects and/or users 120 of the treadmill 102. In some cases, the weight sensors 548 may be included in the base of a treadmill 102.

Optionally, the treadmill 102 may include a wireless network sensor 553. This sensor 552 may be configured to detect one or more wireless network(s) available to the treadmill 102. Examples of wireless networks may include, but are not limited to, wireless communications utilizing Bluetooth®, Wi-Fi™, ZigBee, IEEE 802.7, and other wireless technology standards. For example, a mobile hotspot may be detected near the treadmill 102 via the wireless network sensor 553. In this case, the treadmill 102 may determine to utilize and/or share the mobile hotspot detected via/with one or more other devices 126, 124 and/or components associated with the treadmill 102.

Biometric sensors 557 may be employed to identify and/or record characteristics associated with a user 120. It is anticipated that biometric sensors 557 can include at least one of image sensors, IR sensors, fingerprint readers, weight sensors, load cells, force transducers, heart rate monitors, blood pressure monitors, and the like as provided herein.

The camera sensors 560 may be similar to image sensors 190, as described in conjunction with FIGS. 1V and 1W.

Optionally, the camera sensors 560 may record still images, video, and/or combinations thereof. The audio sensors 564 may be configured to receive audio input from a user 120 of the treadmill 102. The audio sensor 564 may be a component of the device 176. The audio input from a user 120 may correspond to voice commands, conversations around a the treadmill 102, phone calls made to the treadmill 102, and/or other audible expressions made in the treadmill 102.

The safety group 516 may comprise sensors configured to collect data relating to the safety of a user 120 and/or one or more components of a treadmill 102. Examples of safety sensors associated with the safety group 516 may include, but are not limited to, force sensors 568, mechanical motion sensors 552, orientation sensors 556, restraint sensors 580, and more.

The force sensors 568 may include one or more sensors inside the treadmill 102 configured to detect a force observed on the treadmill 102. One example of a force sensor 568 may include a force transducer that converts measured forces (e.g., force, weight, pressure, etc.) into output signals.

Mechanical motion sensors 552 may correspond to encoders, accelerometers, damped masses, and the like. Optionally, the mechanical motion sensors 552 may be adapted to measure the force of gravity (i.e., G-force) as observed inside the treadmill 102. Measuring the G-force observed inside a treadmill 102 can provide valuable information related to an exerciser's acceleration, deceleration, falls, and/or forces that may have been suffered by one or more users 120 on the treadmill 102. As can be appreciated, the mechanical motion sensors 552 can be located in an interior space of the treadmill 102.

Orientation sensors 556 can include accelerometers, gyroscopes, magnetic sensors, and the like that are configured to detect an orientation or a configuration associated with the treadmill 102 (e.g., amount of tile on the belt or ramp of the treadmill). Similar to the mechanical motion sensors 552, the orientation sensors 556 can be located in or on the treadmill 102.

The restraint sensors 580 may correspond to sensors associated with one or more restraint devices and/or systems in a treadmill 102. Corded connectors, clips, or devices used to stop the treadmill 102 if a user falls are examples of restraint devices and/or systems. As can be appreciated, the restraint devices 280 and/or systems may be associated with one or more sensors that are configured to detect a state of the device/system. The state may include extension, engagement, retraction, disengagement, deployment, and/or other electrical or mechanical conditions associated with the device/system.

The associated device sensors 520 can include any sensors that are associated with a device 126, 124 in the treadmill 102. As previously stated, typical devices 126, 124 may include smart phones, tablets, laptops, mobile computers, and the like. It is anticipated that the various sensors associated with these devices 126, 124 can be employed by the treadmill control system 204. For example, a typical smart phone can include an image sensor, an IR sensor, audio sensor, gyroscope, accelerometer, wireless network sensor, fingerprint reader, and more. It is an aspect of the present disclosure that one or more of these associated device sensors 520 may be used by one or more subsystems of the exercise system 200.

Figure 6:
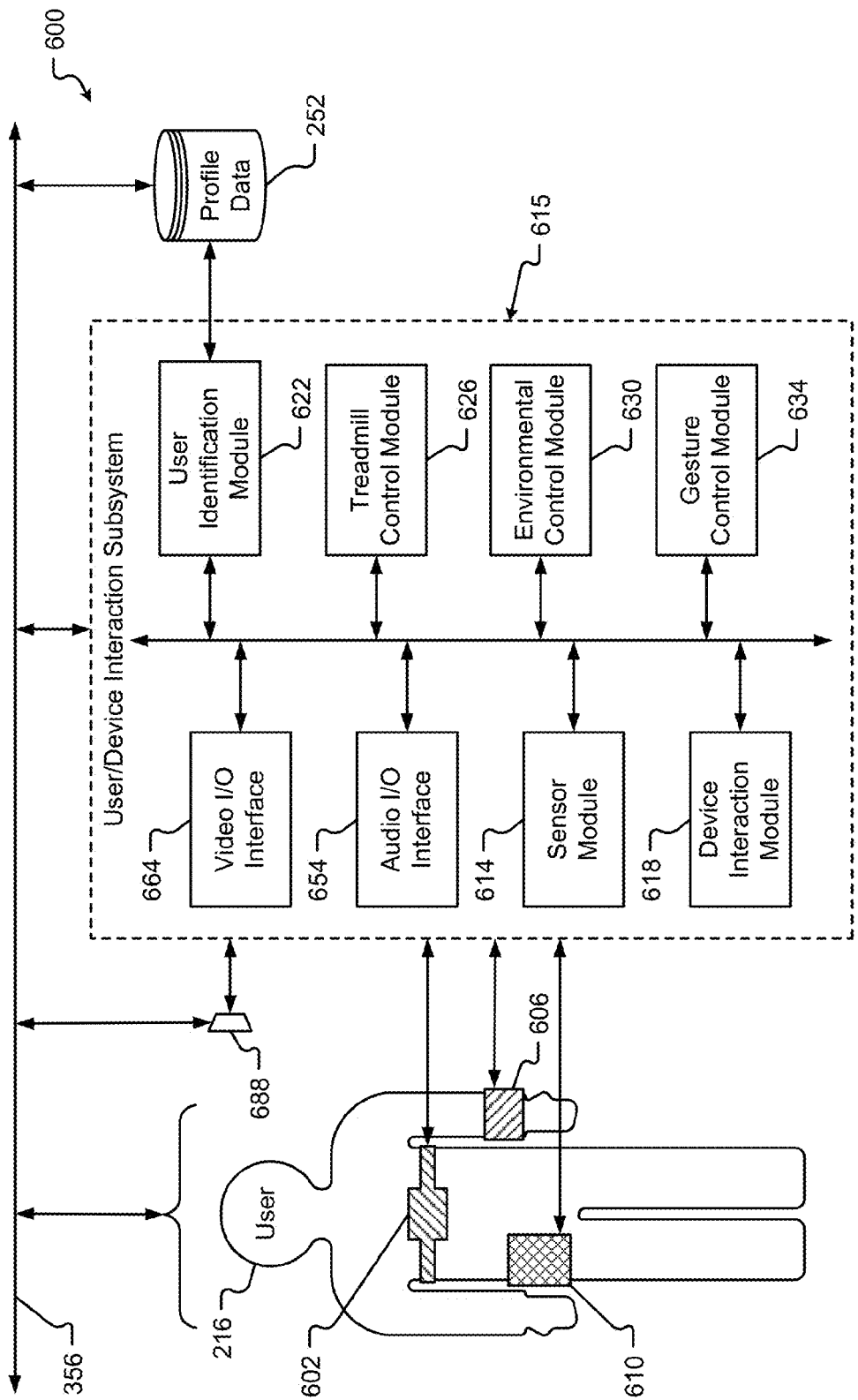
FIG. 6 is a block diagram of an embodiment of a user and device interaction subsystem for exercise equipment.

FIG. 6 is a block diagram of an embodiment of a user/device interaction subsystem 615 of a treadmill user interface system 600. The user/device interaction subsystem 615 may comprise hardware and/or software that conduct various operations for or with the treadmill 102. For instance, the user/device interaction subsystem 615 may include at least one user interaction subsystem 332 and device interaction subsystem 352 as previously described. These operations may include, but are not limited to, providing information to the user 120, receiving input from the user 120, and controlling the functions or operation of the treadmill 102, etc. Among other things, the user/device interaction subsystem 615 may include a computing system operable to conduct the operations as described herein.

Optionally, the user/device interaction subsystem 615 can include one or more of the components and modules provided herein. For instance, the user/device interaction subsystem 615 can include one or more of a video input/output interface 664, an audio input/output interface 654, a sensor module 614, a device interaction module 618, a user identification module 622, a treadmill control module 626, an environmental control module 630, and a gesture control module 634. The user/device interaction subsystem 615 may be in communication with other devices, modules, and components of the system 600 via the communications channel 356.

The user/device interaction subsystem 615 may be configured to receive input from a user 120 and/or device 124, 126 via one or more components of the system. By way of example, a user 120 may provide input to the user/device interaction subsystem 615 via wearable devices 602, 606, 610, video input (e.g., via at least one image sensor/camera 560, etc.) audio input (e.g., via the microphone, audio input source, etc.), gestures (e.g., via at least one image sensor 560, motion sensor 544, etc.), device input (e.g., via a device 126, 124 associated with the user, etc.), combinations thereof, and the like.

The wearable devices 602, 606, 610 can include heart rate monitors, blood pressure monitors, glucose monitors, pedometers, movement sensors, wearable computers, and the like. Examples of wearable computers may be worn by a user 120 and configured to measure user activity, determine energy spent based on the measured activity, track user sleep habits, determine user oxygen levels, monitor heart rate, provide alarm functions, and more. It is anticipated that the wearable devices 602, 606, 610 can communicate with the user/device interaction subsystem 615 via wireless communications channels or direct connection (e.g., where the device docks, or connects, with a USB port or similar interface of the treadmill 102). The wearable devices 602, 606, 610 may be the same or similar to the wearable 138.

A sensor module 614 may be configured to receive and/or interpret input provided by one or more sensors of the treadmill 102. In some cases, the sensors may be associated with one or more user devices (e.g., wearable devices 602, 606, 610, smart phones 126, mobile computing devices 126, 124, and the like). Optionally, the sensors may be associated with the treadmill 102, as described in conjunction with FIG. 5.

The device interaction module 618 may communicate with the various devices as provided herein. Optionally, the device interaction module 618 can provide content, information, data, and/or media associated with the various subsystems of the treadmill user interface system 600 to one or more devices 126, 124, 186, etc. Additionally or alternatively, the device interaction module 618 may receive content, information, data, and/or media associated with the various devices provided herein.

The user identification module 622 may be configured to identify a user 120 associated with the treadmill 102. The identification may be based on user profile information that is stored in profile data 252. For instance, the user identification module 622 may receive characteristic information about a user 120 via a device, a camera, and/or some other input. The received characteristics may be compared to data stored in the profile data 252. Where the characteristics match, the user 120 is identified. As can be appreciated, where the characteristics do not match a user profile, the user identification module 622 may communicate with other subsystems in the treadmill 102 to obtain and/or record profile information about the user 120. This information may be stored in a memory and/or the profile data storage 252.

The treadmill control module 626 may be configured to control settings, features, and/or the functionality of a treadmill 102. In some cases, the treadmill control module 626 can communicate with the treadmill control system 204 to control critical functions (e.g., motor system controls, ramp tilt, etc.) and/or noncritical functions based at least partially on user/device input received by the user/device interaction subsystem 615.

The environmental control module 630 may be configured to control settings, features, and/or other conditions associated with the environment of a treadmill 102. For example, the environmental control module 630 may control a fan directed at the user 120 to lower the user's temperature. As can be appreciated, the environmental control module 630 may control the environment based at least partially on user/device input received by the user/device interaction subsystem 615.

The gesture control module 634 is configured to interpret gestures provided by a user 120 of the treadmill 102. Optionally, the gesture control module 634 may provide control signals to one or more of the exercise systems 300 disclosed herein. For example, a user 120 may provide gestures to control the environment, critical and/or noncritical exercise functions, the infotainment system, communications, networking, and more. Optionally, gestures may be provided by a user 120 and detected via one or more of the sensors as described herein. As another example, one or more video sensors may receive gesture input from a user 120 and provide the gesture input to the gesture control module 634. Continuing this example, the gesture input is interpreted by the gesture control module 634. This interpretation may include comparing the gesture input to gestures stored in a memory. The gestures stored in memory may include one or more functions and/or controls mapped to specific gestures. When a match is determined between the detected gesture input and the stored gesture information, the gesture control module 634 can provide a control signal to any of the systems/subsystems as disclosed herein.

One or more gestures used to interface with the treadmill control system 204 may be as described in conjunction with FIG. 7A through 7K. FIGS. 7A through 7H depict various graphical representations of gesture inputs that may be recognized by the devices 126, 124. The gestures may be performed not only by a user's body part, such as a digit, but also by other devices, such as a stylus, that may be sensed by the contact sensing portion(s) of a screen associated with the device 126, 124. In general, gestures are interpreted differently, based on where the gestures are performed (either directly on a display or in a gesture capture region). For example, gestures in a display may be directed to a desktop or application, and gestures in a gesture capture region may be interpreted as for the system.

With reference to FIGS. 7A-7H, a first type of gesture, a touch gesture 720, is substantially stationary on a portion (e.g., a screen, a display, etc.) of a device 126, 124 for a selected length of time. A circle 728 represents a touch or other contact type received at particular location of a contact sensing portion of the screen. The circle 728 may include a border 732, the thickness of which indicates a length of time that the contact is held substantially stationary at the contact location. For instance, a tap 720 (or short press) has a thinner border 732A than the border 732B for a long press 724 (or for a normal press). The long press 724 may involve a contact that remains substantially stationary on the screen for longer time period than that of a tap 720. As will be appreciated, differently defined gestures may be registered depending upon the length of time that the touch remains stationary prior to contact cessation or movement on the screen.

Figure 7A:
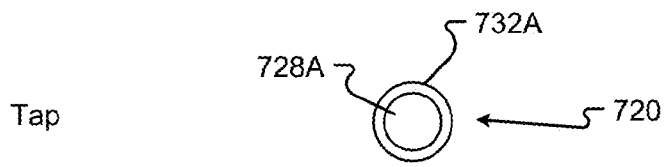
FIG. 7A is a graphical representation of an embodiment of a gesture that a user may perform to provide input to an exercise control system.
Figure 7B:
FIG. 7B is a graphical representation of an embodiment of a gesture that a user may perform to provide input to an exercise control system.
Figure 7C:
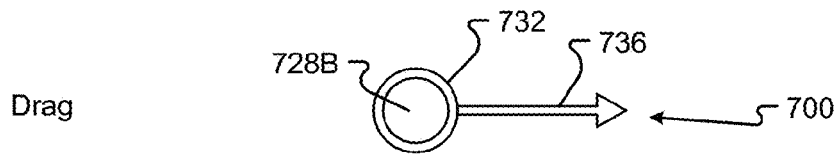
FIG. 7C is a graphical representation of an embodiment of a gesture that a user may perform to provide input to an exercise control system.

With reference to FIG. 7C, a drag gesture 700 on the screen is an initial contact (represented by circle 728) with contact movement 736 in a selected direction. The initial contact 728 may remain stationary on the screen for a certain amount of time represented by the border 732. The drag gesture typically requires the user to contact an icon, window, or other displayed image at a first location followed by movement of the contact in a drag direction to a new second location desired for the selected displayed image. The contact movement need not be in a straight line but have any path of movement so long as the contact is substantially continuous from the first to the second locations.

Figure 7D:
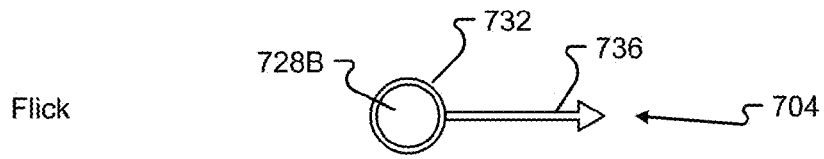
FIG. 7D is a graphical representation of an embodiment of a gesture that a user may perform to provide input to an exercise control system.

With reference to FIG. 7D, a flick gesture 704 on the screen is an initial contact (represented by circle 728) with truncated contact movement 736 (relative to a drag gesture) in a selected direction. A flick may have a higher exit velocity for the last movement in the gesture compared to the drag gesture. The flick gesture can, for instance, be a finger snap following initial contact. Compared to a drag gesture, a flick gesture generally does not require continual contact with the screen from the first location of a displayed image to a predetermined second location. The contacted displayed image is moved by the flick gesture in the direction of the flick gesture to the predetermined second location. Although both gestures commonly can move a displayed image from a first location to a second location, the temporal duration and distance of travel of the contact on the screen is generally less for a flick than for a drag gesture.

Figure 7E:
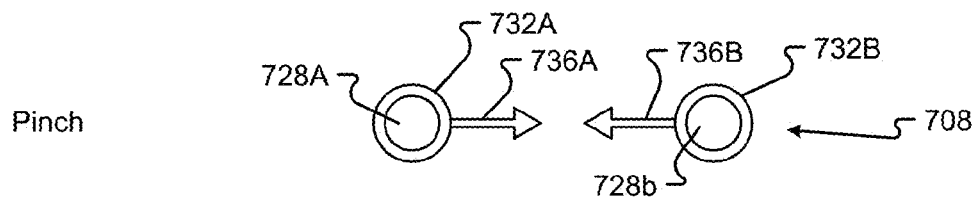
FIG. 7E is a graphical representation of an embodiment of a gesture that a user may perform to provide input to an exercise control system.

With reference to FIG. 7E, a pinch gesture 708 on the screen is depicted. The pinch gesture 708 may be initiated by a first contact 728A to the screen by, for example, a first digit and a second contact 728B to the screen by, for example, a second digit. The first and second contacts 728A,B may be detected by a common contact sensing portion of a common screen, by different contact sensing portions of a common screen, or by different contact sensing portions of different screens. The first contact 728A is held for a first amount of time, as represented by the border 732A, and the second contact 728B is held for a second amount of time, as represented by the border 732B. The first and second amounts of time are generally substantially the same, and the first and second contacts 728A,B generally occur substantially simultaneously. The first and second contacts 728A,B generally also include corresponding first and second contact movements 736A,B, respectively. The first and second contact movements 736A,B are generally in opposing directions. Stated another way, the first contact movement 736A is towards the second contact 736B, and the second contact movement 736B is towards the first contact 736A. More simply stated, the pinch gesture 708 may be accomplished by a user's digits touching the screen in a pinching motion.

Figure 7F:
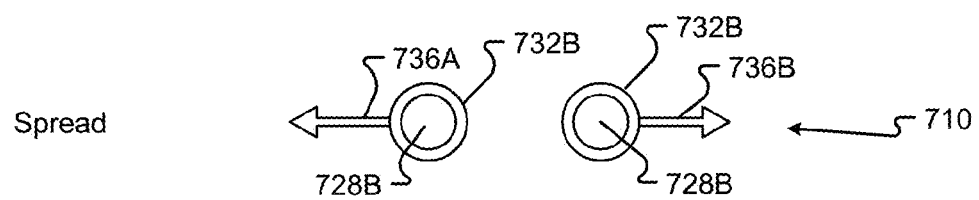
FIG. 7F is a graphical representation of an embodiment of a gesture that a user may perform to provide input to an exercise control system.

With reference to FIG. 7F, a spread gesture 710 on the screen is depicted. The spread gesture 710 may be initiated by a first contact 728A to the screen by, for example, a first digit, and a second contact 728B to the screen by, for example, a second digit. The first and second contacts 728A,B may be detected by a common contact sensing portion of a common screen, by different contact sensing portions of a common screen, or by different contact sensing portions of different screens. The first contact 728A is held for a first amount of time, as represented by the border 732A, and the second contact 728B is held for a second amount of time, as represented by the border 732B. The first and second amounts of time are generally substantially the same, and the first and second contacts 728A,B generally occur substantially simultaneously. The first and second contacts 728A,B generally also include corresponding first and second contact movements 736A,B, respectively. The first and second contact movements 736A,B are generally in an opposing direction. Stated another way, the first and second contact movements 736A,B are away from the first and second contacts 728A,B. More simply stated, the spread gesture 710 may be accomplished by a user's digits touching the screen in a spreading motion.

Figure 7G:
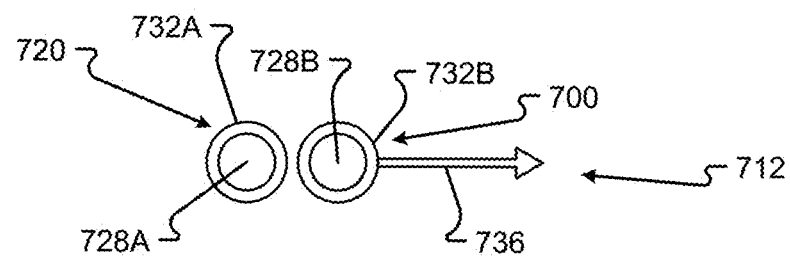
FIG. 7G is a graphical representation of an embodiment of a gesture that a user may perform to provide input to an exercise control system.
Figure 7H:
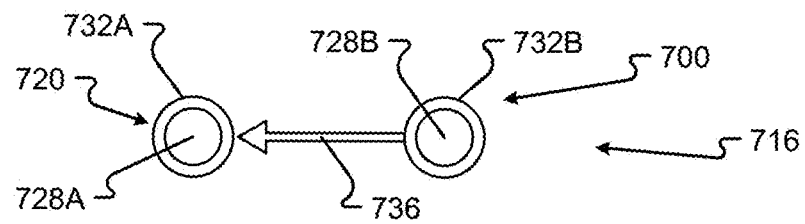
FIG. 7H is a graphical representation of an embodiment of a gesture that a user may perform to provide input to an exercise control system.

The above gestures may be combined in any manner, such as those shown by FIGS. 7G and 7H, to produce a determined functional result. For example, in FIG. 7G a tap gesture 720 is combined with a drag or flick gesture 712 in a direction away from the tap gesture 720. In FIG. 7H, a tap gesture 720 is combined with a drag or flick gesture 716 in a direction towards the tap gesture 720.

The functional result of receiving a gesture can vary depending on a number of factors, including a state of the treadmill 102, display, or screen of a device, a context associated with the gesture, or sensed location of the gesture, etc. The state of the treadmill 102 commonly refers to one or more of a configuration of the treadmill 102, a display orientation, and user and other inputs received by the treadmill 102. Context commonly refers to one or more of the particular application(s) selected by the gesture and the portion(s) of the application currently executing, whether the application is a single- or multi-screen application, and whether the application is a multi-screen application displaying one or more windows. A sensed location of the gesture commonly refers to whether the sensed set(s) of gesture location coordinates are on a touch sensitive display or a gesture capture region of a device 126, 124, whether the sensed set(s) of gesture location coordinates are associated with a common or different display, or screen, or device 126, 124, and/or what portion of the gesture capture region contains the sensed set(s) of gesture location coordinates.

A tap, when received by a touch sensitive display of a device 126, 124, can be used, for instance, to select an icon to initiate or terminate execution of a corresponding application, to maximize or minimize a window, to reorder windows in a stack, and/or to provide user input such as by keyboard display or other displayed image. A drag, when received by a touch sensitive display of a device 126, 124, can be used, for instance, to relocate an icon or window to a desired location within a display, to reorder a stack on a display, or to span both displays (such that the selected window occupies a portion of each display simultaneously). A flick, when received by a touch sensitive display of a device 126, 124 or a gesture capture region, can be used to relocate a window from a first display to a second display or to span both displays (such that the selected window occupies a portion of each display simultaneously). Unlike the drag gesture, however, the flick gesture is generally not used to move the displayed image to a specific user-selected location but to a default location that is not configurable by the user.

The pinch gesture, when received by a touch sensitive display or a gesture capture region of a device 126, 124, can be used to minimize or otherwise increase the displayed area or size of a window (typically when received entirely by a common display), to switch windows displayed at the top of the stack on each display to the top of the stack of the other display (typically when received by different displays or screens), or to display an application manager (a "pop-up window" that displays the windows in the stack). The spread gesture, when received by a touch sensitive display or a gesture capture region of a device 126, 124, can be used to maximize or otherwise decrease the displayed area or size of a window, to switch windows displayed at the top of the stack on each display to the top of the stack of the other display (typically when received by different displays or screens), or to display an application manager (typically when received by an off-screen gesture capture region on the same or different screens).

The combined gestures of FIG. 7G, when received by a common display capture region in a common display or screen of a device 126, 124, can be used to hold a first window location constant for a display receiving the gesture while reordering a second window location to include a window in the display receiving the gesture. The combined gestures of FIG. 7H, when received by different display capture regions in a common display or screen of a device 126, 124 or in different displays or screens of one more devices 126, 124, can be used to hold a first window location for a display receiving the tap part of the gesture while reordering a second window location to include a window in the display receiving the flick or drag gesture. Although specific gestures and gesture capture regions in the preceding examples have been associated with corresponding sets of functional results, it is to be appreciated that these associations can be redefined in any manner to produce differing associations between gestures and/or gesture capture regions and/or functional results.

Figure 7I:
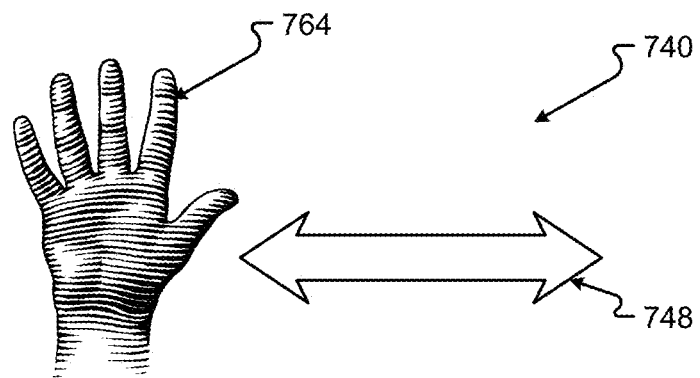
FIG. 7I is a graphical representation of an embodiment of a gesture that a user may perform to provide input to an exercise control system.
Figure 7J:
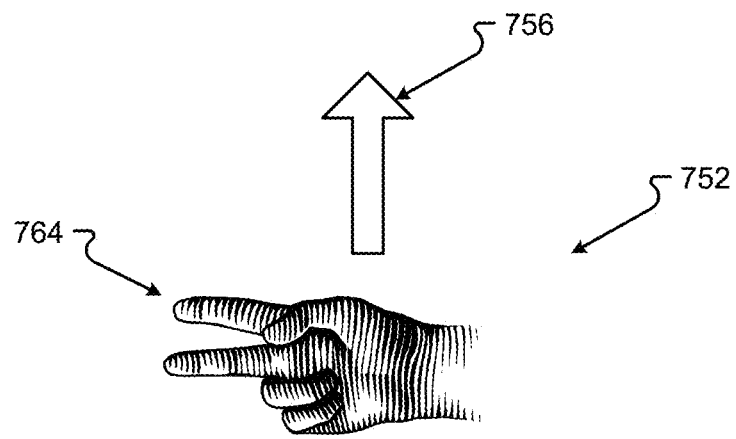
FIG. 7J is a graphical representation of an embodiment of a gesture that a user may perform to provide input to an exercise control system.
Figure 7K:
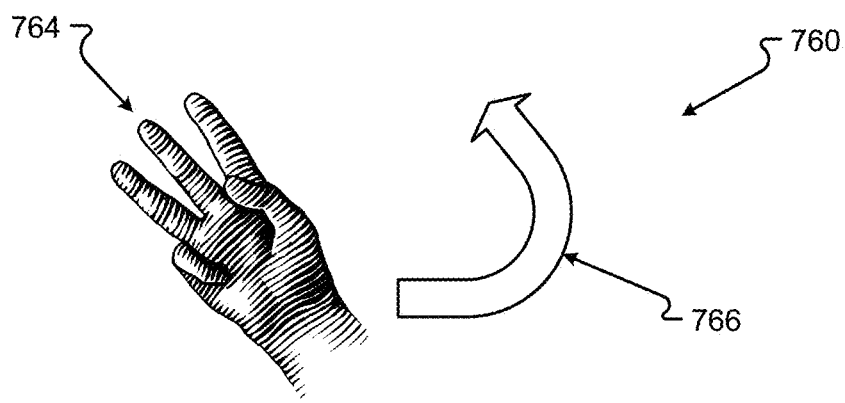
FIG. 7K is a graphical representation of an embodiment of a gesture that a user may perform to provide input to an exercise control system.

Gestures that may be completed in three-dimensional space and not on a touch sensitive screen or gesture capture region of a device 126, 124 may be as shown in FIGS. 7I-7K. The gestures may be completed in an area where a sensor, such as an optical sensor 190, infrared sensor, or other type of sensor, may detect the gesture. For example, the gesture 740 in FIG. 7I may be executed by a person when the person opens their hand 764 and moves their hand in a back and forth direction 748 as a gesture 740 to complete some function with the treadmill 102. For example gesture 740 may change the station of the radio in the treadmill 102. The sensors 242 may both determine the configuration of the hand 764 and the vector of the movement. The vector and hand configuration can be interpreted to mean certain things to the treadmill control system 204 and produce different results, especially if received in different areas 408 or zones 412.

In another example of a gesture 752 in FIG. 7J, a user may configure their hand 764 to extend two fingers and move the hand 764 in an up and down operation 756. This gesture 752 may control the volume of the radio or some other function. For instance, this gesture 752 may be configured to place the exercise in a "valet" mode to, among other things, restrict access to certain features associated with the exercise. Again, the sensors 242 may determine how the person has configured their hand 764, and the vector of the movement. In another example of a gesture 760 shown in FIG. 7K, a user may extend their middle three fingers at an angle that is substantially 45° for vertical from straight vertical and circle the hand in a counter-clockwise motion 766. This gesture 760 may cause the exercise equipment to change the heat setting or do some other function. As can be understood by one skilled in the art, the configurations of the hand and the types of movement are variable. Thus, the user may configure the hand 764 in any way imaginable and may also move that hand 764 in any direction with any vector in three-dimensional space.

The gestures 740, 752, 760, as shown in FIGS. 7I-7K, may occur in a predetermined volume of space within the treadmill 102. The gestures 740, 752, 760 may be made within area 1 508A between zones A 512A and B 512B. However, there may be other areas 408 where a user may use certain gestures, where sensors 242 may be able to determine a certain function is desired. Gestures that may be similar but used in different areas within the treadmill 102 may cause different functions to be performed. For example, the gesture 740 in FIG. 7I, if used in zone B 512B, may change the speed of the treadmill, but may change the station of a radio if used in zone A 512A. Further, the gestures may be made with other body parts or, for example, different expressions of a person's face and may be used to control functions in the treadmill 102. Also, the user may use two hands in some circumstances or do other types of physical movements that can cause different reactions in the treadmill 102.

FIGS. 8A-8D show various embodiments of a data structure 800 to store different settings. The data structure 800 may include one or more of data files or data objects 804, 850, 870, 880. Thus, the data structure 800 may represent different types of databases or data storage, for example, object-oriented data bases, flat file data structures, relational database, or other types of data storage arrangements. Embodiments of the data structure 800 disclosed herein may be separate, combined, and/or distributed. As indicated in FIGS. 8A-8D, there may be more or fewer portions in the data structure 800, as represented by ellipses 844. Further, there may be more or fewer files in the data structure 800, as represented by ellipses 848.

Referring to FIG. 8A, a first data structure is shown. The data file 804 may include several portions 808-842 representing different types of data. Each of these types of data may be associated with a user, as shown in portion 808.

There may be one or more user records 840 and associated data stored within the data file 804. As provided herein, the user can be any person that uses or rides within the exercise or exercise equipment 102. The user may be identified in portion 812. For the treadmill 102, the user may include a set of one or more features that may identify the user. These features may be the physical characteristics of the person that may be identified by facial recognition or some other type of system. In other situations, the user may provide a unique code to the treadmill control system 204 or provide some other type of data that allows the treadmill control system 204 to identify the user. The features or characteristics of the user are then stored in portion 812.

Each user, identified in portion 808, may have a different set of settings for each area 408 and/or each zone 412 of the view 192. Thus, each set of settings may also be associated with a predetermined zone 412 or area 408. The zone 412 is stored in portion 820, and the area 408 is stored in portion 820.

One or more settings may be stored in portion 824. These settings 824 may be the configurations of different functions of the treadmill 102 that are specified by or for that user. For example, the settings 824 may be the position of a treadmill platform, a heating/cooling setting, a radio setting, a speed setting, or some other type of setting associated with the treadmill 102. Further, in exercises adapted to have a configurable console, the settings 824 may also provide for how that-up display or console is configured for this particular user.

The sensors 242 within the treadmill 102 may be able to either obtain or track health data in portion 828. Health data 828 may include any type of physical characteristic associated with the user. For example, a heart rate, a blood pressure, a temperature, or other types of heath data may be obtained and stored in portion 828. The user may have this health data tracked over a period of time to allow for statistical analysis of the user's health while operating the treadmill 102. In this way, if some function of the user's health deviates from a norm (e.g., a baseline measurement, average measurements taken over time, and the like), the treadmill 102 may be able to determine there is a problem with the person and react to that data.

One or more gestures may be stored in portion 832. Thus, the gestures used and described in conjunction FIG. 7A through 7K may be configurable. These gestures may be determined or created by the user and stored in portion 732. A user may have different gestures for each zone 412 or area 408 within the view 192. Further, one or more users may share gestures as shown in portion 832. Each user may have a common set of gestures that they use in zone A 412A. Each of these gestures may be determined or captured and then stored with their characteristics (e.g., vector, position of gesture, etc.) in portion 832.

One or more sets of safety parameters may be stored in portion 836. Safety parameters 836 may be common operating characteristics for this exerciser that if deviated from may determine there is a problem with the exerciser or the treadmill 102. For example, a certain exercise routine may be used repeatedly and an average speed or mean speed may be determined. If the mean speed deviates by some number of standard deviations, a problem with the treadmill 102 or the user may be determined. In another example, the health characteristics or exercising experience of the user may be determined. If the user exercises in a certain position where their head occupies a certain portion of three-dimensional space, the treadmill control system 204 may determine that the safety parameter includes the users face or head being within this certain portion of the exercise space. If the user's head deviates from that space for some amount of time, the treadmill control system 204 can determine that something is wrong with the user and change the function or operation of the treadmill 102 to assist the exerciser. This may happen, for example, when a user falls. If the user's head droops and no longer occupies a certain three dimensional space, the treadmill control system 204 can determine that the exerciser had suffered a medical problem and may take control of the operation of the exercise to stop the machine and report the emergency. In other examples, if the user's reaction time is too slow or some other safety parameter is not nominal, the treadmill control system 204 may determine that the user is having other medical problem. The treadmill control system 204 may then assume control of the exercise to ensure that the exerciser is safe.

Information corresponding to a user and/or a user profile may be stored in the profile information portion 838. For example, the profile information 838 may include data relating to at least one of current data, historical data, a user preference, user habit, user routine, observation, audible recording data, text data, email data, behavior associated with the aforementioned data, and the like. The data in the profile information portion 838 may be stored in one or more of the data structures 800 provided herein. As can be appreciated, these one or more data structures may be stored in one or more memory locations. Examples of various memory locations are described in conjunction with FIG. 2.

One or more additional data fields may be stored in the linked data portion 842 as data and/or locations of data. The linked data 842 may include at least one of pointers, addresses, location identification, data source information, and other information corresponding to additional data associated with the data structure 800. Optionally, the linked data portion 842 may refer to data stored outside of a particular data structure 800. For example, the linked data portion 842 may include a link/locator to the external data. Continuing this example, the link/locator may be resolved (e.g., via one or more of the methods and/or systems provided herein, etc.) to access the data stored outside of the data structure 800. Additionally or alternatively, the linked data portion 842 may include information configured to link the data objects 804 to other data files or data objects 850, 850, 880. For instance, the data object 804 relating to a user may be linked to at least one of a device data object 850, a exercise system data object 870, and a exercise data object 880, to name a few.

Figure 8B:
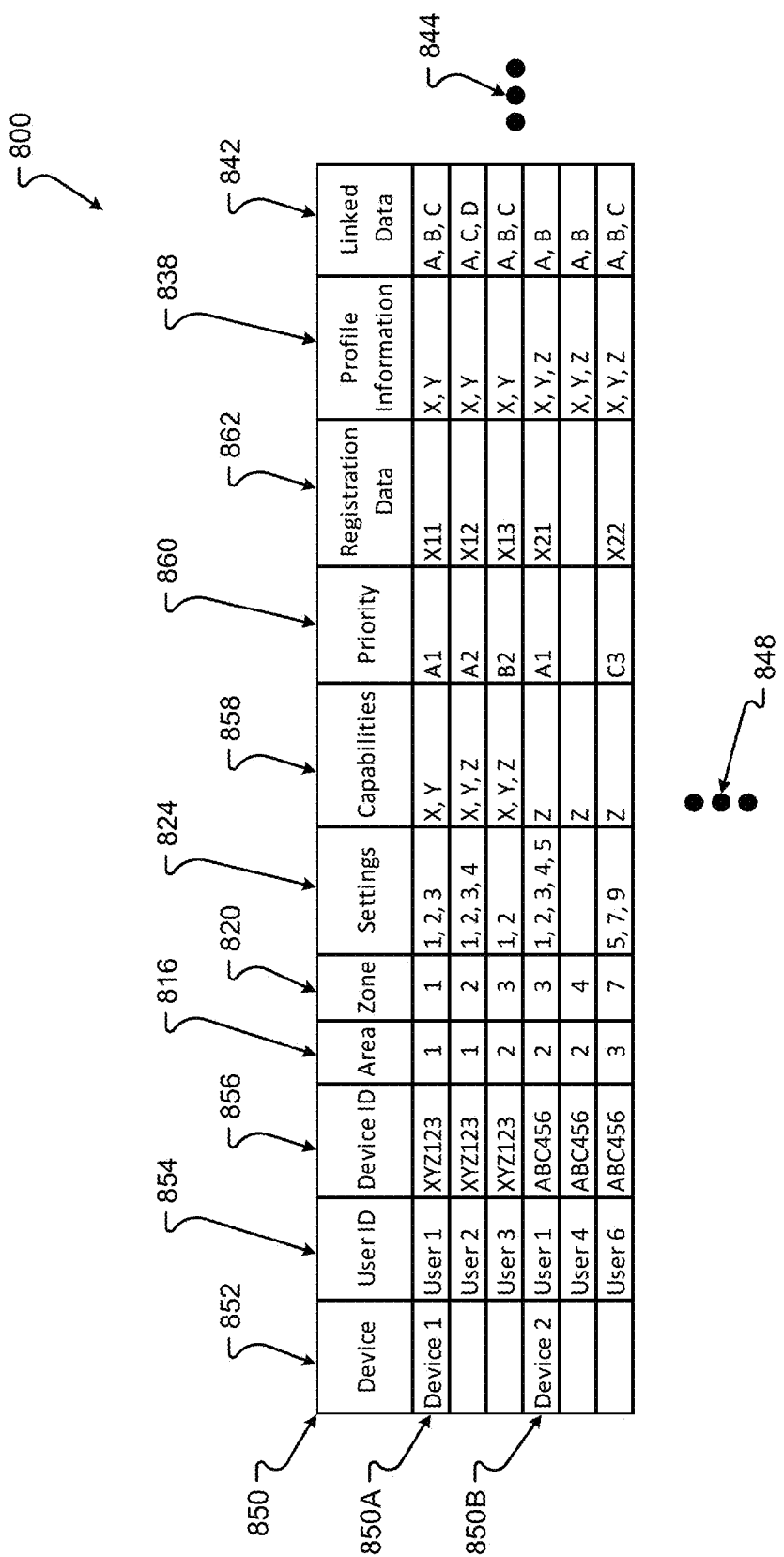
FIG. 8B is a diagram of an embodiment of a data structure for storing information about a device associated with exercise equipment.

An embodiment of a data structure 850 to store information associated with one or more devices is shown in FIG. 8B. The data file 850 may include several portions 820-862 representing different types of data. Each of these types of data may be associated with a device, as shown in portion 852.

There may be one or more device records 850 and associated data stored within the data file 850. As provided herein, the device 124, 126 may be any device that is associated with the treadmill 102. For example, a device may be associated with a treadmill 102 when that device is physically connected to the treadmill 102. As another example, a device may be associated with a treadmill 102 when the device registers with the treadmill 102. Registration may include pairing the device with the treadmill 102 and/or one or more of the exercise systems. In some cases, the registration of a device with a treadmill 102 may be performed manually and/or automatically. An example of automatic registration may include detecting, via one or more of the exercise systems, that a device is within physical proximity of the treadmill 102. Upon detecting that the device is physically near the treadmill 102, the exercise system may identify the device and determine whether the device is or should be registered. Registration may be performed with treadmill 102 via providing a unique code to the treadmill 102 and/or at least one of the exercise systems.

The device may be identified in portion 856. Among other things, the device identification may be based on the hardware associated with the device (e.g., Media Access Control (MAC) address, Burned-In Address (BIA), Ethernet Hardware Address (EHA), physical address, hardware address, and the like).

Optionally, a device may be associated with one or more users. For example, a tablet and/or graphical user interface (GUI) associated with the treadmill 102 may be used by multiple members of a family. The user of the device may be identified in portion 854, shown in FIG. 8B. For the device, the user identification portion 854 may include a set of one or more features that may identify a particular user. These features may be the physical characteristics of the person that may be identified by facial recognition, or some other type of system, associated with the device and/or the treadmill 102. Optionally, the user may provide a unique code to the device, or provide some other type of data, that allows the device to identify the user. The features or characteristics of the user are then stored in portion 854.

Each device identified in the device identification portion 856 may have a different set of settings for each area 408 and/or each zone 412, and/or each user of the device. Thus, each set of settings may also be associated with a predetermined zone 412, area 408, and/or user. The zone 412 is stored in portion 820 and the area 408 is stored in portion 816.

One or more settings may be stored in portion 824. These settings 824 may be similar and/or identical to those previously described. Further, the settings 824 may also provide for how a device is configured for a particular user. Each setting 824 may be associated with a different area 408 or zone 412. Thus, there may be more restrictive settings 824 (e.g., restricted multimedia, texting, limited access to device functions, and the like).

Optionally, the capabilities of a device may be stored in portion 858. Examples of device capabilities may include, but are not limited to, a communications ability (e.g., via wireless network, EDGE, 3G, 4G, LTE, wired, Bluetooth®, Near Field Communications (NFC), Infrared (IR), etc.), hardware associated with the device (e.g., cameras, gyroscopes, accelerometers, touch interface, processor, memory, display, etc.), software (e.g., installed, available, revision, release date, etc.), firmware (e.g., type, revision, etc.), operating system, system status, and the like. Optionally, the various capabilities associated with a device may be controlled by one or more of the exercise systems provided herein. Among other things, this control allows the treadmill 102 to leverage the power and features of various devices to collect, transmit, and/or receive data.

One or more priorities may be stored in portion 860. The priority may correspond to a value, or combination of values, configured to determine how a device interacts with the treadmill 102 and/or its various systems. The treadmill 102 may determine that, although other devices are found near or connected with the treadmill 102, the device, having the highest priority, controls features associated with the treadmill 102. These features may include exercise control features, critical and/or non-critical systems, communications, and the like. Additionally or alternatively, the priority may be based on a particular user associated with the device. Optionally, the priority may be used to determine which device will control a particular signal in the event of a conflict.

Registration data may be stored in portion 862. As described above, when a particular device registers with a treadmill 102, data related to the registration may be stored in the registration data portion 862. Such data may include, but is not limited to, registration information, registration codes, initial registration time, expiration of registration, registration timers, and the like. Optionally, one or more systems of the treadmill 102 may refer to the registration data portion 862 to determine whether a device has been previously registered with the treadmill 102. As shown in FIG. 8B, User 4 of Device 2 has not been registered. In this case, the registration data field 862, for this user, may be empty, contain a null value, or other information/indication that there is no current registration information associated with the user.

Additionally or alternatively, the data structure 800 may include a profile information portion 838 and/or a linked data portion 842. Although the profile information portion 838 and/or the linked data portion 842 may include different information from that described above, it should be appreciated that the portions 838, 842 may be similar, or identical, to those as previously disclosed.

Figure 8C:
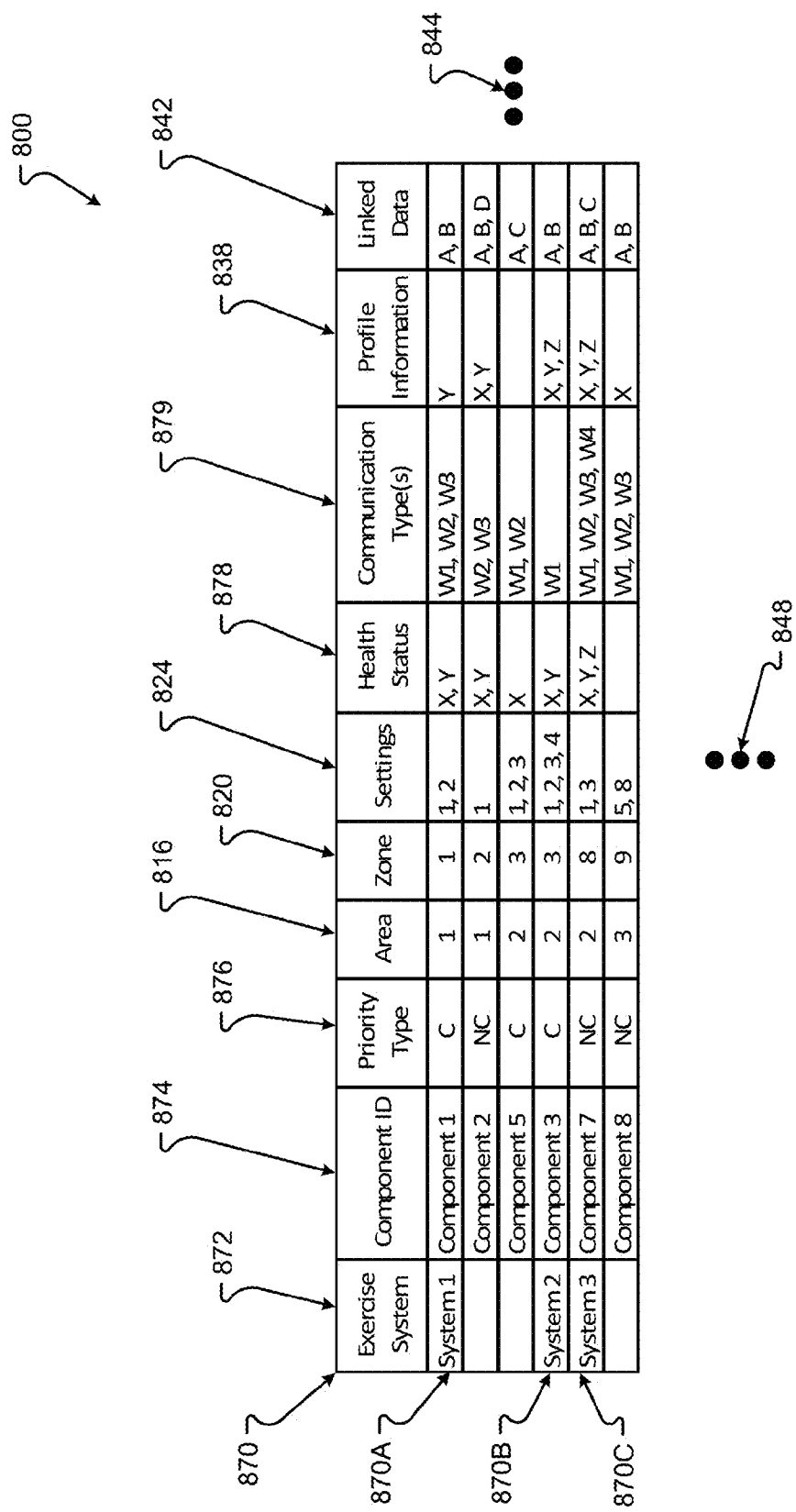
FIG. 8C is a diagram of an embodiment of a data structure for storing information about a system of exercise equipment.

An embodiment of a data structure 870 to store information associated with one or more exercise systems is shown in FIG. 8C. The data file 850 may include several portions 820-859 representing different types of data. Each of these types of data may be associated with an exercise system, as shown in portion 852.

There may be one or more system records 850 and associated data stored within the data file 850. As provided herein, the exercise systems may different types of exercise equipment including the treadmill 102, an exercise cycle, a stair climber, etc. One example of a system associated with the treadmill 102 is the treadmill control system 204. Other systems may include communications subsystems 344, treadmill subsystems 328, and media subsystems 348, to name a few. It should be appreciated that the various systems may be associated with the interior and/or the exterior of the treadmill 102.

Each system may include one or more components. The components may be identified in portion 854. Identification of the one or more components may be based on hardware associated with the component. This identification may include hardware addresses similar to those described in conjunction with the devices of FIG. 3. Additionally or alternatively, a component can be identified by one or more signals sent via the component. Such signals may include an Internet Protocol (IP), or similar, address as part of the signal. Optionally, the signal may identify the component sending the signal via one or more of a header, a footer, a payload, and/or an identifier associated with the signal (e.g., a packet of a signal, etc.).

Each system and/or component may include priority type information in portion 856. Among other things, the priority type information stored in portion 856 may be used by the various methods and systems provided herein to differentiate between critical and non-critical systems. Non-limiting examples of critical systems may correspond to those systems used to control the treadmill 102, such as, motor control, speed control, etc. Non-critical systems may include other systems that are not directly related to the control of the treadmill 102. By way of example, non-critical systems may include media presentation, wireless communications, comfort settings systems, and the like. Although examples of critical and/or non-critical systems are provided above, it should be appreciated that the priority type of a system may change (e.g., from critical to non-critical, from non-critical to critical, etc.) depending on the scenario.

Control of each system may be associated with a particular area 408 and/or zone 412 of a view 902. As can be appreciated each system may have a different set of settings for each area 408 and/or each zone 412, and/or each user of the system. Thus, each set of settings may also be associated with a predetermined zone 412, area 408, system, and/or user. The zone 412 is stored in portion 820 and the area 408 is stored in portion 816.

One or more settings may be stored in portion 824. These settings 824 may be similar and/or identical to those previously described. Further, the settings 824 may also provide for how a system is configured for a particular user. Each setting 824 may be associated with a different area 408 or zone 412. Optionally, the settings may not be dependent on a user. For instance, specific areas 408 and/or zones 412 of a treadmill 102 may include different, default, or the same settings based on the information stored in portion 824.

The various systems and/or components may be able to obtain or track health status data of the systems and/or components in portion 878. The health status 878 may include any type of information related to a state of the systems. For instance, an operational condition, manufacturing date, update status, revision information, time in operation, fault status, state of damage detected, inaccurate data reporting, and other types of component/system health status data may be obtained and stored in portion 878.

Each component and/or system may be configured to communicate with users, systems, servers, exercises, third parties, and/or other endpoints via one or more communication type. At least one communication ability and/or type associated with a system may be stored in the communication type portion 879. Optionally, the communication types contained in this portion 879 may be ordered in a preferential order of communication types. For instance, a system may be configured to preferably communicate via a wired communication protocol over one or more wired communication channels (e.g., due to information transfer speeds, reliability, and the like). However, in this instance, if the one or more wired communication channels fail, the system may transfer information via an alternative communication protocol and channel (e.g., a wireless communication protocol and wireless communication channel, etc.). Among other things, the methods and systems provided herein may take advantage of the information stored in the communication type portion 879 to open available communication channels in the event of a communication channel failure, listen on other ports for information transmitted from the systems, provide a reliability rating based on the number of redundant communication types for each component, and more. Optionally, a component or system may be restricted from communicating via a particular communication type. In this example, the component or system may be forced by the treadmill control system 204 to use an alternate communication type where available, cease communications, or store communications for later transfer.

Additionally or alternatively, the data structure 870 may include a profile information portion 838 and/or a linked data portion 842. Although the profile information portion 838 and/or the linked data portion 842 may include different information from that described above, it should be appreciated that the portions 838, 842 may be similar, or identical, to those as previously disclosed.

Figure 8D:
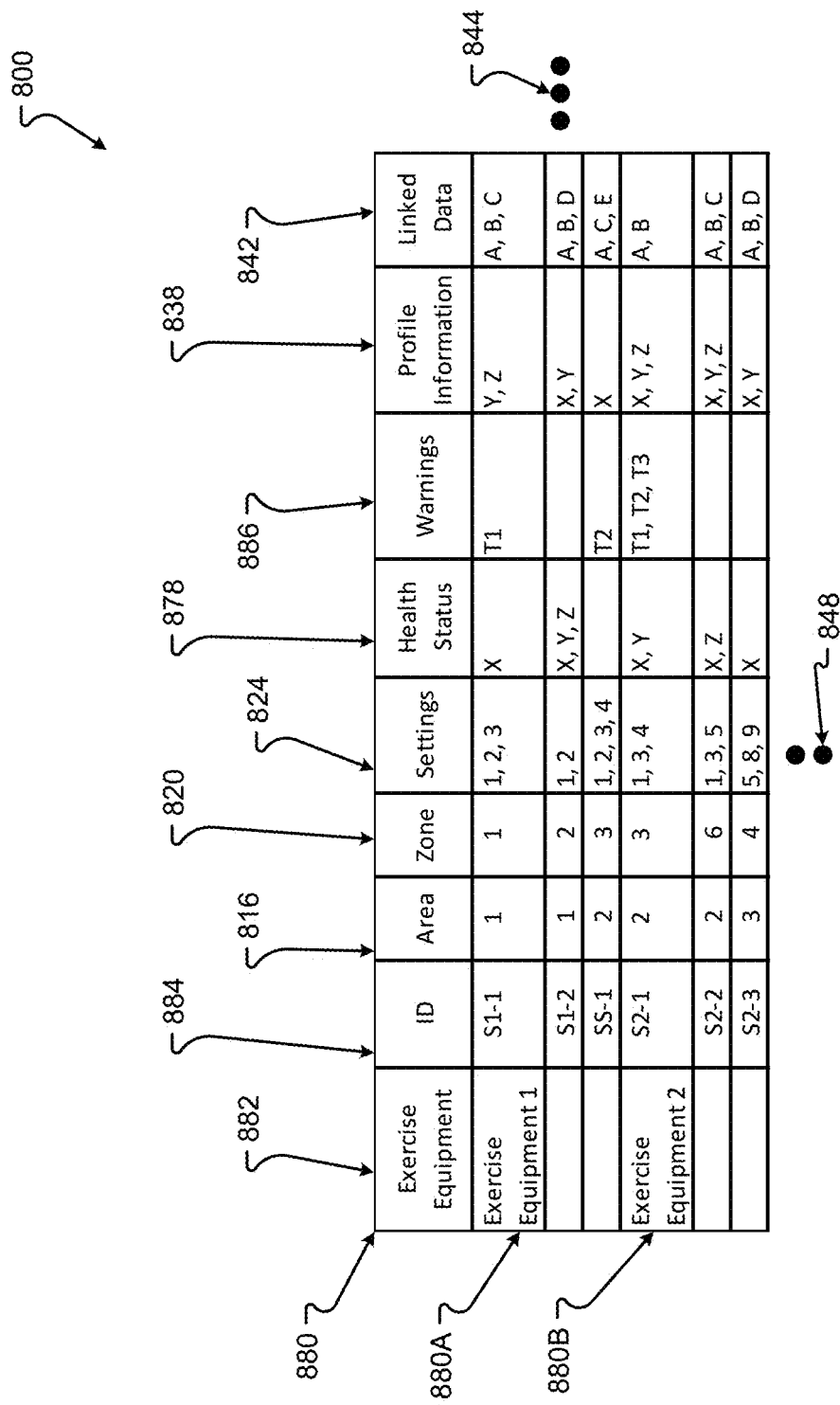
FIG. 8D is a diagram of an embodiment of a data structure for storing information about exercise equipment.

Referring now to FIG. 8D, a data structure 800 is shown optionally. The data file 880 may include several portions 816-886 representing different types of data. Each of these types of data may be associated with an exercise, as shown in portion 882.

There may be one or more exercise records 880 and associated data stored within the data file 882. As provided herein, the treadmill 102 can be any exercise or exercise equipment 102 as provided herein. The treadmill 102 may be identified in portion 882. Additionally or alternatively, the treadmill 102 may be identified by one or more systems and/or subsystems. The various systems of a treadmill 102 may be identified in portion 884. For example, various features or characteristics of the treadmill 102 and/or its systems may be stored in portion 884. Optionally, the treadmill 102 may be identified via a unique code or some other type of data that allows the treadmill 102 to be identified.

Each control for the system may be associated with a particular area 408 and/or zone 412 of a treadmill 102. Among other things, the location of a system may be used to assess a state of the system and/or provide how the system interacts with one or more users of the treadmill 102. As can be appreciated each system may have a different set of settings for each area 408 and/or each zone 412, and/or each user of the system. Thus, each set of settings may also be associated with a predetermined zone 412, area 408, system, and/or user. The zone 412 is stored in portion 820 and the area 408 is stored in portion 816.

One or more settings may be stored in portion 824. These settings 824 may be similar and/or identical to those previously described. Further, the settings 824 may also provide for how an exercise and/or its systems are configured for one or more users. Each setting 824 may be associated with a different area 408 or zone 412. Optionally, the settings may not be dependent on a particular user. For instance, specific areas 408 and/or zones 58 of a treadmill 102 may include different, default, or the same settings based on the information stored in portion 824.

The various systems and/or components may be able to obtain or track health status data of the systems and/or components in portion 858. The health status 858 may include any type of information related to a state of the systems. For instance, an operational condition, manufacturing date, update status, revision information, time in operation, fault status, state of damage detected, inaccurate data reporting, and other types of component/system health status data may be obtained and stored in portion 858.

One or more warnings may be stored in portion 886. The warnings data 8126 may include warning generated by the treadmill 102, systems of the treadmill 102, manufacturer of the exercise, federal agency, third party, and/or a user associated with the exercise. For example, several components of the exercise may provide health status information (e.g., stored in portion 858) that, when considered together, may suggest that the treadmill 102 has suffered some type of damage and/or failure. Recognition of this damage and/or failure may be stored in the warnings data portion 886. The data in portion 886 may be communicated to one or more parties (e.g., a manufacturer, maintenance facility, user, etc.). In another example, a manufacturer may issue a recall notification for a specific treadmill 102, system of a treadmill 102, and/or a component of a treadmill 102. It is anticipated that the recall notification may be stored in the warning data field 886. Continuing this example, the recall notification may then be communicated to the user of the treadmill 102 notifying the user of the recall issued by the manufacturer.

Additionally or alternatively, the data structure 880 may include a profile information portion 838 and/or a linked data portion 842. Although the profile information portion 838 and/or the linked data portion 842 may include different information from that described above, it should be appreciated that the portions 838, 842 may be similar, or identical, to those as previously disclosed.

Figure 9:
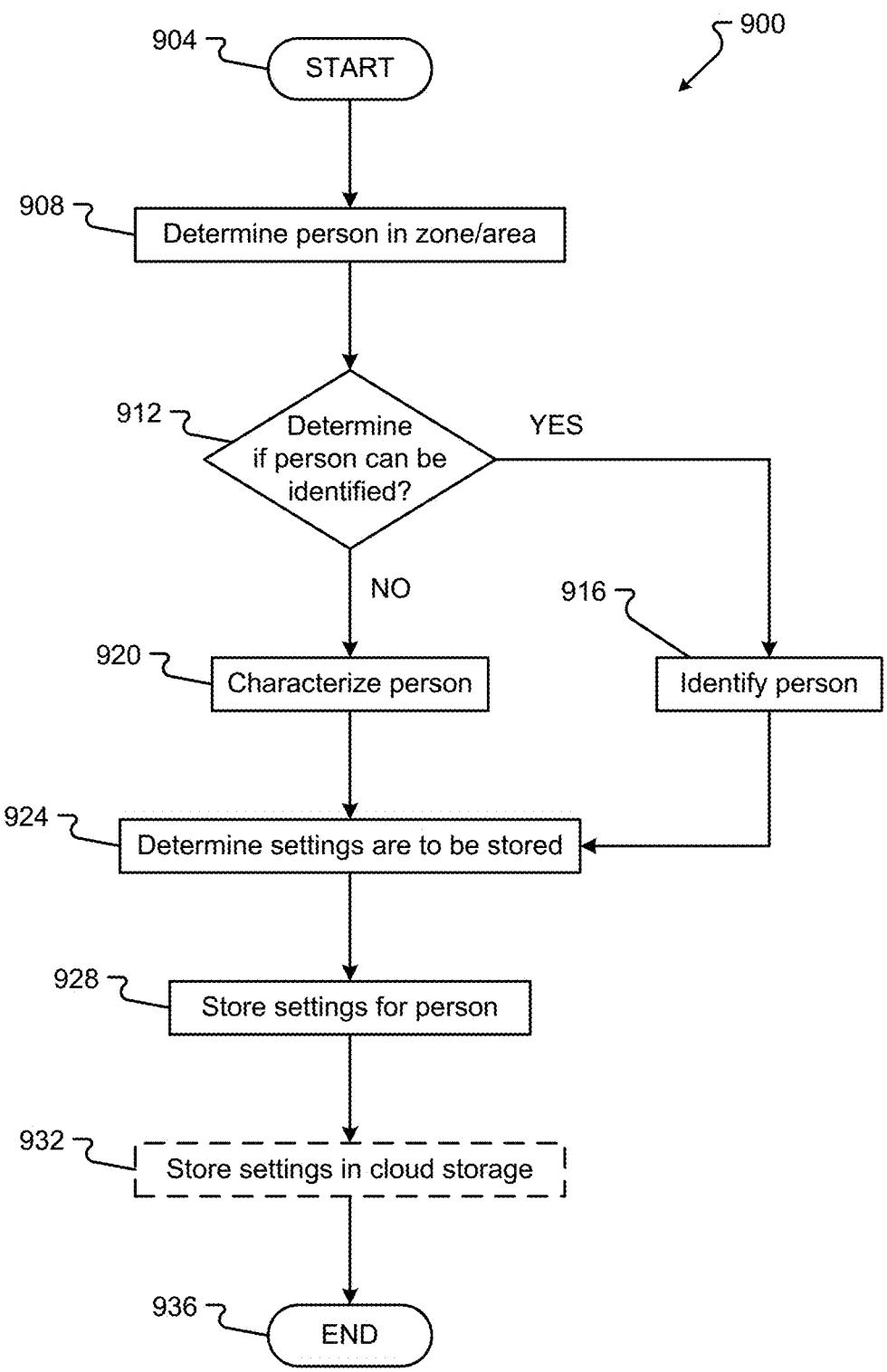
FIG. 9 is a flow or process diagram of a method for storing one or more settings associated with a user.

An embodiment of a method 900 for storing settings for a user 120 associated with treadmill 102 is shown in FIG. 9. While a general order for the steps of the method 900 is shown in FIG. 9, the method 900 can include more or fewer steps or can arrange the order of the steps differently than those shown in FIG. 9. Generally, the method 900 starts with a start operation 904 and ends with an end operation 936. The method 900 can be executed as a set of computer-executable instructions executed by a computer system and encoded or stored on a computer readable medium. Hereinafter, the method 900 will be explained with reference to the systems, components, modules, software, data structures, user interfaces, etc. described in conjunction with FIGS. 1-8.

A person may enter the exercise environment 100. One or more sensors 242 may then identify that a person 120 is preparing to use the treadmill 102, in step 908. For example, sensors 242 may determine that a person is in the view 192. Further, the sensors 242 may determine weight has been applied to a platform 104 of the treadmill 102. The amount of weight may fall within predetermined parameters (e.g., over a threshold, in a specific range, etc.). This weight may then be determined to be a person by one or more optical or other sensors 242. The treadmill control system 204 may then determine that a person is in a certain zone 412 or area 408. For example, the sensors 242 may send signals to the exercise controls system 204 that an event has occurred. This information may be sent to the exercise control system processor 304 to determine the zone 412 and area 408 where the event occurred. Further, the treadmill control system 204 may then identify the person, in step 912.

The treadmill control system 204 can receive the information from the sensors 242 and use that information to search the database 800 that may be stored within the system data 208. The sensor data may be compared to ID characteristics 826 to determine if the person has already been identified. The treadmill control system 204 may also send the characteristic data from the sensors to the communication network 224 to a server 228 to compare the sensor data to stored data 232 that may be stored in a cloud system. The person's features can be compared to stored features 812 to determine if the person in the treadmill 102 can be identified.

If the person has been identified previously and their characteristics stored in portion 812, the method 900 proceeds YES to step 916 where that person may be identified. In identifying a person, the information associated with that person 840 may be retrieved and provided to the treadmill control system 204 for further action. If a person cannot be identified by finding their sensor characteristics in portion 812, the method 900 proceeds NO to step 920. In step 920, the treadmill control system 204, using an application, may create a new record in table 800 for the user. This new record may store a user identifier and their characteristics 812. It may also store the area 408 and zone 412 in data portions 816 and 820. The new record may then be capable of receiving new settings data for this particular user. In this way, the treadmill 102 can automatically identify or characterize a person so that settings may be established for the person in the treadmill 102.

The I/O module 312 may then determine if settings are to be stored, in step 924. Settings might be any configuration of the treadmill 102 that may be associated with the user. The determination may be made after receiving a user input from the user. For example, the user may make a selection on a touch sensitive display indicating that settings currently made are to be stored. In other situations, a period of time may elapse after the user has made a configuration. After determining that the user is finished making changes to the settings, based on the length of the period of time since the setting was established, the treadmill control system 204 can save the setting. Thus, the treadmill control system 204 can make settings automatically based on reaching a steady state for settings for user.

The treadmill control system 204 may then store the settings for the person, in step 928. The user interaction subsystem 332 can make a new entry for the user 808 in data structure 804. The new entry may be either a new user or a new settings listed in 824. The settings may be stored based on the area 408 and zone 412. As explained previously, the settings can be any kind of configuration of the treadmill 102 that may be associated with the user in that area 408 and the zone 412.

The settings may also be stored in cloud storage, in step 932. Thus, the treadmill control system 204 can send the new settings to the server 228 to be stored in storage 232. In this way, these new settings may be ported to other exercise equipment for the user. Further, the settings in storage system 232 may be retrieved, if local storage does not include the settings in storage system 208.

Additionally or alternatively, the settings may be stored in profile data 252. As provided herein, the profile data 252 may be associated with one or more devices 126, 124, servers 228, exercise control systems 204, and the like. Optionally, the settings in profile data 252 may be retrieved in response to conditions. For instance, the settings may be retrieved from at least one source having the profile data if local storage does not include the settings in storage system 208. As another example, a user 120 may wish to transfer settings stored in profile data 252 to the system data 208. In any event, the retrieval and transfer of settings may be performed automatically via one or more devices 126, 124, associated with the treadmill 102.

Figure 10:
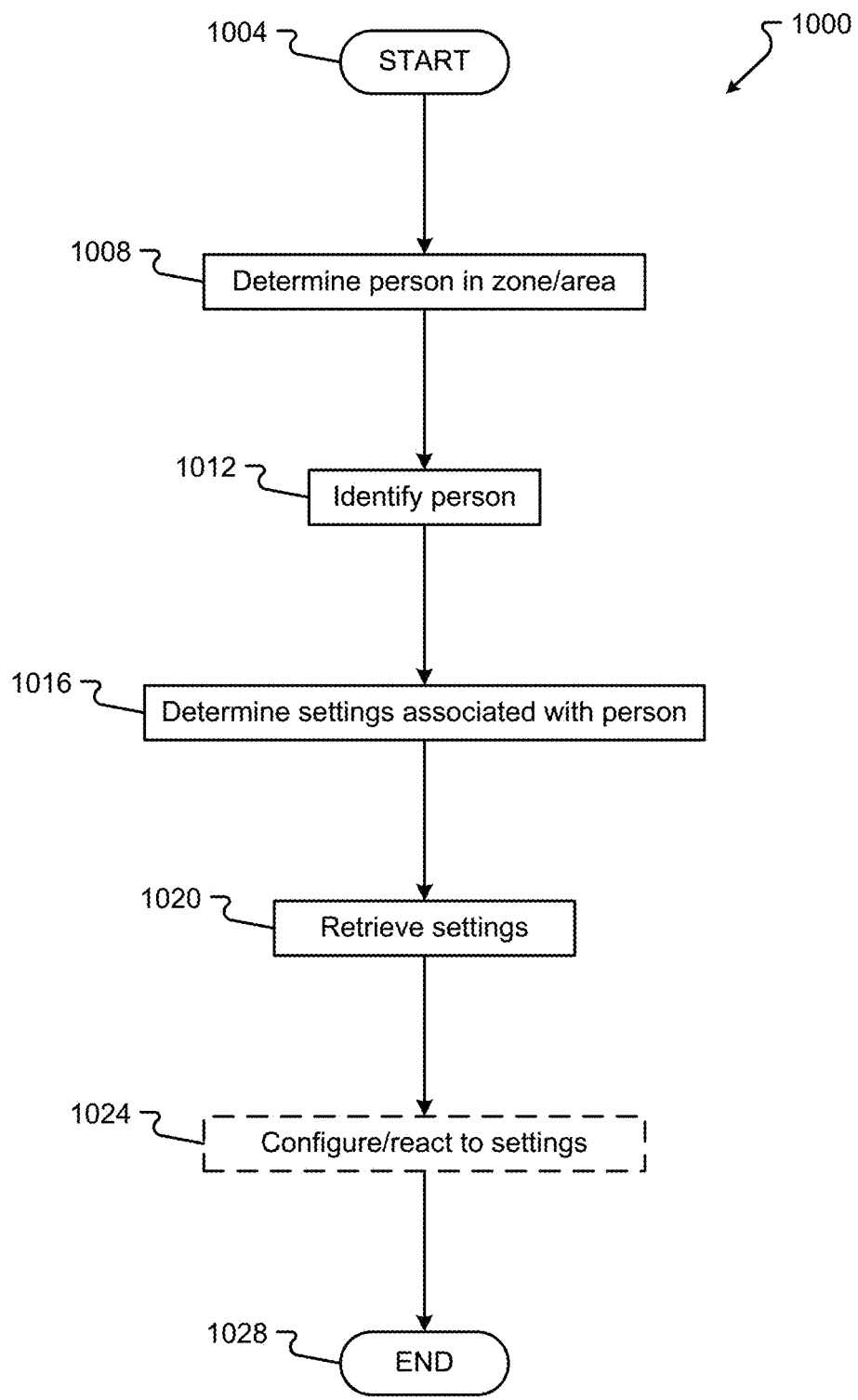
FIG. 10 is a flow or process diagram of a method for establishing one or more settings associated with a user.

An embodiment of a method 1000 to configure the treadmill 102 based on stored settings is shown in FIG. 10. A general order for the steps of the method 1000 is shown in FIG. 10. Generally, the method 1000 starts with a start operation 1004 and ends with an end operation 1028. The method 1000 can include more or fewer steps or can arrange the order of the steps differently than those shown in FIG. 10. The method 1000 can be executed as a set of computer-executable instructions executed by a computer system and encoded or stored on a computer readable medium. Hereinafter, the method 1000 shall be explained with reference to the systems, components, modules, software, data structures, user interfaces, etc. described in conjunction with FIGS. 1-9.

The treadmill control system 204 can determine if a person is in a zone 412 or area 408, in step 1008. This determination may be made by receiving data from one or more sensors 242. The treadmill 102 can use facial recognition, weight sensors, heat sensors, or other sensors to determine whether a person is occupying a certain zone 412.

Using the information from the sensors 242, the treadmill control system 204 can identify the person, in step 1012. The treadmill control system 204 can obtain characteristics for the user currently occupying the zone 412 and compare those characteristics to the identifying features in portion 812 of data structure 804. Thus, the settings in portion 824 may be retrieved by identifying the correct zone 412, area 408, and/or characteristics for the user.

The treadmill control system 204 can first determine if there are settings associated with the identified person for that zone 412 and/or area 408, in step 1016. After identifying the user by matching characteristics with the features in portion 812, the treadmill control system 204 can determine if there are settings for the user for the area 408 and zone 412 the user currently occupies. If there are settings, then the treadmill control system 204 can make the determination that there are settings in portion 824, and the treadmill control system 204 may then read and retrieve those settings, in step 1020. The settings may be then used to configure or react to the presence of the user, in step 1024. Thus, these settings may be obtained to change the configuration of the treadmill 102, for example, how the position of the platform is set, how the console or display is configured, how the cooling is configured, how the radio is configured, or how other different configurations are made.

Figure 11:
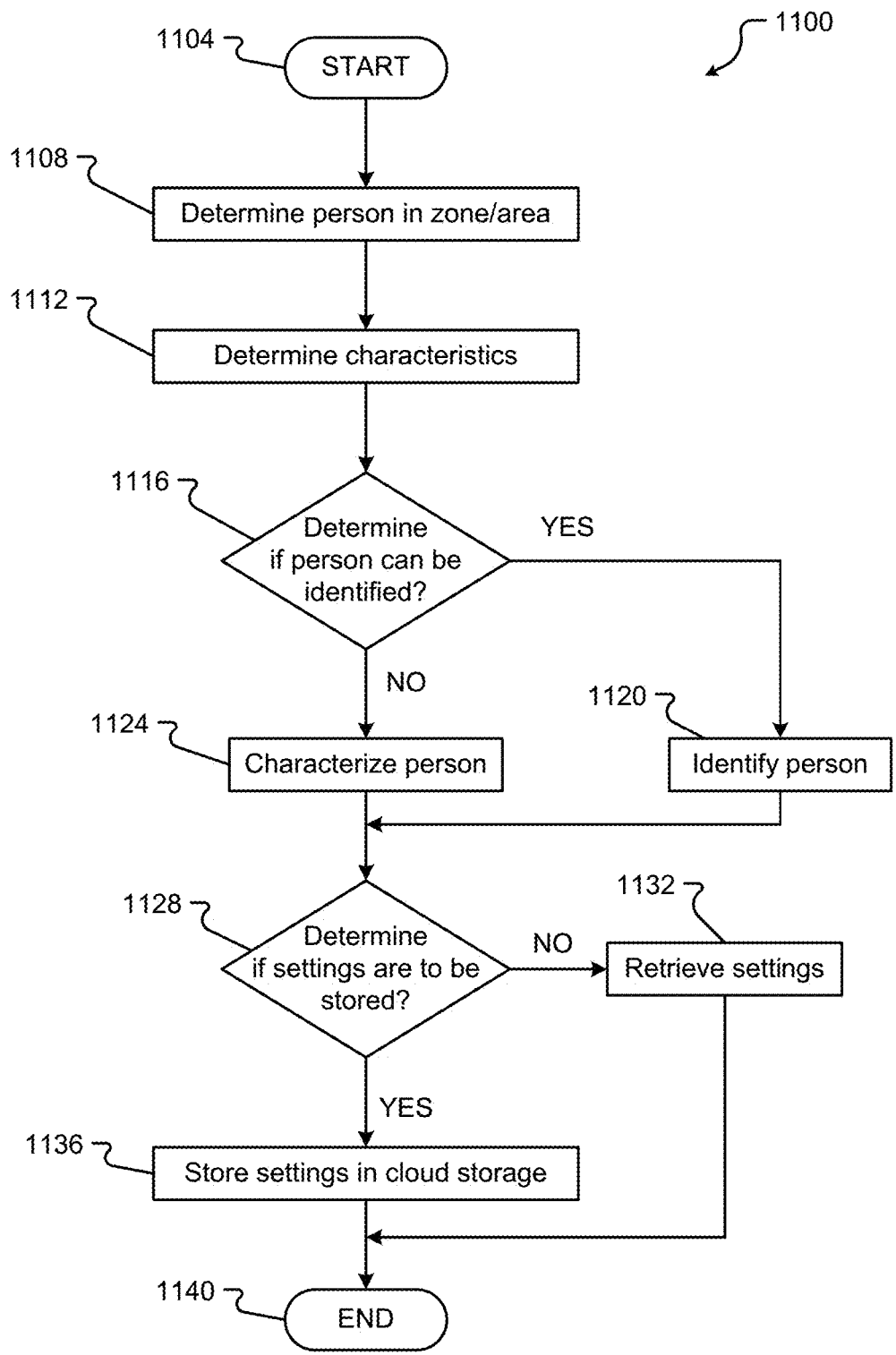
FIG. 11 is a flow or process diagram of a method for storing one or more settings associated with a user.

Embodiments of a method 1100 for storing settings in cloud storage are shown in FIG. 11. A general order for the steps of the method 1100 is shown in FIG. 11. Generally, the method 1100 starts with a start operation 1104 and ends with an end operation 1140. The method 1100 can include more or fewer steps or can arrange the order of the steps differently than those shown in FIG. 11. The method 1100 can be executed as a set of computer-executable instructions executed by a computer system and encoded or stored on a computer readable medium. Hereinafter, the method 1100 shall be explained with reference to the systems, components, modules, software, data structures, user interfaces, etc. described in conjunction with FIGS. 1-10.

The treadmill control system 204 can determine if a person is in a zone 412 or area 408, in step 1108. As explained previously, the treadmill control system 204 can receive exercise sensor data from exercise sensors 242 that show a person has occupied a zone 412 or an area 408 of the treadmill 102. Using the exercise sensor data, the treadmill control system 204 can determine characteristics of the person, in step 1112. These characteristics are compared to the features in portion 812 of the data structure 804. From this comparison, the treadmill control system 204 can determine if the person is identified within the data structure 804, in step 1116. If there is a comparison and the person can be identified, the method 1100 proceeds YES to step 1120. However, if the person cannot be identified, the method 1100 proceeds NO, to step 1124.

In step 1120, the person is identified in portion 808 by the successful comparison of the characteristics and the features 812. It should be noted that there may be a degree of variability between the characteristics and the features in portion 812. Thus, the comparison may not be an exact comparison but may use methods known in the art to make a statistically significant comparison between the characteristics received from the sensors 242 and the features stored in portion 812. In step 1124, the characteristics received from sensors 242 are used to characterize the person. In this way, the received characteristics may be used as an ID, in portion 812, for a new entry for a new user in portion 808.

The user may make one or more settings for the treadmill 102. The treadmill control system 204 may determine if the settings are to be stored, in step 1128. If the settings are to be stored, the method 1100 proceeds YES to step 1136. If the settings are not to be stored or if there are no settings to be stored, the method 1100 proceeds NO to step 1132. In step 1132, the treadmill control system 204 can retrieve the settings in the portion 824 of the data structure 804. Retrieval of the settings may be as described in conjunction with FIG. 14. If settings are to be stored, the treadmill control system 204 can send those settings to server 228 to be stored in data storage 232, in step 1136. Data storage 232 acts as cloud storage that can be used to retrieve information on the settings from other exercises or from other sources. Thus, the cloud storage 232 allows for permanent and more robust storage of user preferences for the settings of the treadmill 102.

Figure 12:
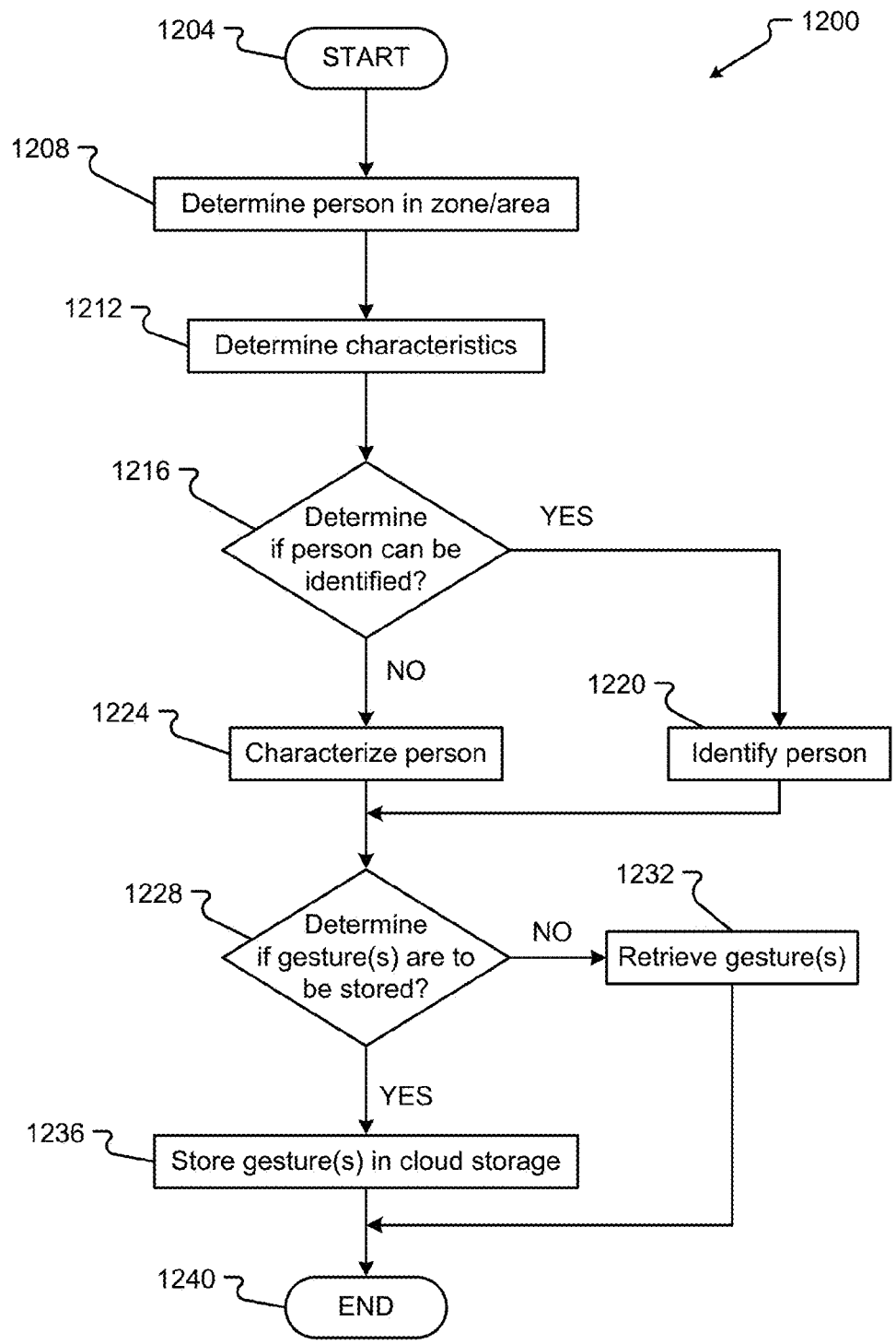
FIG. 12 is a flow or process diagram of a method for storing one or more gestures associated with a user.

An embodiment of a method 1200 for storing gestures associated with the user is shown in FIG. 12. A general order for the steps of the method 1200 is shown in FIG. 12. Generally, the method 1200 starts with a start operation 1204 and ends with an end operation 1240. The method 1200 can include more or fewer steps or can arrange the order of the steps differently than those shown in FIG. 12. The method 1200 can be executed as a set of computer-executable instructions executed by a computer system and encoded or stored on a computer readable medium. Hereinafter, the method 1200 shall be explained with reference to the systems, components, modules, software, data structures, user interfaces, etc. described in conjunction with FIGS. 1-11.

Exercise control system 204 may receive sensor data from sensors 242 to determine a person is occupying a zone 412 in an area 408 of the treadmill 102, in step 1208. The sensor data may provide characteristics for the person, in step 1212. The treadmill control system 204 may then use the characteristics to determine if the person can be identified, in step 1216. The treadmill control system 204 may compare the characteristics to the features in portion 812 for the people having been recognized and having data associated therewith. If a comparison is made between the characteristics and the features in portion 812, the person can be identified, and the method 1200 proceeds YES to step 1220. If there is no comparison, the method 1200 may proceed NO to step 1224. In step 1220, the person may be identified by the treadmill control system 204. Thus, the person's features and associated data record 840 may be determined and the user identified in portion 808. If the person is not identified, the treadmill control system 204 can characterize the person in step 1224 by establishing a new record in data structure 804 using the characteristics, received from the sensors 242, for the features in portion 812.

Thereinafter, the treadmill control system 204 may determine if gestures are to be stored and associated with the user, in step 1228. The treadmill control system 204 may receive user input on a touch sensitive display or some other type of gesture capture region which acknowledges that the user wishes to store one or more gestures. Thus, the user may create their own gestures such as those described in conjunction with FIGS. 7A-7K. These gestures may then be characterized and stored in data structure 804. If there are gestures to be stored, the method 1200 proceeds YES to step 1236. If gestures are not to be stored the method 1200 may proceed NO to step 1232.

In step 1232, the treadmill control system 204 can retrieve current gestures from portion 832, which are associated with user 840. These gestures may be used then to configure how the treadmill 102 will react if a gesture is received. If gestures are to be stored, the treadmill control system 204 may store characteristics, in step 1236, as received from sensor 242 or from one more user interface inputs. These characteristics may then be used to create the stored gestures 832, in data structure 804. The characteristics may include what the gesture looks like or appears and also what affect the gesture should have. This information may then be used to change the configuration or operation of the treadmill 102 based on the gesture if it is received at a later time.

Figure 13:
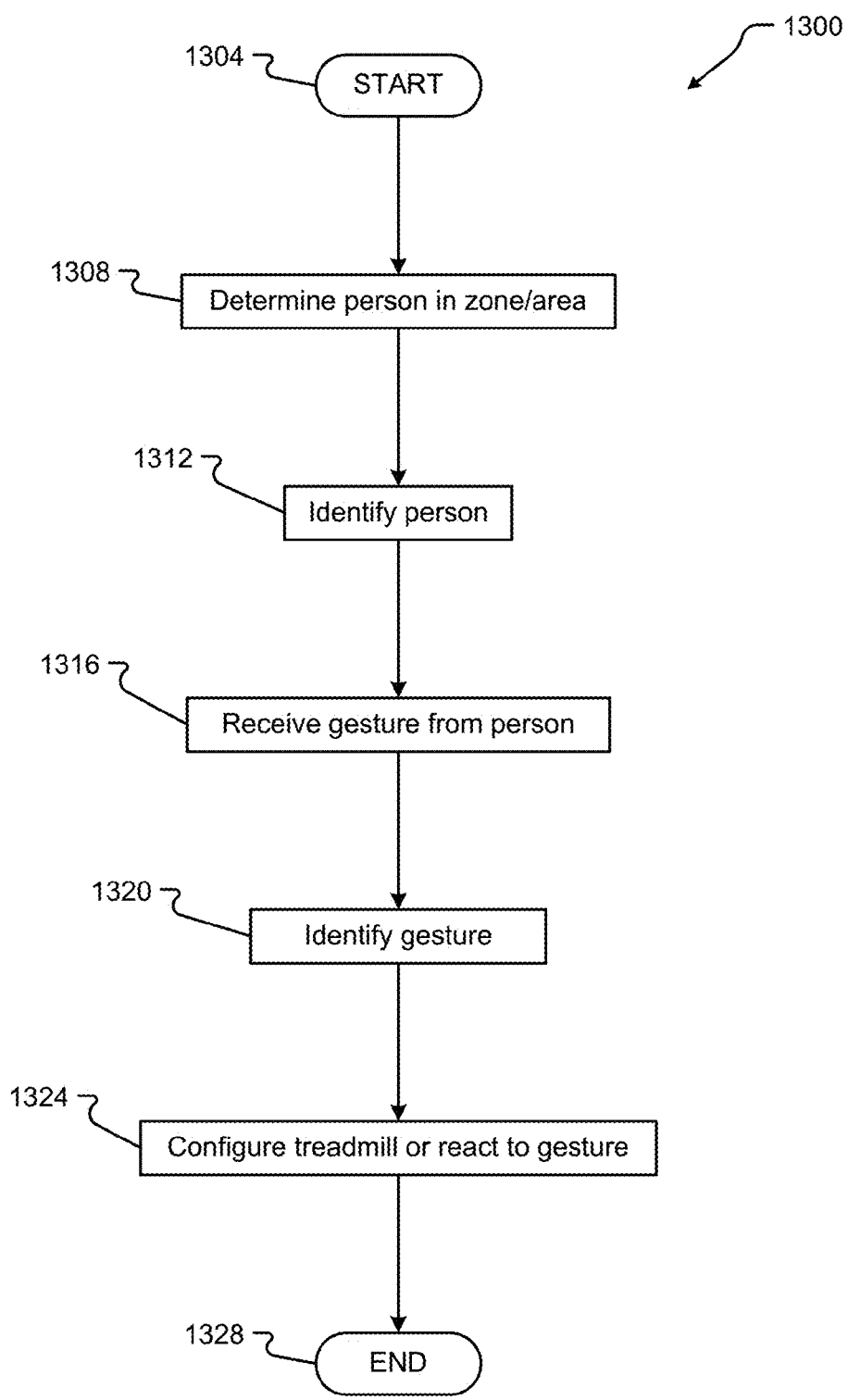
FIG. 13 is a flow or process diagram of a method for reacting to a gesture performed by a user.

An embodiment of a method 1300 for receiving a gesture and configuring the treadmill 102 based on the gesture may be as provided in FIG. 13. A general order for the steps of the method 1300 is shown in FIG. 13. Generally, the method 1300 starts with a start operation 1304 and ends with an end operation 1328. The method 1300 can include more or fewer steps or can arrange the order of the steps differently than those shown in FIG. 13. The method 1300 can be executed as a set of computer-executable instructions executed by a computer system and encoded or stored on a computer readable medium. Hereinafter, the method 1300 shall be explained with reference to the systems, components, modules, software, data structures, user interfaces, etc. described in conjunction with FIGS. 1-12.

A treadmill control system 204 can receive sensor data from sensors 242. The exercise sensor data can be used by the treadmill control system 204 to determine that a person is in a zone 412 or area 408, in step 1308. The exercise sensor data may then be used to compare against feature characteristics 812 to identify a person, in step 1312. The treadmill control system 204 thereinafter may receive a gesture, in step 1316. The gesture may be perceived by exercise sensors 242 or received in a gesture capture region. The gesture may be as described in conjunction with FIGS. 7A-7K. Upon receiving the gesture, the treadmill control system 204 can compare the gesture to gesture characteristics in portion 832, in step 1320. The comparison may be made so that a statistically significant correlation between the sensor data or gesture data and the gesture characteristic 832 is made. Upon identifying the gesture, the treadmill control system 204 can configure the treadmill 102 and/or react to the gesture, in step 1324. The configuration or reaction to the gesture may be as prescribed in the gesture characteristic 832.

Figure 14:
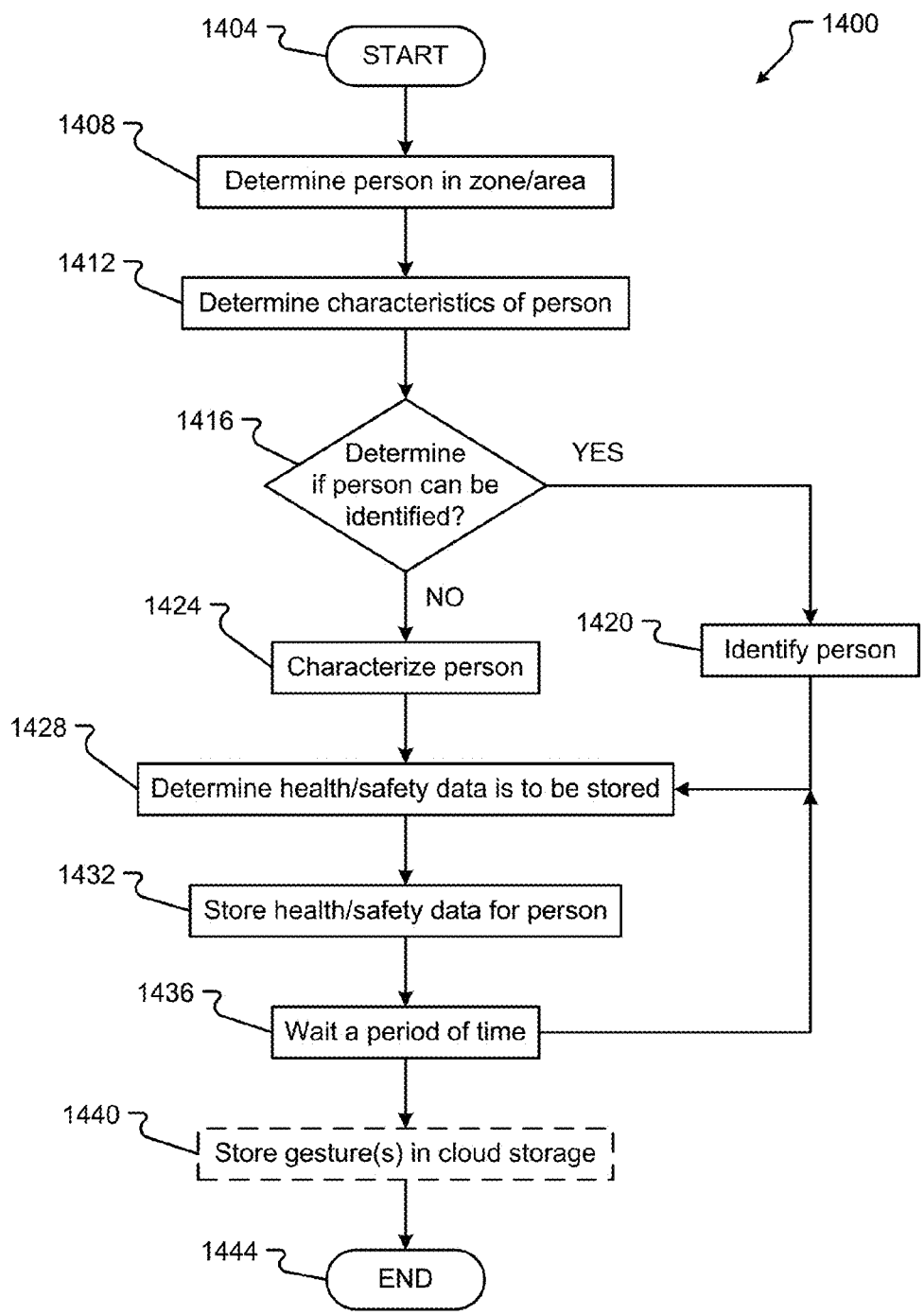
FIG. 14 is a flow or process diagram of a method for storing health data associated with a user.

An embodiment of a method 1400 for storing health data may be as shown in FIG. 14. A general order for the steps of the method 1400 is shown in FIG. 14. Generally, the method 1400 starts with a start operation 1404 and ends with an end operation 1444. The method 1400 can include more or fewer steps or can arrange the order of the steps differently than those shown in FIG. 14. The method 1400 can be executed as a set of computer-executable instructions executed by a computer system and encoded or stored on a computer readable medium. Hereinafter, the method 1400 shall be explained with reference to the systems, components, modules, software, data structures, user interfaces, etc. described in conjunction with FIGS. 1-13.

Exercise control system 204 can receive sensor data from sensors 242. The sensor data may be used to determine that a person is in a zone 412 or area 408, in step 1408. The sensor data may then be used to determine characteristics of the person, in step 1412. From the characteristics, the treadmill control system 204 can determine if a person may be identified in data structure 804, in step 1416. If it is determined that the person can be identified in step 1416, the method 1400 proceeds YES to step 1420. If the person cannot be identified, the method 1400 proceeds NO to step 1424. A person may be identified by matching the characteristics of a person from the sensor data to the features shown in portion 812. If these comparisons are statistically significant, the person may be identified in portion 808, in step 1420. However, if the person is not identified in portion 808, the treadmill control system 204 can characterize the person using the exercise sensor data, in step 1424. In this way, the treadmill control system 204 can create a new record for a new user in data structure 804.

Thereinafter, the treadmill control system 204 may receive health and/or safety data from the exercise sensors 242, in step 1428. The treadmill control system 204 can determine if the health or safety data is to be stored, in step 1432. The determination is made as to whether or not there is sufficient health data or safety parameters, in portion 828 and 836, to provide a reasonable baseline data pattern for the user 840. If there is data to be received and stored, the treadmill control system 204 can store the data for the person in portions 828 and 836 of the data structure 804, in step 1432.

The treadmill control system 204 may then wait a period of time, in step 1436. The period of time may be any amount of time from seconds to minutes to days. Thereinafter, the treadmill control system 204 can receive new data from exercise sensors 242, in step 1428. Thus, the treadmill control system 204 can receive data periodically and update or continue to refine the health data and safety parameters in data structure 804. Thereinafter, the treadmill control system 204 may optionally store the health and safety data in cloud storage 232 by sending it through the communication network 224 to the server 228, in step 1440.

An embodiment of a method 1500 for monitoring the health of a user may be as shown in FIG. 15. A general order for the steps of the method 1500 is shown in FIG. 15. Generally, the method 1500 starts with a start operation 1504 and ends with an end operation 1528. The method 1500 can include more or fewer steps or can arrange the order of the steps differently than those shown in FIG. 15. The method 1500 can be executed as a set of computer-executable instructions executed by a computer system and encoded or stored on a computer readable medium. Hereinafter, the method 1500 shall be explained with reference to the systems, components, modules, software, data structures, user interfaces, etc. described in conjunction with FIGS. 1-14.

The treadmill control system 204 can receive health data from sensors 242. The health data may be received in step 1508. The treadmill control system 204 may then compare the received health data to stored health parameters in portion 828 or portion 836, in step 1512. The comparison may check if there is statistically significant separation or disagreement between the received health data and the stored health data. Thus, the treadmill control system 204 can make a health comparison of the user based on a baseline of health data previously stored. A statistically significant comparison may include determining if there are any parameters more than three standard deviations from the average or norm, any parameter that is increasing or decreasing over a period of eight different measurements, a measurement that is more than two standard deviations from the norm more than three measurements consecutively, or other types of statistical comparisons.

If the treadmill control system 204 determines that measured health parameter does deviate from the norm, the treadmill control system 204 can determine whether the health data is within acceptable limits, in step 1516. If the health data is within acceptable limits, the method 1500 proceeds YES back to receiving new health data, in step 1508. In this way, the health data is periodically or continually monitored to ensure that the user is in a healthy state and able to exercise. If the health data is not within acceptable parameters, the method 1500 may proceed NO to step 1524 where the treadmill control system 204 may react to the change in the health data. The reaction may include any measure to provide for the safety of the user, such as stopping the exercise, alerting paramedics or a hospital, alerting the user with an alarm or other noise, or performing some other function that may help maintain the health or safety of the user.

The health data received may be a reaction from the user. For example, the user may call for help or ask the exercise for assistance. For example, the user may say that they are having a medical emergency and ask the treadmill to perform some function to help. The function to help may include calling for emergency assistance.

Figure 16:
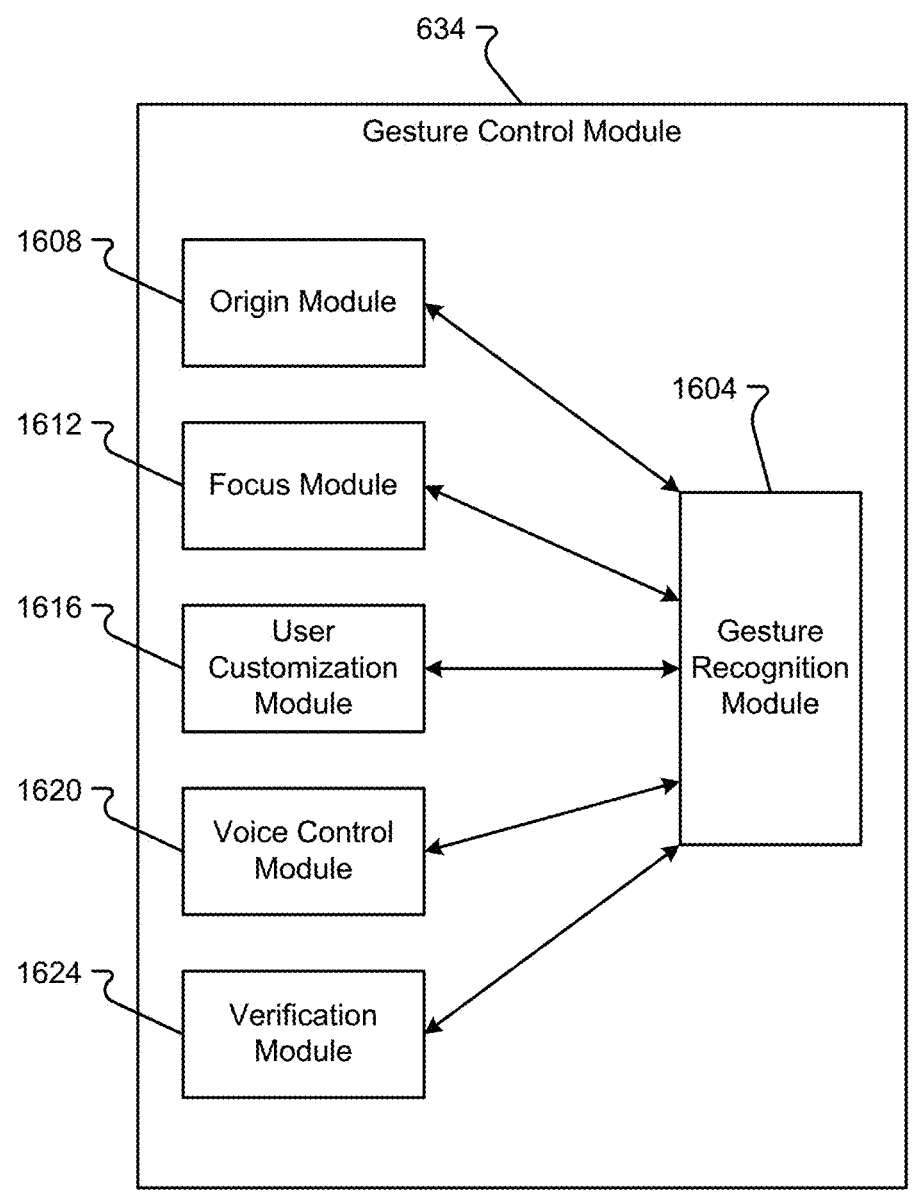
FIG. 16 is a block diagram of an embodiment of a gesture control module.

An embodiment of a gesture control module 634 is shown in FIG. 16. The gesture control module 634 may be hardware, software, or a combination of hardware and software. In one situation, the gesture control module 634 may be part of the user and device interaction subsystem 352, which is described in conjunction with FIG. 3. In other situations, the gesture control module 634 may be a desktop plug-in.

The gesture control module 634 can include one or more modules. The module may include one or more of, but are not limited to, an origin module 1608, a focus module 1612, a user customization module 1616, a voice control module 1620, a verification module 1624, and/or a gesture recognition module 1604. Each of these different modules may be described hereinafter. It should be noted that the modules 1604 through 1624 appear to be included with the gesture control module 634, but may be separate functions embodied in another part of the treadmill control system 204.

The origin module 1608 is generally operable to determine the origin of a gesture. The origin of the gesture may be the same as the location of the person providing the gesture, or may be a different zone 412, a different area 408, a different location within a zone 412 or area 408, or on a console or user interface for a device 124,126 that is near the person. Generally, the origin module 1608 receives exercise sensor data from one or more exercise sensors 242. The exercise sensors 242 may be as described in conjunction with FIG. 2 and FIG. 5. Based on which sensors provide information, the origin module 1608 can identify and determine where the gesture is provided. For example, if two sensors, within a first zone 412A, determine that a gesture has been made, the origin module 1608 may be able to determine that the gesture originates in zone A 512A. It may be possible for the origin module 1608 to determine a location of the gesture within a zone 412 or area 408. Thus, beyond just determining that the gesture happened within the more general zone 412 or area 408, the origin module 1608 can determine that the gesture occurred within a particular quadrant or portion of a zone 412 or area 408.

Further, the origin module 1608 may determine upon which console or devices 124, 126 on the user interface of the device 124, 126 in which the gesture originates. With gestures that includes a tactile input on a touch screen or other electromechanical device, the origin module 1608 can determine upon which console or device input the gesture originated. Gestures may also be given as other types of inputs that may not have a specific device 124, 126, but may be input by a device, such as a mobile device, may be input onto a surface and then recognized by one or more sensors, may be input either verbally or through other types of physical interaction, or may be input by other different means or methods. Regardless, the origin module 1608 can determine where the gesture is made.

A focus module 1612, similar to an origin module 1608, can determine the place upon which a user desires interaction. Unlike the origin module 1608, the focus module 1612 can determine to which input device a user wishes to interact before that interaction occurs. For example, if a user begins to lean or move an arm towards a device 124, 126, the focus module 1612 may determine, in varying degrees of certainty, to which console or other input device the user desires to interact.

As such, the focus module 1612, similar to the origin module 1608, can obtain sensor data from sensors, as described in conjunction with FIGS. 2 and 5. From the sensor data, the focus module 1612 can determine a location within one or more zones 412 or areas 408 within the exercise that a person occupies. When the user within the zone 412 or area 408 desires to make an interaction, the person may begin to move or make a physical indication of desiring to enter a gesture. The movement may be viewed by the focus module 1612 and interpreted as having a target for a gesture or input. The focus module 1612 may then determine where that target is and provide that information to a gesture recognition module 1604.

A user customization module 1616 can change the way in which gestures may be received by the treadmill control system 204. A user customization module 1616 can update or enact gesture preferences, as delineated by a user profile 840, as described in conjunction with FIG. 8A. The gesture preferences may be specific to an area 408 or zone 412. The gestures 832 can be different for each zone 412 or area 408, and may be different if the user makes a gesture while occupying one zone 412 or area 408 but makes the gesture in a different zone 412 or area 408. Further, a user customization module 1616 can also update audio and/or other inputs that the user may be able to make. The customization information may be obtained from the user identification module 622, which interfaces with the profile data 252. The user customization module 1616 may provide the customization information to the gesture recognition module 1604.

A voice control module 1620 may receive and interpret any type of audio or voice inputs from the user. Thus, if the user makes a statement in the exercise interior, the statement may be received by a microphone, as described in conjunction with FIGS. 1O through 1R. The received signal information may be sent to the voice control module 1620 through an audio interface 854. The information may then be interpreted based on profiles 840, described in conjunction with FIG. 8A. If the voice command is determined to be a command to change a function of an exercise or other interaction with the treadmill control system 204, the voice command or its subsequent interpretation may be sent to the gesture recognition module 1604.

A verification module 1624 may be provided that can output a verification of the gesture received. The gesture recognition module 1604, after receiving information from one or more of the modules 1608 through 1620, may determine the gesture desired by the user and send that information to the verification module 1624. The verification module 1624 may then provide a name or other indication of what gesture was received through an audio interface 854 to one or more speakers, as described in conjunction with FIGS. 1O through 1R. There may be other verifications possible, such as displays of information on a display or other console that may indicate which gesture was received.

In other situations, the verification module 1624 can give a preview of the gesture function. For example, if the user desires to turn on portions of the display, the verification module 1624 can turn on the portions for a finite period of time, for example 5 seconds, and then turn the portions off.

The verification module 1624 may also be able to receive any confirmation from the user that the gesture as verified is the gesture desired by the user. For example, if the verification module 1624 states that the user desired to turn on portions of the display, the verification module 1624 can provide an audio verification that states "turn on display portions," the user can reply by saying "yes," "yes, please," or some other type of audio or other gesture input. If the user does confirm that the gesture is correct, the verification module 1624 may send this information to the gesture recognition module 1604 to enact the function or change desired by the user as confirmed by the verification module 1624.

The gesture recognition module 1604 receives information from the origin module 1608, focus module 1612, the user customization module 1616, the voice control module 1620, and/or the verification module 1624. With interactions with the modules 1608 through 1624, the recognition module 1604 can interpret which gesture, as may be indicated within the user profile data described in conjunction with FIG. 8A, the user desires to enact. Once the gesture is recognized and interpreted correctly, verified, and/or confirmed, the gesture recognition module 1604 can send information to the treadmill control module 626 to enact whatever type of gesture the user has provided.

Figure 17A:
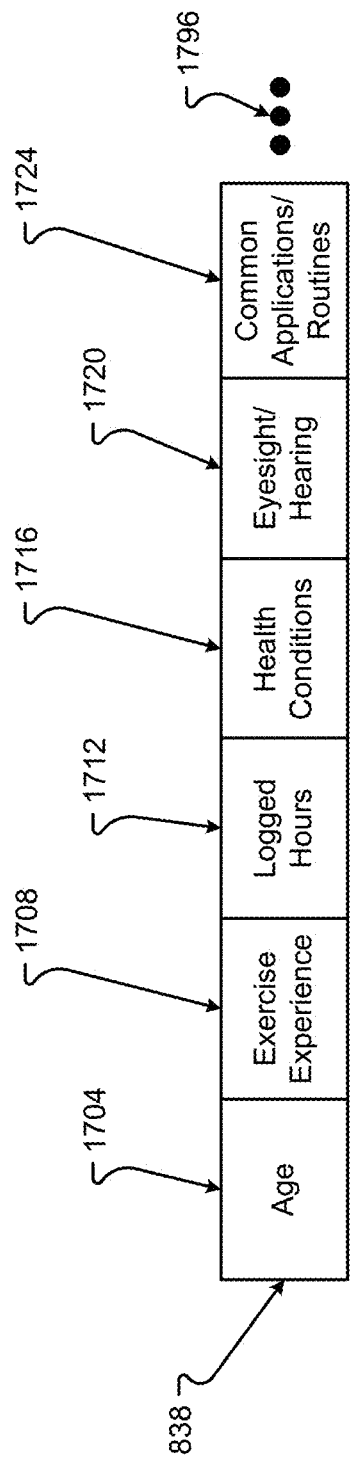
FIG. 17A is a diagram of an embodiment of a data structure for storing profile information.

An embodiment of profile information 838, which may be part of a profile database 252, as described in conjunction with FIG. 8A through FIG. 8D, may be as shown in FIG. 17A. The profile information 838 may have one or more fields. There may be more or fewer fields than those shown in FIG. 17A, as represented by ellipses 1796. The fields within the profile information 838 can include one or more of, but are not limited to, an age field 1704, an exercising experience field 1708, a logged hours field 1712, a health conditions field 1716, an eyesight/hearing field 1720, and/or a common applications/routines field 1724.

An age field 1704 may include an age or date of birth for a user. The age may be provided in years, months, days, or other increments that indicate how long the person has been alive.

The exercising experience field 1708 can include the number of years, days, months, etc. that a user has been exercising. In one example, the exercising experience 1708 may be determined by a user's first use date. The exercising experience may then be determined by the number of years, days, or other period of time between the first use date and the current date. Exercising experience 1708 may also be provided by a user.

Exercising experience 1708 can also include one or more situations in which or routines with which a user has been exercising. For example, the exercising experience 1708 may indicate a positive indication of or number of minutes, hours, or other periods of time in which different types of conditions the user has encountered. For example, the exercising conditions can include resistance levels, angle of platform, speed, time of day, interval training, or other types the conditions encountered while exercising. The exercising experience field 1708 can provide indications of whether or not a user may require assistance or have functions of exercise change based on which environment the user is currently exercising.

A logged hours field 1712 can include a number of hours a person has been in using the current routine or all exercise routines. The logged hours 1712 can give an indication of the amount of exercising experience. The logged hours 1712 can also be broken into subcategories based on the exercising experience data 1708. Thus, the exercising experience data 1708 and logged hours field 1712 may be linked by pointers or other information that indicates an exercising situation/routine or exercising experience/condition 1708 and a number of logged hours for that exercising experience in the logged hours field 1712. As such, between the exercising experience 1708 and the logged hours 1712 fields, an indication of the ability of the user may be determined.

The health conditions 1716 and the eyesight/hearing 1720 fields can give an indication of a disability for user. The health conditions field 1716 may have an indication that the user has a current health condition that may have, based on past experiences, affected the user in certain conditions. For example, if a user cannot maintain a certain pace which exercising, this problem can be indicated in exercising experience 1708, and the treadmill control system 204 may determine that the person's health conditions or eyesight/hearing is poor and requires a change in the operation of the exercise. The health conditions field 1716 may also indicate other types of health conditions problems beyond just poor health conditions, such as, fitness level, body mass, etc. may be deduced from the type of exercising done by the user. The eyesight/hearing field 1720 may also indicate the ability for a user to see or hear types of displays and/or sounds, the decibel level of sounds the user can hear or cannot hear, the brightness the user requires, whether users are able to hear or see during certain types of background events, etc. Thus, the eyesight/hearing field 1720, like the health conditions field 1716, provides information as to how the user functions in different types of conditions.

A common applications/routines field 1724 can include any type of software application on a device or a type of exercise routine used by a user with the treadmill 102. These common applications 1724 also may have an indication of how often the user uses an application or accesses that application while exercising in different conditions or how often the application is used. A common applications field 1724 may include the applications listed hierarchically based on amount of usage. As such, the treadmill control system 204 can access the applications more quickly for a particular user based on frequency of use by that user.

Figure 17B:
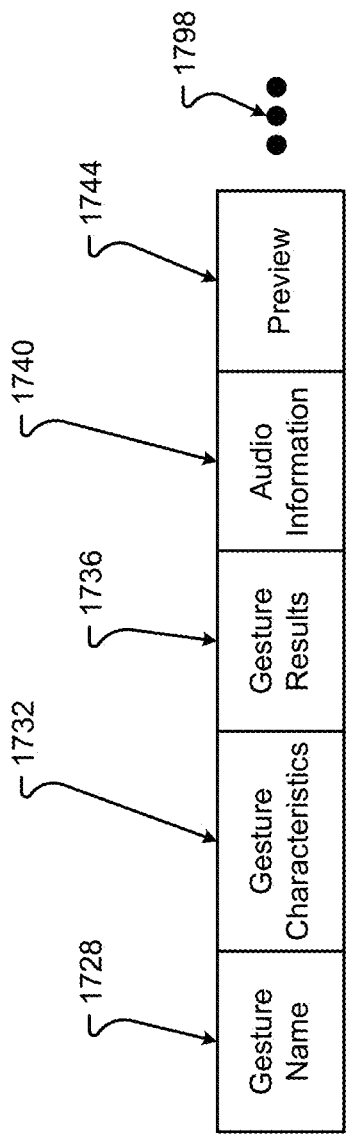
FIG. 17B is a diagram of an embodiment of a data structure for storing gesture information.

An embodiment of gesture information 832, as provided in the profile database 252 and described in conjunction with FIGS. 8A through 8D, may be as shown in FIG. 17B. The information provided in the gesture information 832 can provide information for a gesture and the associated function that the gesture may invoke. The gesture information 832 can be standardized, as each person may use the same gesture to affect the function, or may be user-created and may include the information provided from a user for certain functions. There may be a single set of information for each type of gesture. The gesture information 832 can provide any type of characteristics for the gesture that may be as described in conjunction with FIGS. 7A through 7K. The gesture information 832 can include one or more of, but are not limited to, a gesture name field 1728, a gesture characteristics field 1732, a gesture results field 1736, an audio information field 1740, a preview field 1744, etc. There may be more or fewer fields than those shown in FIG. 17B, as represented by ellipses 1798.

A gesture name field 1728 can include a name of the gesture. The gesture name 1728 may be, for example, a one word or several word description of the gesture. For example, the gesture name 1728 for turning the radio volume up may include the words "radio," "volume," and "up." The gesture name 1728 may be unique and provide both an indication to the database 252 and to the user of what gesture is being requested or completed.

Gesture characteristics field 1732 can include any of the characteristics used to determine or identify one of the gestures in FIGS. 7A through 7K. The gesture characteristics 1732 information can include any type of vocal, visual, or tactile information received by the treadmill control system 204. For example, a hand gesture in 3 dimensional space may include a configuration for a hand and a type or vector of movement that is required by the exercise control system 2004. Any of this gesture characteristics 1732 information may be stored in the gesture characteristics field 1732.

A gesture results field 1736 can include any information for the function or what type of process is required after receiving the gesture. Thus, if the user provides a gesture recognized by gesture characteristics 1732, the result 1736 should be some function performed. For example, if the user provides a gesture for turning the radio volume up, the gesture results field 1738 can include any of the functions or processes required for turning up or increasing the volume of the radio and how much of the volume should be increased.

Audio information field 1740 may be any information provided back to the user to verify the gesture and/or may be any data about a verbal command that may be associated with the gesture/function. The audio information 1740 may also include other verification parameters that may be visual. For example, if the user desires to turn the volume up on the radio, the information 1740 can include the verification response, such as, "radio volume up," which may be spoken to the user through one or more speakers 688. The audio information 1740 may also include any type of confirmation required by the user to enact the function of the gesture. For example, if the user is required to say "correct," "yes," or "enact" to cause the radio volume up gesture to be enacted, the audio information 1740 includes that response that as required by the user. The audio information field 1740 may also include any kind of visual response that may be provided to a heads up display or other display. This visual information may also include verification information, such as, a button selection or other type of interaction that is required by the user to verify the gesture.

A preview field 1744 includes any characteristics or information required to preview the gesture results 1736 for a gesture. For example, if the user provides a radio volume up gesture, the preview field 1744 may include a preview of turning a radio volume up for a specified and predetermined amount of time. For example, the volume of the radio may go up by 10% for 5 seconds. Thus, instead of having an audio or visual verification, the user can verify the command by the preview. If the preview is not correct, the user can provide information or a response for denying or confirming the command. If confirmed, the gesture results 1736 may mimic what was provided by the preview 1744.

Embodiments of different user interfaces that may be provided on display of a device 124,126 are shown in FIGS. 18A and 18B. A first user interface 1804A may include three buttons for a first function 1808, a second function 2172, and a third function 2176. The user interface 1804A can include different function buttons or user interface devices 1808 through 2176, as shown in FIG. 18A for receiving input from a user. The buttons 1808 through 2176 or user interface devices may be selectable by a user on a touch screen device or other console. The function buttons 1808 through 2176 can each have a different function associated the button 1808 through 2176. Each of the buttons 1808 through 2176 may have a different color, shape, location, or configuration visually for the user. For example, function buttons 1808 and 2172 are square, large, and at the top of the screen 1804A. A function button 2176 may be in the middle of the screen, may be rectangular, and may be larger than the first two function buttons 1808 and 2172. Each of the different configurations may be changed based on user data or interactions with the user.

A second user interface 1804B (which may provide an interface for the same application or process) is shown in FIG. 18B. Here, the buttons 1808 through 1832 may have changed based on different settings and interactions with the user. For example, function buttons 1808 through 2176 are now located at the top of the screen, are square, and are much smaller than shown in 1804A. Further, more function buttons 1820, 1824, 1828, and 1832 have been added to the user interface 1804B. For example, function button 1824 is not provided on the user interface of 1804A. Further, function buttons 1828 and 1832 are round and located the bottom of the user interface.

Both user interfaces 1804A and 1804B may be associated with a common application that may be executed by the treadmill control system 204. Thus, the common application may have different user interfaces, which may be changed based on device settings 824, profile information 838, or an interaction parameter, as determined by the exercise control system 2004. Further, one user interface 1804A may be provided to a first user, while a second user interface 1804B may be provided to a second user. Thus, depending on which user is using the user interface for device 124, 126 at which time, the user interface 1804 may change. It should be noted that any type of visual, audio, tactile, configuration of a user interface, or other interaction configurations may be changed by the exercise control system.

Figure 19:
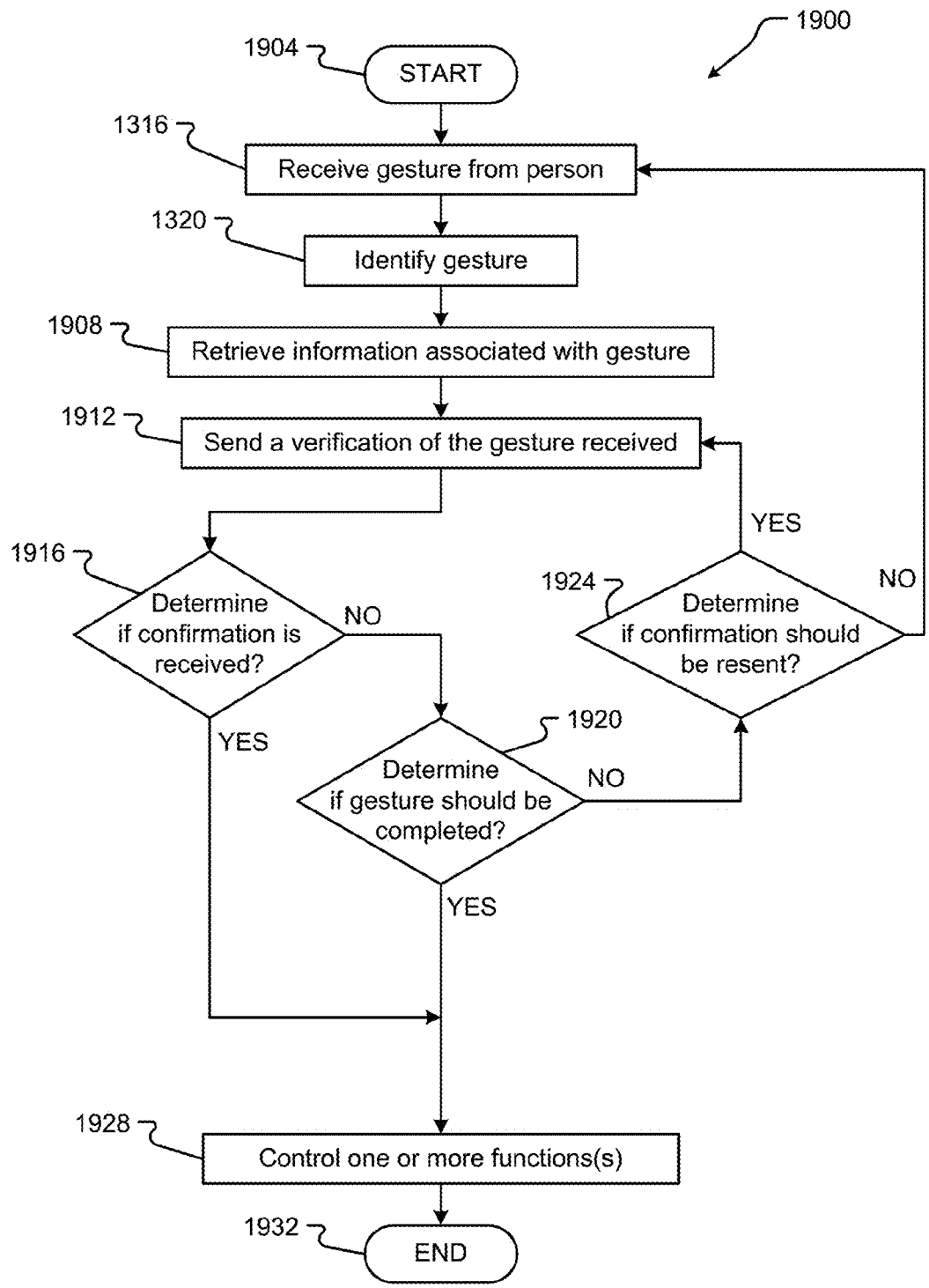
FIG. 19 is a flow or process diagram of a method for verifying a received gesture.

An embodiment of the method 1900 for receiving a gesture or other input may be as shown in FIG. 19. A general order for the steps of the method 1900 is shown in FIG. 19. Generally, the method 1900 starts with a start operation 1904 and ends with an end operation 1932. The method 1900 can include more or fewer steps or can arrange the order of the steps differently than those shown in FIG. 19. The method 1900 can be executed as a set of computer-executable instructions executed by a computer system and encoded or stored on a computer readable medium. Hereinafter, the method 1900 shall be explained with reference to the systems, components, modules, software, data structures, user interfaces, etc. described in conjunction with FIGS. 1-18.

A receive step 1226, which may be as described in conjunction with FIG. 13, may receive a gesture. The gesture may be provided to a gesture recognition module 1604. The gesture recognition module 1604 may also receive a voice input or other type of input into a display for a device 124,126. The gesture recognition module 1604 may then identify the gesture, in step 1320, which may be as described in conjunction with FIG. 13. Once the gesture is identified, the gesture information may be provided from the database, as described in conjunction with FIG. 19B, to a verification module 1624.

The verification module 1624 may retrieve the gesture information, in step 1908. The information may be retrieved from information sent by the gesture recognition module 1604 or by information that is accessed through the profile database 252, as described in conjunction with FIG. 13. The gesture information can include any kind of characteristics or information 1732-1744 required by the verification module 1624 to send a verification to the user.

The verification module 1624 may then retrieve the audio or visual information from field 1740 or the preview or other type of information from field 1744 to send the verification, in step 1912. Here, the verification module 1624 may provide an audio verification output (i.e., an audible message) to an audio input/output interface 654 to send to one more speakers 688. This audio output can include the name of the gesture 1728 or other information that may be provided in the data field 1740. For example, if the user provided a gesture that is recognized as increasing the speed, the verification module 1624 may provide an audio output that states "increase speed" through the speaker 688. The verification module 1624 may access the media controller 348 to signal a speech synthesis module to provide a voice-like audio output that states "increase speed" through the audio input/output interface 654 to the speakers 688. In this way, a synthesized human voice may state what gesture was recognized by the gesture recognition module 1604.

In other examples, the verification module 1624 can provide a visual indication of the gesture as recognized. For example, a verification message or user interface message may be displayed on a display on one of the consoles 124, 126. For example, a message "increase speed," in text, may be displayed on one of the user interfaces for devices 124, 126. In other situations, a symbolic character, such as a flashing light bulb, may be presented that indicates the gesture requested was that the speed be increased. The visual indication may be provided on one more the visual user interfaces for devices 124, 126 and may include some type of confirmation button or user interface device that may be selected to confirm that verified gesture is associated with the correct function desired by the user. In still other examples, another user interface device may be provided that states that the verified gesture is incorrect.

In other examples, the verification module 1624 may provide a preview, as described in preview field 1744. A preview of increased speed may require the verification module 1624 to send a signal to the motor control module to control an exercise subsystem 328. The treadmill control module 626 can send an "increased speed" signal to the motor control to increase the speed 10%. The preview may then be presented with the either an audio or visual confirmation request. For example, one more user interface devices may be presented on one or more user interfaces for devices 124, 126 that may be selected by the user to either confirm or to deny that the preview is associated with the correct function. An audio indication may also be provided asking whether the preview was correct.

A user may then provide either a confirmation or a denial to the verification module 1624 of whether the verified gesture is correct. The verification module 1624 can determine if a confirmation is received, in step 1916. Here, the verification module 1624 may receive a signal through the audio input/output interface 654, video input/output interface 664, a video controller, an audio controller, other system that controls the input side of the devices 124,126. Thus, a module can send a signal back to the verification module 1624 to indicate whether a user selectable device, confirming the verification, was selected. Further, the audio input/output interface 654 may receive an audible confirmation as a signal from a microphone that can be sent to the verification module 1624, And in still other examples, one or more sensors, as described herein, may determine if a second gesture, as a confirmation indication, is received from the user. Regardless, some type of user action may be perceived and sent to the verification module 1624. If the user has confirmed the gesture as recognized, the method 1900 proceeds YES to step 1928. However, if no confirmation or a denial is received, the method 1900 may proceed NO to step 1920, where the function is not completed and the system awaits another command or another gesture.

In step 1920, the verification module 1624 can determine whether to complete the function associated with the gesture. For example, if the user provides no confirmation, but a confirmation is assumed if no confirmation occurs after a predetermined period of time, for example 5 seconds, the gesture may still be completed. As such, the user may acquiesce to a function without interaction. Thus, no confirmation or no interaction from user may be a confirmation. If the gesture is to be completed, the method 1900 proceeds YES to step 1928. However, if the gesture is not to be completed, the method 1900 may proceed NO to step 1924.

In some situations, the verification module 1624 may determine to resend the verification message, in step 1924. For example, if no confirmation is received and the gesture is not to be completed unless a confirmation is indicated, the verification module 1624 may require at least some type of confirmation. As such, if the verification is to be resent, the method 1900 proceeds YES back to step 1912 where the verification module 1624 may resend the verification message either visually, audibly, tactilely, by vibration, or through another type of signal. The verification module 1624 may then wait for a period of time to determine if the confirmation is sent. The verification module 1624 may resend the verification message some predetermined number of times before determining that the gesture is denied or is not confirmed. If the verification is not to be resent, the method 1900 proceeds NO back to receive step 1226, where the gesture may be resent, and the user may try and input the gesture again and have the gesture re-recognized because the verified gesture was either wrong or inadvertent.

In step 1928, the verification module 1624 confirms that the gesture was recognized accurately and sends that indication back to the gesture recognition module 1604. The gesture recognition module 1604 may then send a signal to the treadmill control module 626 to complete a function associated with the gesture. The treadmill control module 626 may then enact any type of function associated with that gesture. The signal sent from the gesture recognition module 1604 can provide either the gesture or the function information. If the treadmill control module 626 receives the gesture information, the treadmill control module 626 may look up the function associated with that gesture in a database, as described in conjunction with FIG. 13. As such, the treadmill control module 626 may retrieve the gesture results information 1736 and enact the function required by the gesture.

Figure 20:
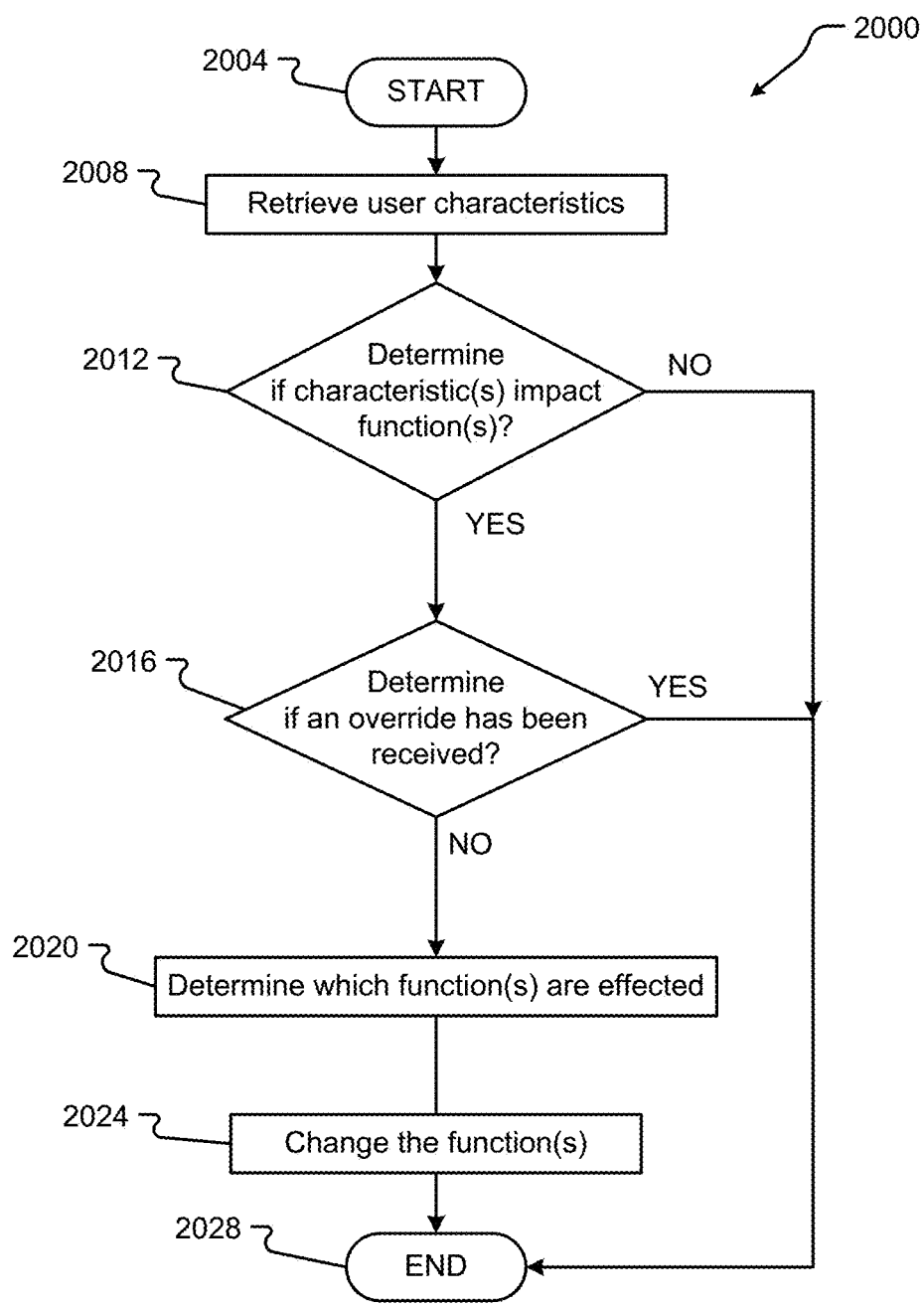
FIG. 20 is a flow or process diagram of a method for change exercise functions based on user characteristic(s)

An embodiment of a method 2000 for changing the function of an exercise based on user characteristics is as shown in FIG. 20. A general order for the steps of the method 2000 is shown in FIG. 20. Generally, the method 2000 starts with a start operation 2004 and ends with an end operation 2028. The method 2000 can include more or fewer steps or can arrange the order of the steps differently than those shown in FIG. 20. The method 2000 can be executed as a set of computer-executable instructions executed by a computer system and encoded or stored on a computer readable medium. Hereinafter, the method 2000 shall be explained with reference to the systems, components, modules, software, data structures, user interfaces, etc. described in conjunction with FIGS. 1-19.

The user identification module 622 can retrieve user characteristics, settings, profile information, etc., in step 2008. The retrieval of settings from a user 838 may be as described herein. Thus, FIG. 20 may be a further addendum to customization of the exercise based on user profile 838. Here, the user may be recognized as described previously herein. The user identification module 622 may then retrieve user characteristics, in step 2008. The user identification module 622 may retrieve the information as described in conjunction with FIG. 19A. This information may then be sent to a user customization module 1616.

The user customization module 1616 may then access the characteristic(s), as described in conjunction with FIG. 13, to determine if any of the characteristics may impact the function of the exercise, in step 2012. Here, the user customization module 1616 may use one more rules to determine if any of the characteristics are over or under a benchmark or within an area of concern. The rules may include quantitative or qualitative assessments of the different characteristics. For example, if the user's age 1704 is below a predetermined age, for example, age 20, the user customization module 1616 may determine that that characteristic requires some type of customization or change to a function of the exercise.

The user customization module 1616, if determining that the characteristic does impact a function, may then retrieve any type of the settings 824 that may be required or needed to address that characteristic. The settings information may then be sent to a treadmill control module 626. Thus, if the characteristics do impact a function of the exercise, the method 2000 proceeds YES to step 2016. However, if no characteristic does affect a function of an exercise, the method 2000 proceeds NO to end step 2028.

The treadmill control module 626 or the user customization module 1616 may then determine if there was an override, in step 2016. An override may be a user-provided or an automatic override that eliminates the adjustment of any of the exercise functions based on user characteristics. The override, if set, may require the treadmill control module 626 or the user customization module 1616 to ignore or not adopt any of the settings provided in field 1184. If there an override set or enacted, method 2000 proceeds YES to end step 2028. However, if no override is provided, method 2000 proceeds NO to step 2020.

The treadmill control module 626 may then determine which functions are affected by the characteristics, in step 2020. Here, the treadmill control module 626 may retrieve settings 824 that are associated with the changes based on the characteristics. In other situations, the treadmill control module 626 may access a standardized set of changes required based on a characteristic. For example, if a person's eyesight is poor, the standardized set of functions that are changed are to increase the size, vibrancy, and accessibility of any of the controls provided on a user interface for device 124,126. Other changes may be associated with other different characteristics.

The treadmill control module 626 then proceeds to change those functions, in step 2024. Here, the treadmill control module 626 may send one more commands or control signals through one more modules to change the functions of the exercise. The different functions may then be modified to control user interfaces, exercise functions, or other types of processes, functions, or means that modify how the exercise interacts with the user or how the exercise operates. The changes may include gesture preferences, exercises settings, infotainment system controls, access and manipulation of the display, console functions or layouts, or one or more exercises subsystems.

An example includes changing access to exercise features or functions based on the user's age 1704, exercising experience 1708, logged hours 1712, or other characteristic. For example, a user may have an age 1704 that is under some benchmark (the user is 16 and under the benchmark age of 20) that causes one or more exercise functions to be changed. For example, a heart rate goal is set higher than someone over 20.

Figure 21:
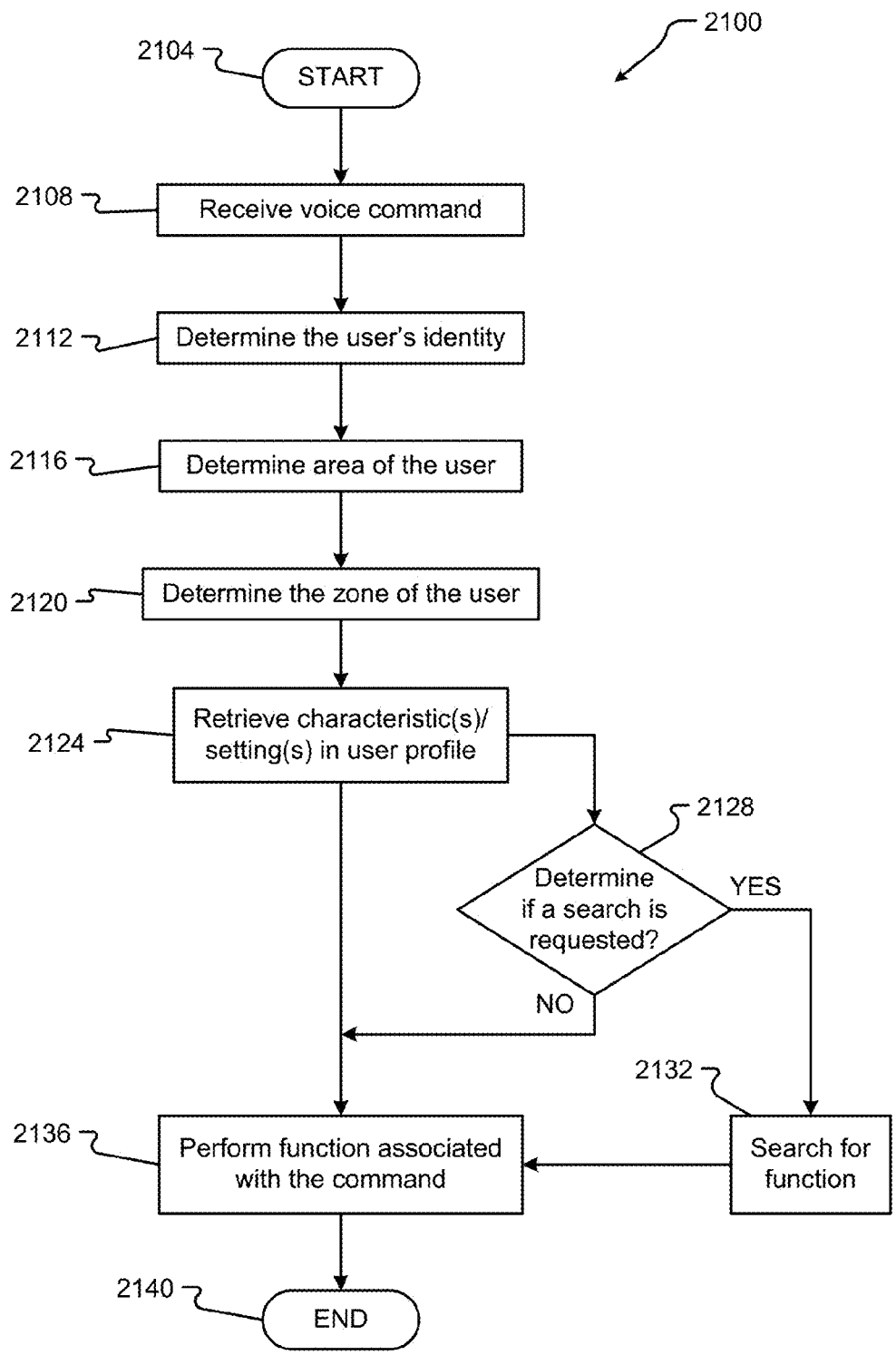
FIG. 21 is a flow or process diagram of a method for receiving a voice command.

An embodiment of a method 2100 for receiving voice commands in the exercise environment is shown in FIG. 21. A general order for the steps of the method 2100 is shown in FIG. 21. Generally, the method 2100 starts with a start operation 2104 and ends with an end operation 2140. The method 2100 can include more or fewer steps or can arrange the order of the steps differently than those shown in FIG. 21. The method 2100 can be executed as a set of computer-executable instructions executed by a computer system and encoded or stored on a computer readable medium. Hereinafter, the method 2100 shall be explained with reference to the systems, components, modules, software, data structures, user interfaces, etc. described in conjunction with FIGS. 1-27.

A voice control module 1620 may interface with a sensor module 614 to receive voice commands, in step 2108. The audio signal is received, by a microphone, and provided through the audio I/O interface 654 to the voice control module 1620. The voice command can then be interpreted by the voice control module 1620.

A user identification module 622 can identify a user within the exercise, in step 2112. The identification of the user may be as described in conjunction with FIG. 13. Further, the user identification module 622 can receive sensor information from the sensor module 614 to determine an area 408 in which the person or user occupies, in step 2116, and determine the zone 412 which the user occupies, in step 2120. The detection of which area 408 and zone 412 the user is in may be as described in conjunction with FIG. 13.

Based on the identity of the user, the user identification module 622 may then retrieve characteristics or settings in a user profile 838 and profile data 252, in step 2124. The characteristics and settings of the profile 838 may be as described herein. This information may be retrieved as described in conjunction with FIG. 13. The settings or profile data may be as described herein, and may indicate one or more different audio commands that are associated with the user.

Each user may have a customizable set of audio settings that the user can provide and store, as described herein. Further, there may be a standard set of audio commands that any user may use within the exercise. One audio command that may be completed is a search. Thus, the user may search for a function or command audibly. The voice control module 1620 can determine if a search is being conducted, in step 2128. A search may be one type of command that can be used anywhere within the exercise. Thus, the voice control module 1620 may search for gesture or voice information in field 1740 to determine if a search command is being executed. If a search command is not being executed, the method proceeds NO to step 2128. However, if a search is being conducted, the method 2100 proceeds YES to step 2132 where the voice control module 1620 provides the search information to the gesture recognition module 1604. The gesture recognition module 1604 may then instruct the media controller 348 or the treadmill control module 626 to provide a search function, in step 2132. Information about the search function may be included and then used to identify another function.

The treadmill control module 626 may then perform the function based on the verbal communication(s), in step 2132. Thus, if the voice command is identified, the information is sent to the treadmill control module 626. The treadmill control module 626 may perform the function based on the received information, in step 2132. In this way, the voice command can be used for the exercise systems, as described herein.

Figure 22:
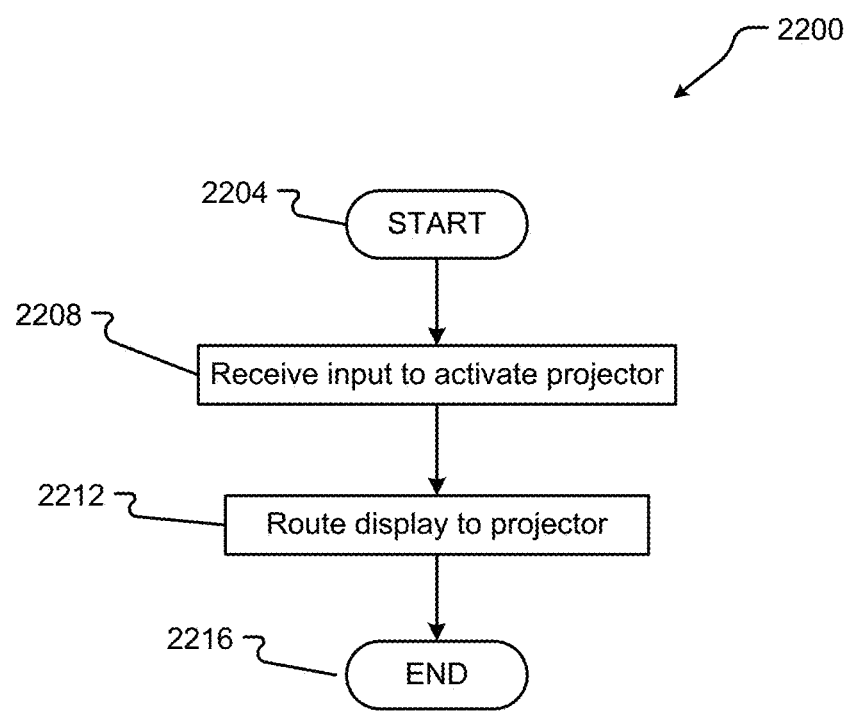
FIG. 22 is a flow or process diagram of a method for changing a user interface to a projector mode.

An embodiment 2200 of configuring a user interface to be projected from a projector is shown in FIG. 22. A general order for the steps of the method 2200 is shown in FIG. 22. Generally, the method 2200 starts with a start operation 2204 and ends with an end operation 2216. The method 2200 can include more or fewer steps or can arrange the order of the steps differently than those shown in FIG. 22. The method 2200 can be executed as a set of computer-executable instructions executed by a computer system and encoded or stored on a computer readable medium. Hereinafter, the method 2200 shall be explained with reference to the systems, components, modules, software, data structures, user interfaces, etc. described in conjunction with FIGS. 1-28.

The device interaction module 618 may receive a command to activate a projector, in step 2208. Here, the device interaction module 618 may receive a gesture, voice command, or other input to use the projector, as shown in FIGS. 1S through 1U. The command may be send to the video I/O interface 664 to change the output of the displays. The video I/O interface 664 may then route the video output to the projector 186 for display on a surface 184, as shown in FIG. 15, in step 2212.

The exemplary systems and methods of this disclosure have been described in relation to configurable exercise equipment consoles and associated devices. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, options, and/or configurations illustrated herein show the various components of the system collocated, certain components of the system can be located remotely, at distant portions of a distributed network, such as a local area network (LAN) and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a private branch exchange (PBX) and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or very-large-scale-integration (VLSI) design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or computer-generated imagery (CGI) script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for interacting with exercise equipment by a user, comprising:
    an exercise control system, including a processor, receiving a gesture from the user in three-dimensional space;
    the exercise control system identifying the received gesture;
    the exercise control system sending a verification of the received gesture to the user;
    the exercise control system determining if a confirmation is received in response to the verification;
    if the confirmation is received, the exercise control system controlling a function associated with the received gesture;
    if the confirmation is not received, the exercise control system determining if the received gesture should be completed;
    if the received gesture should be completed, the exercise control system controlling the function associated with the received gesture;
    if the received gesture should not be completed, the exercise control system determining if the verification should be resent;
    if the verification should be resent, the exercise control system again sending the verification, and
    if the verification should not be resent, the exercise control system receiving another gesture.

2. The method of claim 1, wherein the verification is an audible message presented to the user.

3. The method of claim 2, wherein the confirmation is a second gesture.

4. The method of claim 2, wherein the confirmation is an audible confirmation.

5. The method of claim 1, wherein the verification is a user interface message presented on a screen.

6. The method of claim 5, wherein the confirmation is a selection of a user interface device on the screen.

7. The method of claim 1, wherein the verification is a preview of the function associated with the received gesture.

8. A method for interacting with exercise equipment by a user, comprising:
    an exercise control system, including a processor, receiving a gesture from the user in three-dimensional space;
    the exercise control system identifying the received gesture;
    the exercise control system sending a verification of the received gesture to the user;
    the exercise control system determining if a confirmation is received in response to the verification;
    the exercise control system receiving a denial of the verification; and
    based on the denial, the exercise control system not completing the function associated with the received gesture.

9. The method of claim 8, wherein if the confirmation is not received, the exercise control system determining if the received gesture should be completed.

10. The method of claim 8, wherein the verification is an audible message presented to the user.

11. The method of claim 8, wherein the denial of the verification is received from the user.

12. The method of claim 8, wherein the exercise control system receives a second gesture from the user.

13. An exercise control system, comprising:
    a processor; and
    a computer-readable storage medium storing computer-readable instructions, which when executed by the processor cause the processor to perform:
    receiving a gesture from a user in three-dimensional space;
    identifying the received gesture;
    sending a verification of the received gesture to the user;
    determining if a confirmation is received in response to the verification;
    if the confirmation is received, controlling a function associated with the received gesture;
    if the confirmation is not received, determining if the received gesture should be completed;
    if the received gesture should be completed, controlling the function associated with the received gesture;
    if the received gesture should not be completed, determining if the verification should be resent;
    if the verification should be resent, again sending the verification; and
    if the verification should not be resent, receiving another gesture.

14. The exercise control system of claim 13, wherein the verification is an audible message presented to the user.

15. The exercise control system of claim 14, wherein the confirmation is a second gesture.

16. The exercise control system of claim 14, wherein the confirmation is an audible confirmation.

17. The exercise control system of claim 13, wherein the verification is a user interface message presented on a screen.

18. The exercise control system of claim 17, wherein the confirmation is a selection of a user interface device on the screen.

19. The exercise control system of claim 13, wherein the verification is a preview of the function associated with the received gesture.

20. The exercise control system of claim 13, wherein the computer-readable instructions, when executed by the processor, additionally cause the processor to perform:
   receiving a denial of the verification; and
   based on the denial, not completing the function associated with the received gesture.

* * * * *